(12) United States Patent
Lee et al.

(10) Patent No.: US 10,667,691 B2
(45) Date of Patent: Jun. 2, 2020

(54) COMPRESSED SENSING HIGH RESOLUTION FUNCTIONAL MAGNETIC RESONANCE IMAGING

(71) Applicant: The Board of Trustees of the Leland Stanford Junior University, Stanford, CA (US)

(72) Inventors: Jin Hyung Lee, Stanford, CA (US); Zhongnan Fang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 158 days.

(21) Appl. No.: 15/749,767

(22) PCT Filed: Aug. 30, 2016

(86) PCT No.: PCT/US2016/049508
§ 371 (c)(1),
(2) Date: Feb. 1, 2018

(87) PCT Pub. No.: WO2017/040538
PCT Pub. Date: Mar. 9, 2017

(65) Prior Publication Data
US 2019/0150742 A1 May 23, 2019

Related U.S. Application Data

(60) Provisional application No. 62/212,335, filed on Aug. 31, 2015.

(51) Int. Cl.
| | | |
|---|---|---|
| *A61B 5/00* | (2006.01) | |
| *A61B 5/026* | (2006.01) | |
| *G01R 33/48* | (2006.01) | |
| *G01R 33/56* | (2006.01) | |
| *G01R 33/561* | (2006.01) | |

(Continued)

(52) U.S. Cl.
CPC .......... *A61B 5/0042* (2013.01); *A61B 5/0263* (2013.01); *A61B 5/055* (2013.01); *A61B 5/4064* (2013.01); *A61B 5/7203* (2013.01); *A61B 5/7253* (2013.01); *G01R 33/4806* (2013.01); *G01R 33/4824* (2013.01); *G01R 33/4826* (2013.01); *G01R 33/5608* (2013.01);
(Continued)

(58) Field of Classification Search
CPC ............ G01R 33/4806; G01R 33/4824; G01R 33/4826; G01R 33/5608; G01R 33/5614; G01R 33/56308; A61B 5/0042; A61B 5/0263; A61B 5/055; A61B 5/4064; A61B 5/7203; A61B 5/7253; A61B 2576/026
USPC ......................................... 324/300, 307, 309
See application file for complete search history.

(56) References Cited

U.S. PATENT DOCUMENTS

| | | | | |
|---|---|---|---|---|
| 2006/0058619 A1* | 3/2006 | DeYoe | ..................... | G06T 11/00 600/407 |
| 2007/0159174 A1* | 7/2007 | Oshio | ................ | G01R 33/4822 324/318 |

(Continued)

FOREIGN PATENT DOCUMENTS

WO      2015034951      3/2015

*Primary Examiner* — Hoai-An D. Nguyen
(74) *Attorney, Agent, or Firm* — Rudy J. Ng; Paula A. Borden; Bozicevic, Field & Francis LLP

(57) ABSTRACT

The present disclosure provides methods and systems for high-resolution functional magnetic resonance imaging (fMRI), including real-time high-resolution functional MRI methods and systems.

20 Claims, 63 Drawing Sheets

(51) Int. Cl.
 *A61B 5/055* (2006.01)
 *G01R 33/563* (2006.01)
(52) U.S. Cl.
 CPC ... *G01R 33/5614* (2013.01); *G01R 33/56308* (2013.01); *A61B 2576/026* (2013.01)

(56) References Cited

U.S. PATENT DOCUMENTS

2008/0197842 A1 8/2008 Lustig et al.
2014/0085318 A1 3/2014 Nadar et al.

* cited by examiner

Low-res Nyquist
FOV = W, nIntlv = 10,
T_acq = T.

High-res Nyquist
FOV = W, nIntlv = 53,
T_acq = 5.3T.

High-res VDS
FOV = W, nIntlv = 30,
T_acq = 3T.

HSPARSE VDS
FOV = W, nIntlv = 10,
T_acq = T.

High-res VDS sampling trajectory 30 interleaves/kz slice
32 slices
960 interleaves in total

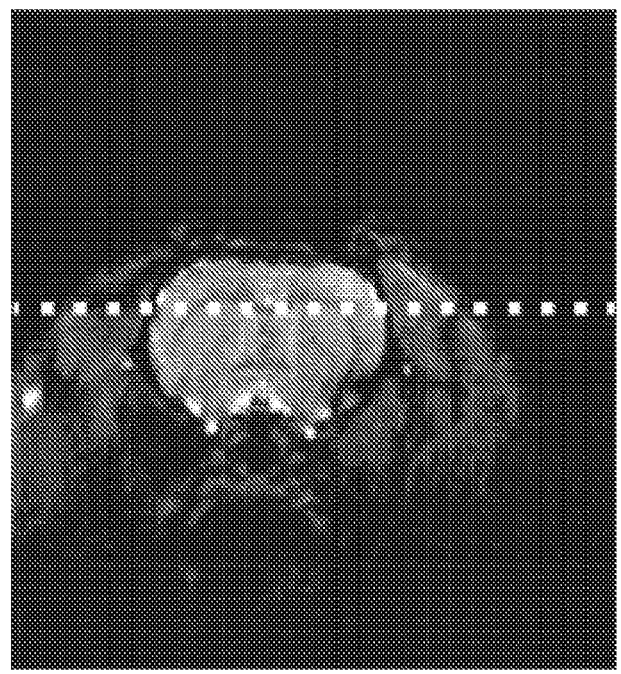
FIG. 2B
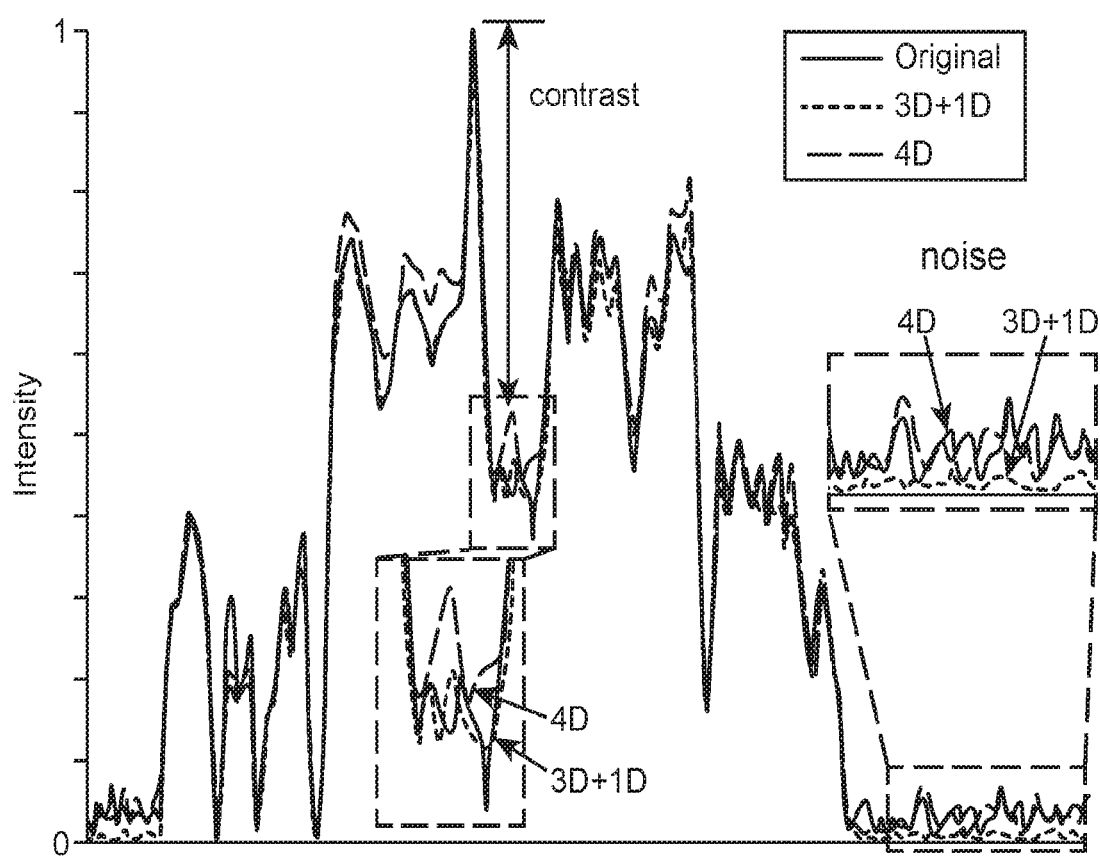

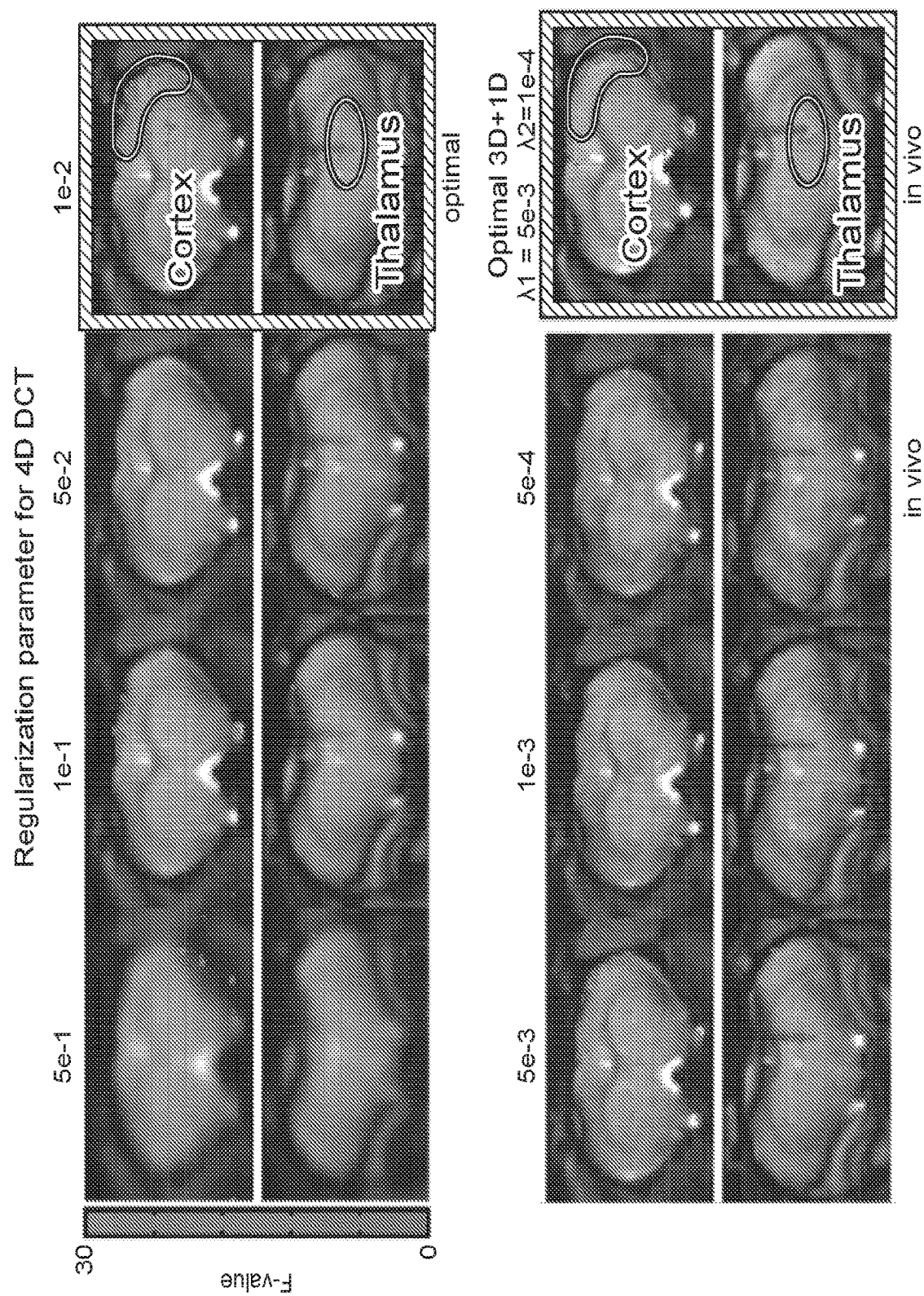

FIG. 2F
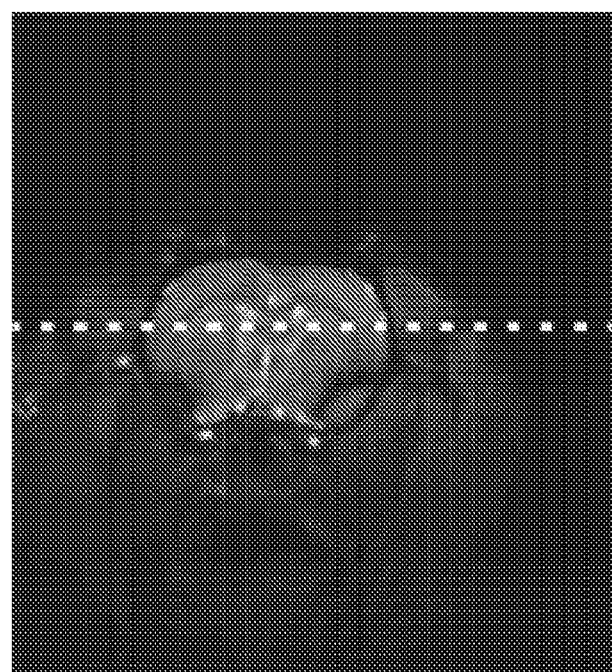
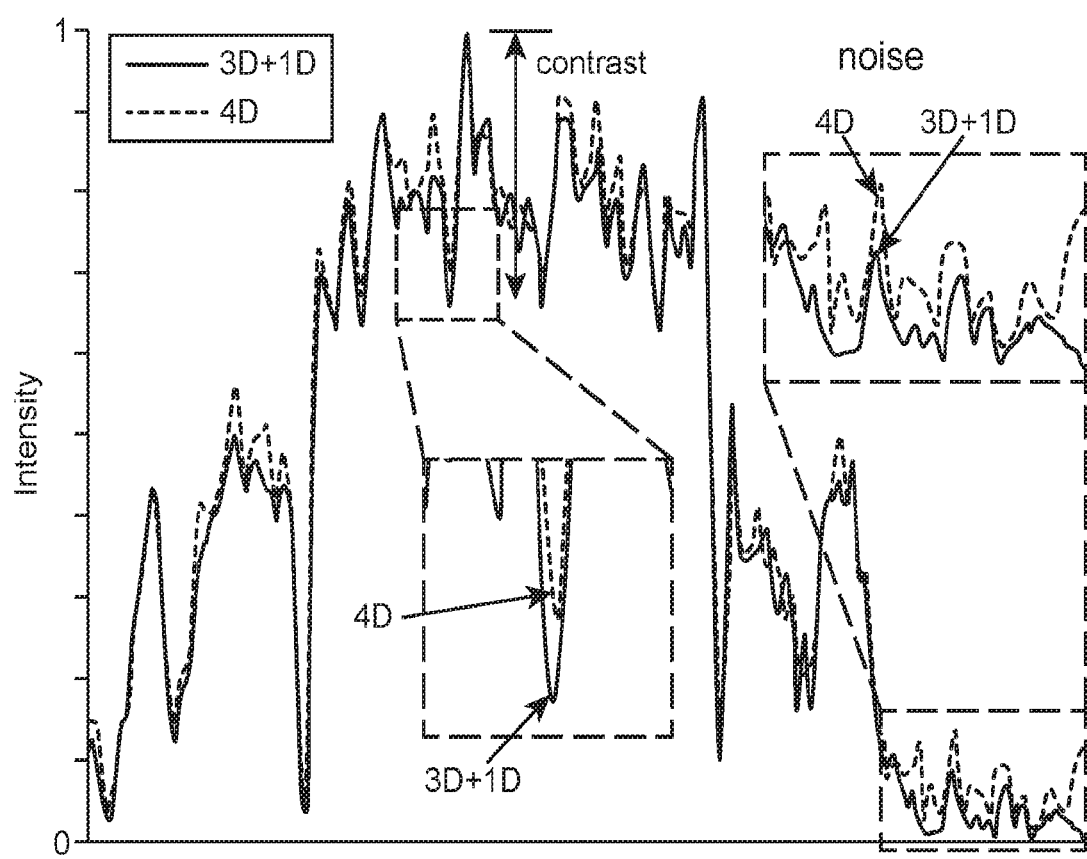

FIG. 2G
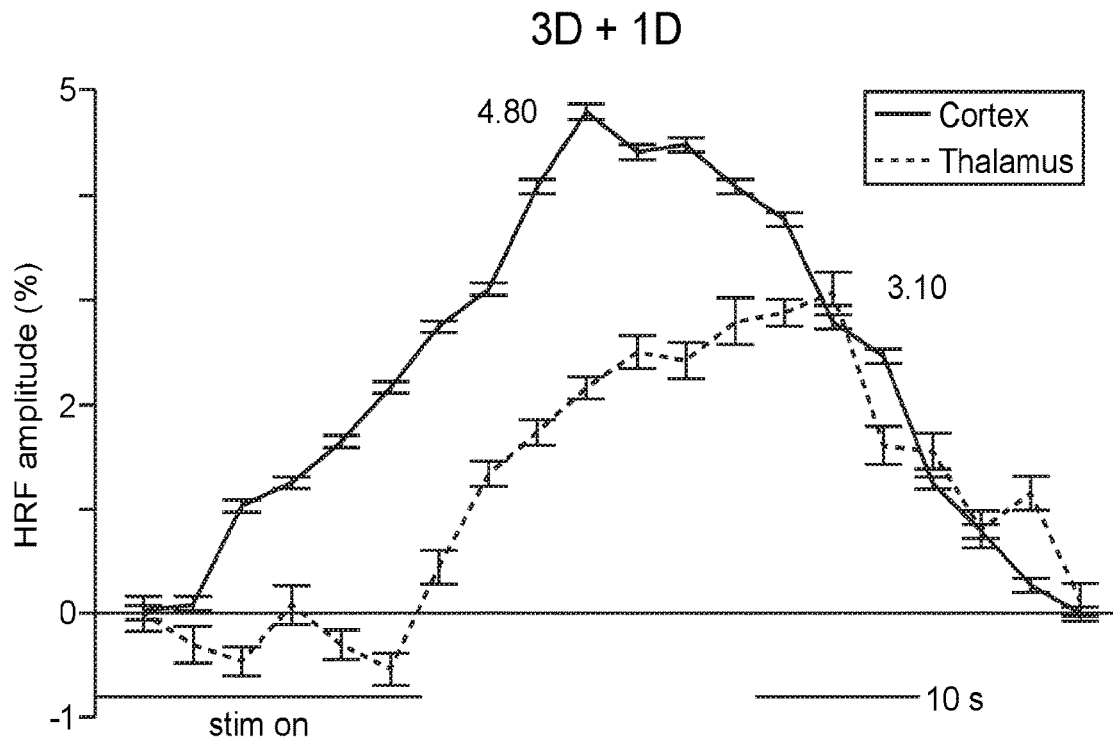
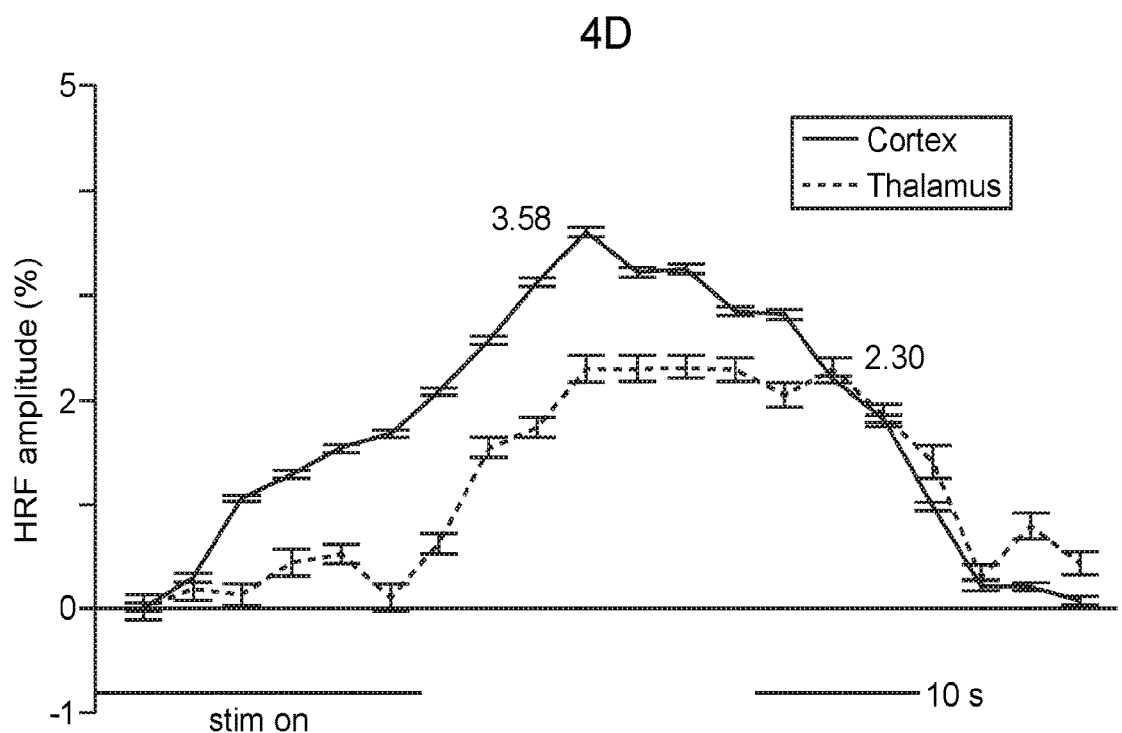

FIG. 4

Fast Gradient Descent Method $m_0 \leftarrow 0$;
while $k <$ maxIter

/* 1. Find gradient descent direction */
$g_k = \nabla f(m_k)$; /* this step also gives $f(m_k)$ and $Fm_k - y$ */

/* 2. Pre-compute line search decompositions */
$f_d = Fm_k - y$;
$f_g = Fg_k$;

$a = \frac{1}{2}\|f_d\|^2$;

$b = R\langle f_d, f_g \rangle$ $c = \frac{1}{2}\|f_g\|^2$;

$d = f(m_k)$;

$e = g_k^T g_k$;

/* 3. Find descent step size */
$t = 1$;
$\tilde{m} = m_k - tg_k$;
while $a + tb + t^2c + \lambda_1\|\Psi_t\tilde{m}\|_1 + \lambda_2\|\Psi_s\tilde{m}\|_1 > d + t\alpha e$
    $t = \beta t$; /* If not descending, reduce step */
    $\tilde{m} = m_k - tg_k$;

/* 4. Update the image */
$m_{k+1} = \tilde{m}$;

/* 5. Test if converges */
if $\left(\frac{1}{4}\sum_{n=k-3}^{k}(f(m_n) - f_{\tilde{m}})\right) / f_{\tilde{m}} < \epsilon$
    break;

FIG. 6A
Sensitivity test
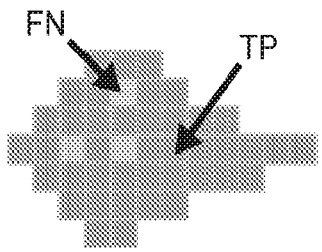
$$SEN = \frac{TP}{FN + TP}$$
FIG. 6B
False positive rate
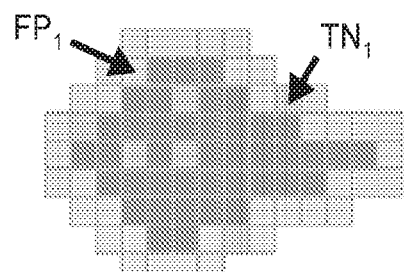 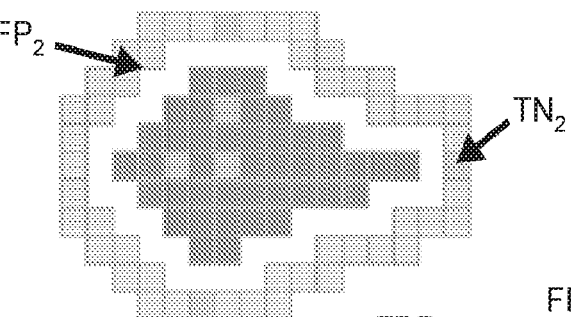
$$FPR_1 = \frac{FP_1}{FP_1 + TN_1} \qquad FPR_2 = \frac{FP_2}{FP_2 + TN_2}$$

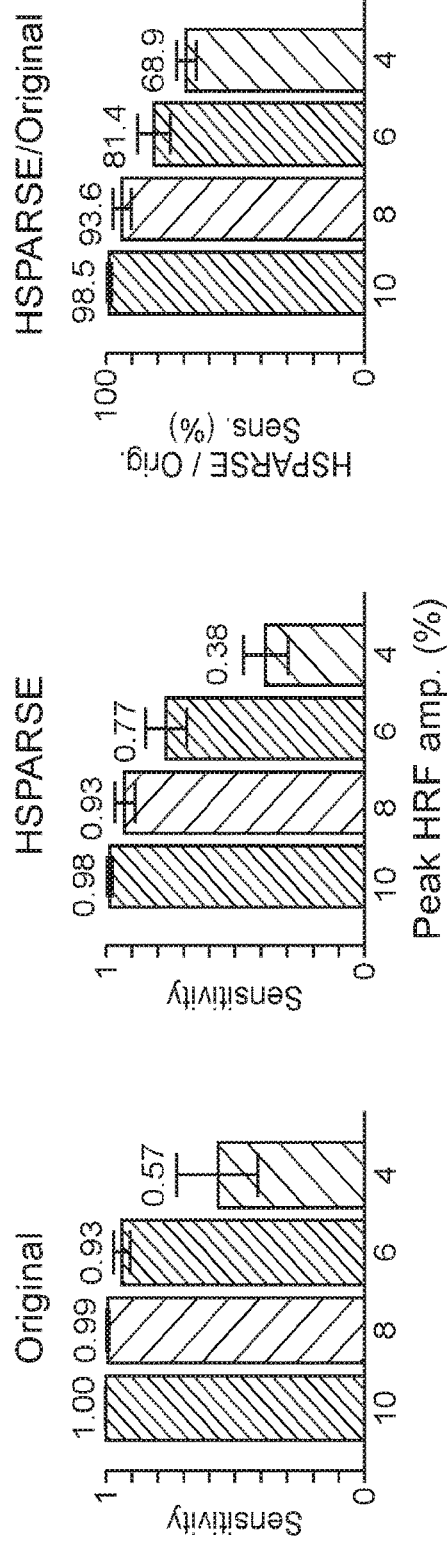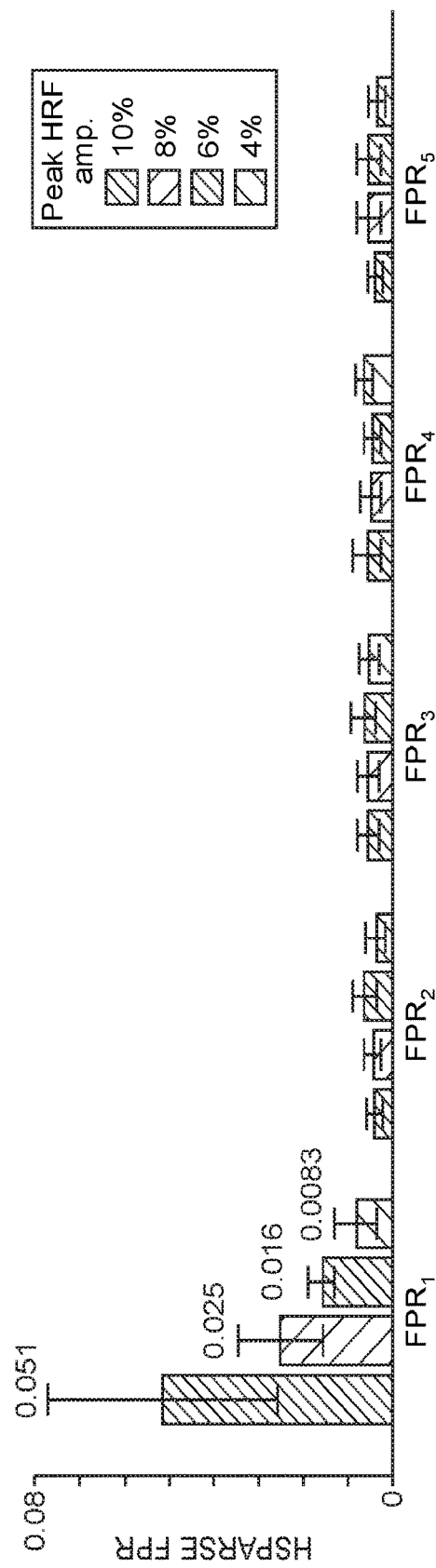
FIG. 6D
FIG. 6E

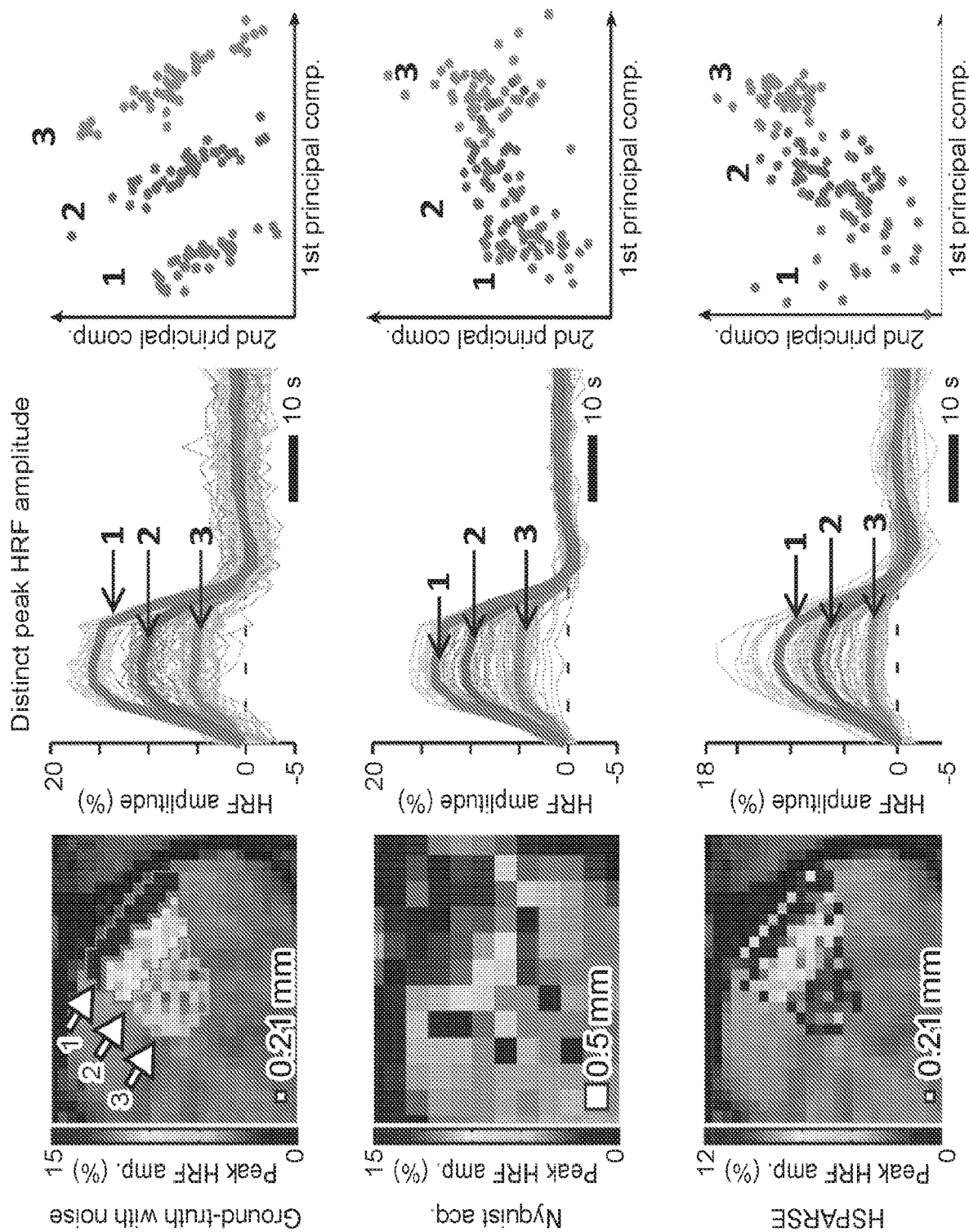

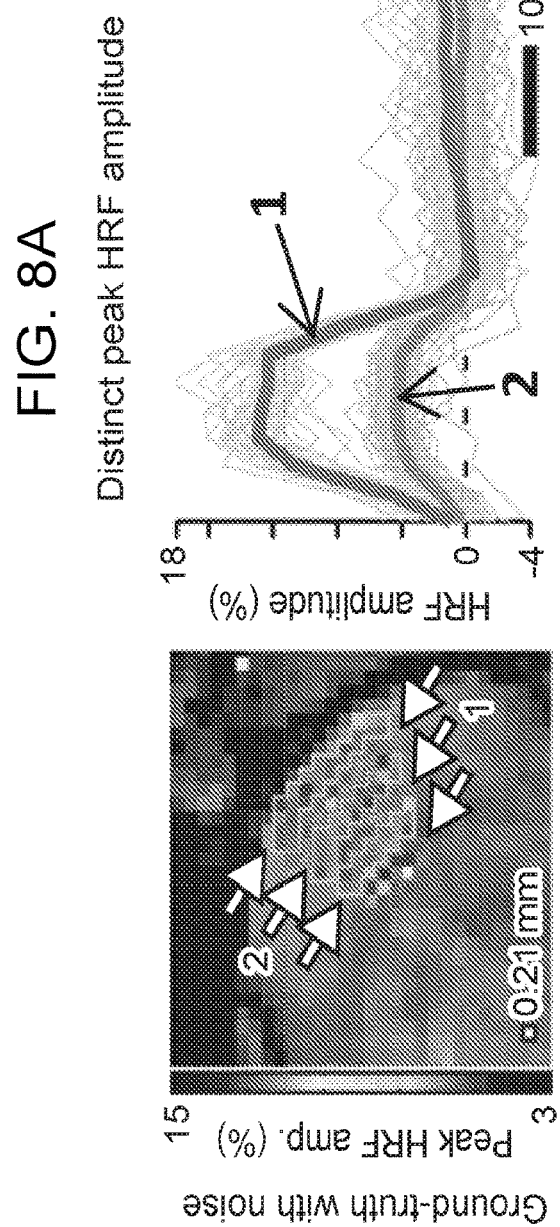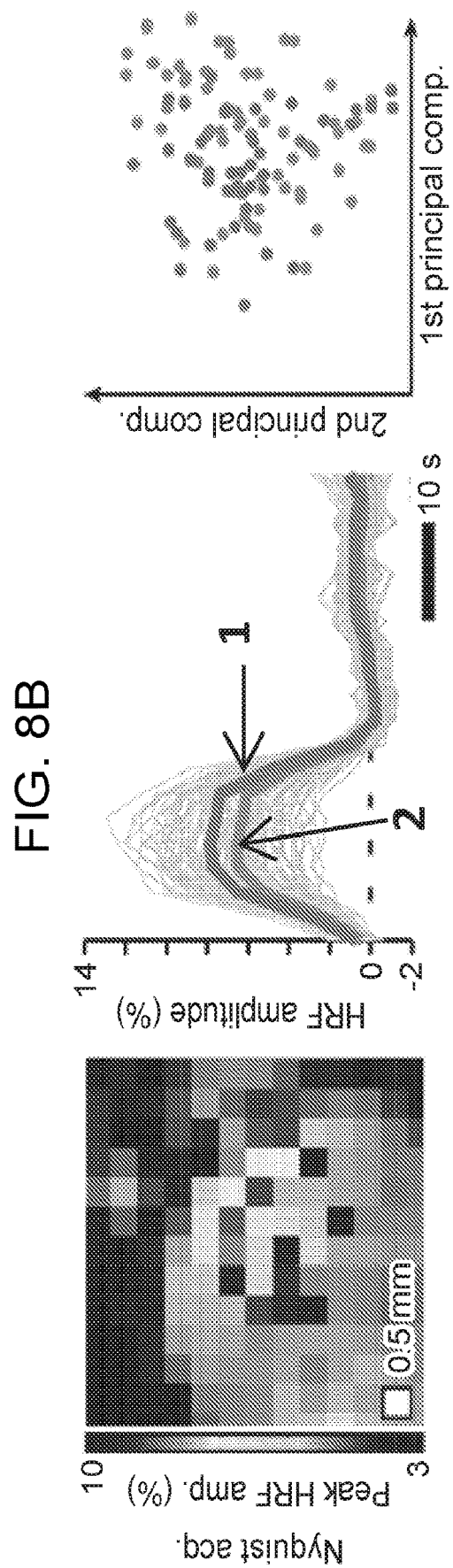

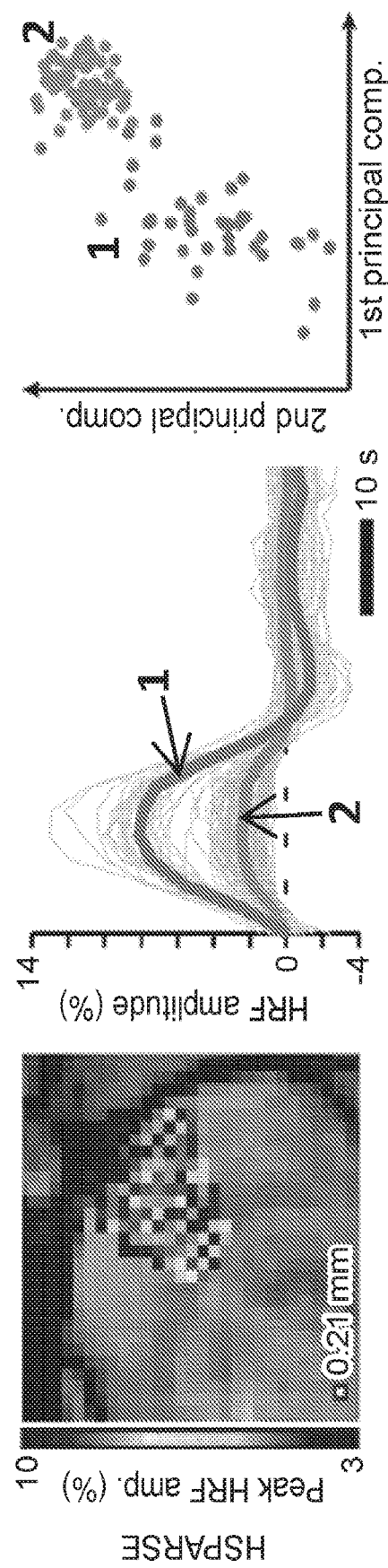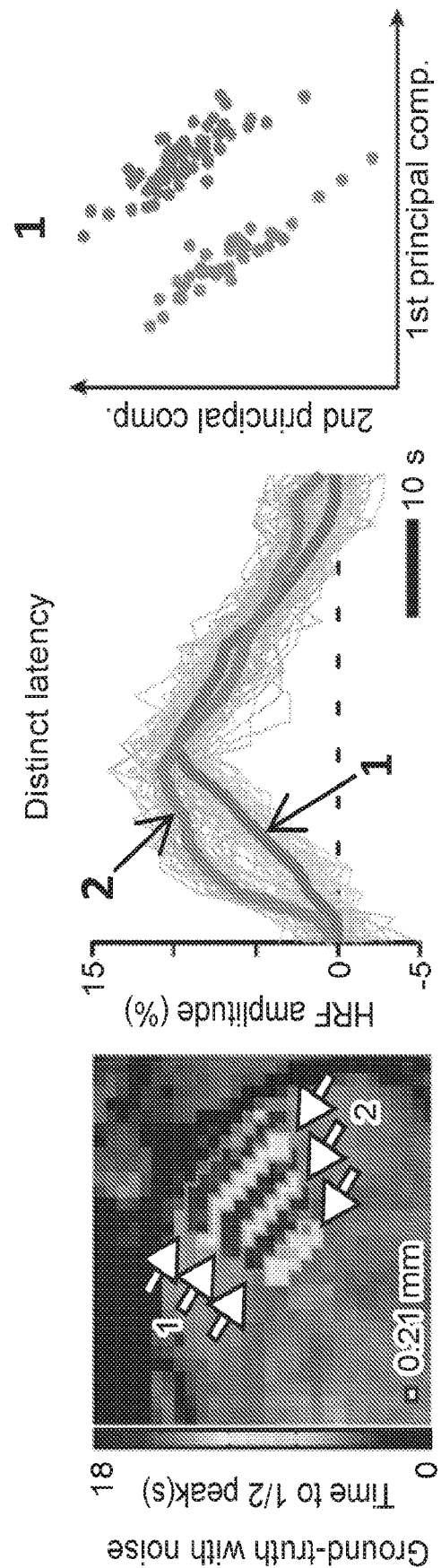

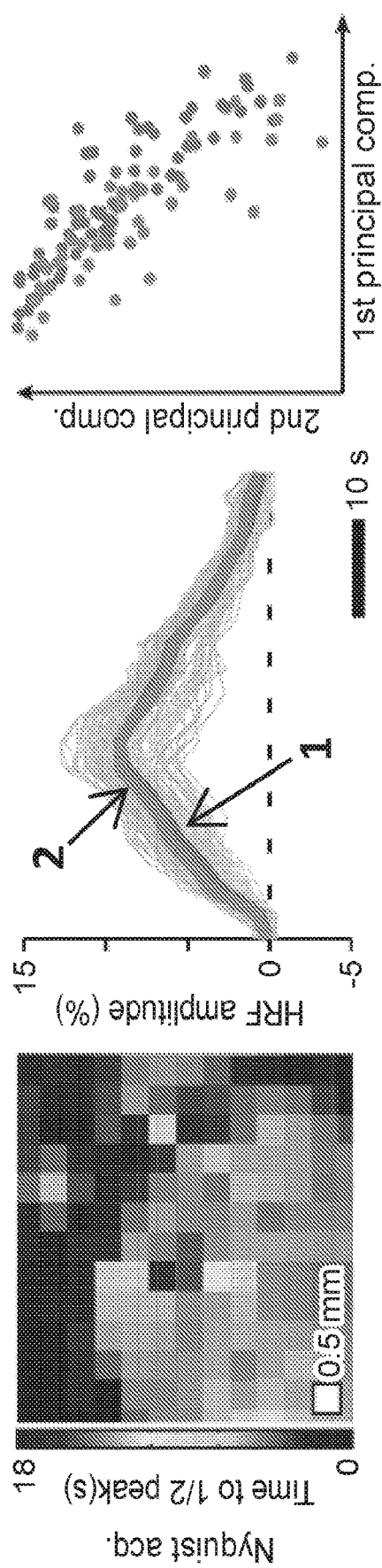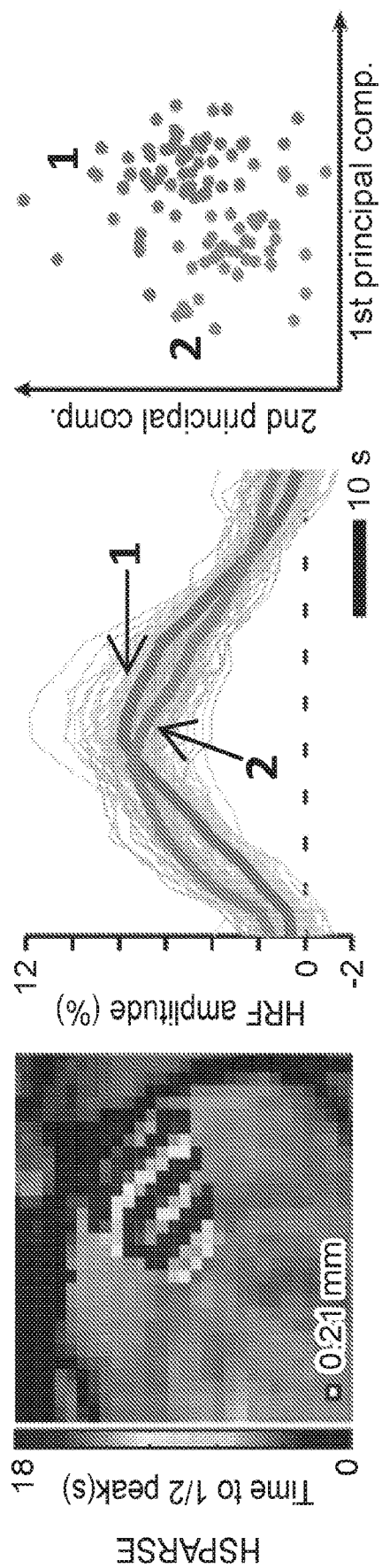

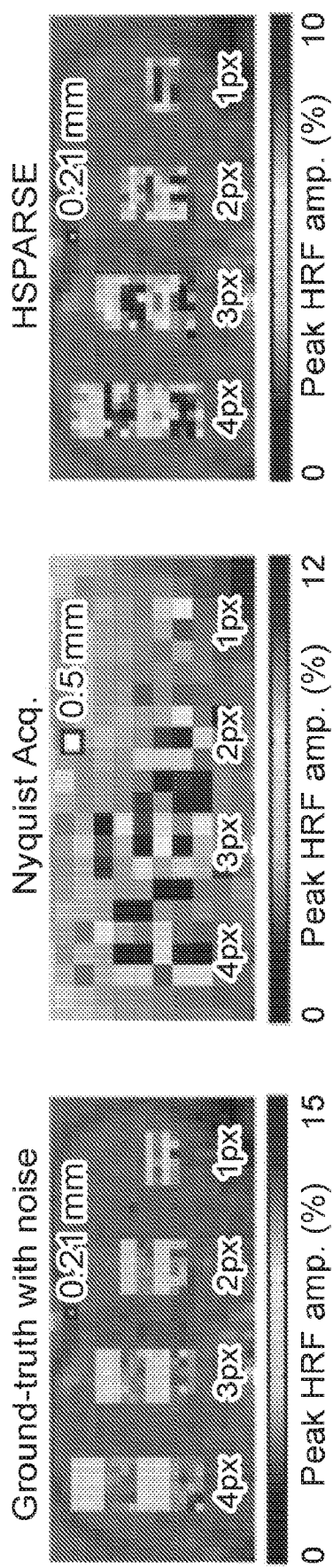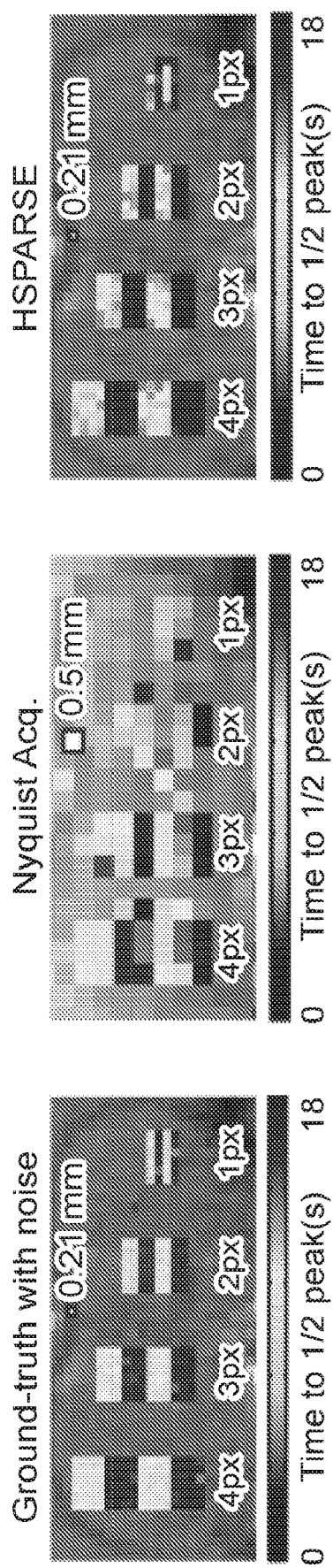

FIG. 9A
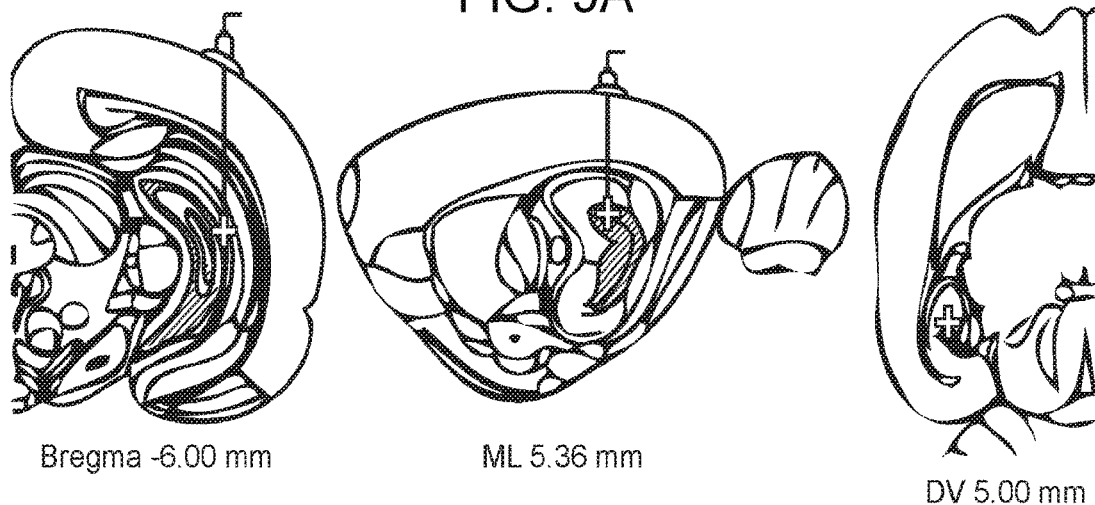
Bregma -6.00 mm    ML 5.36 mm    DV 5.00 mm
FIG. 9B
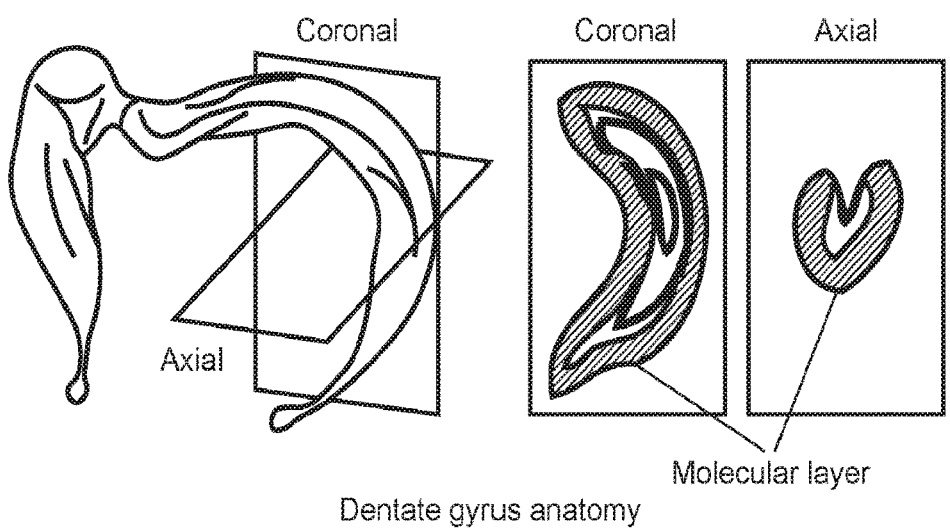
Dentate gyrus anatomy
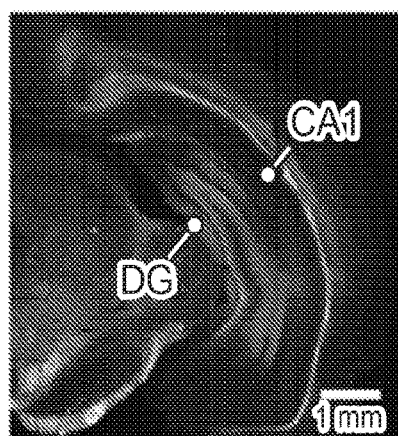
FIG. 9C

FIG. 9E
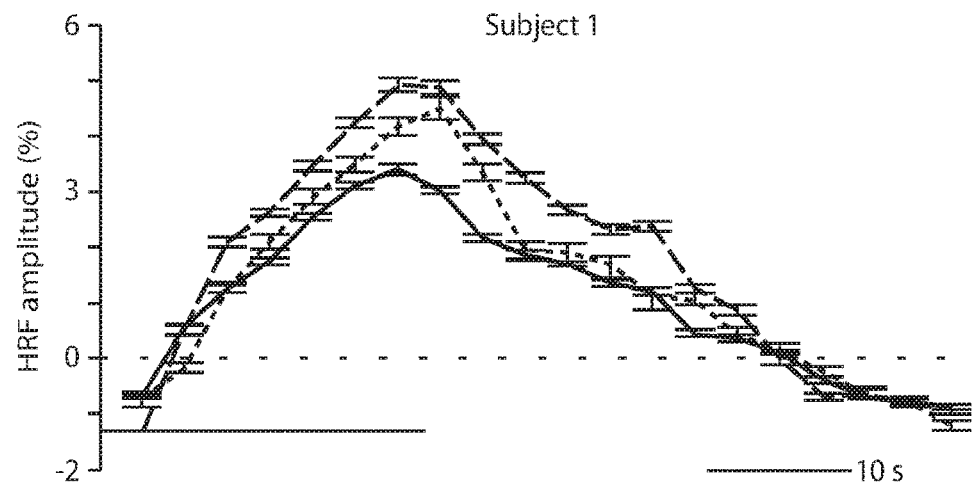
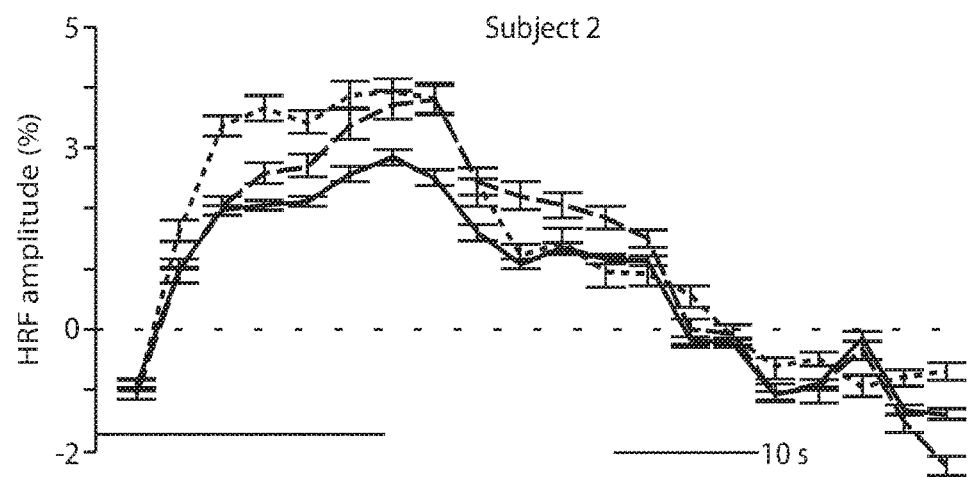
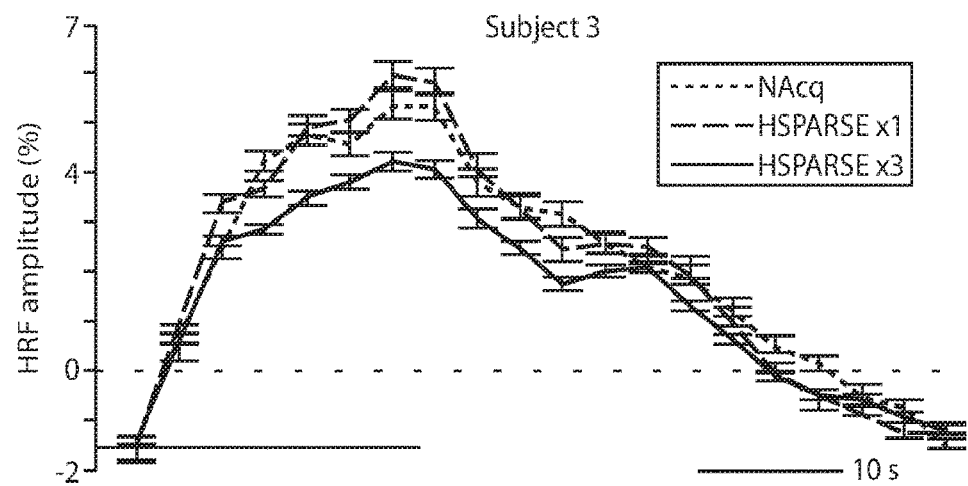

Active volume within design mask

Peak HRF amplitude

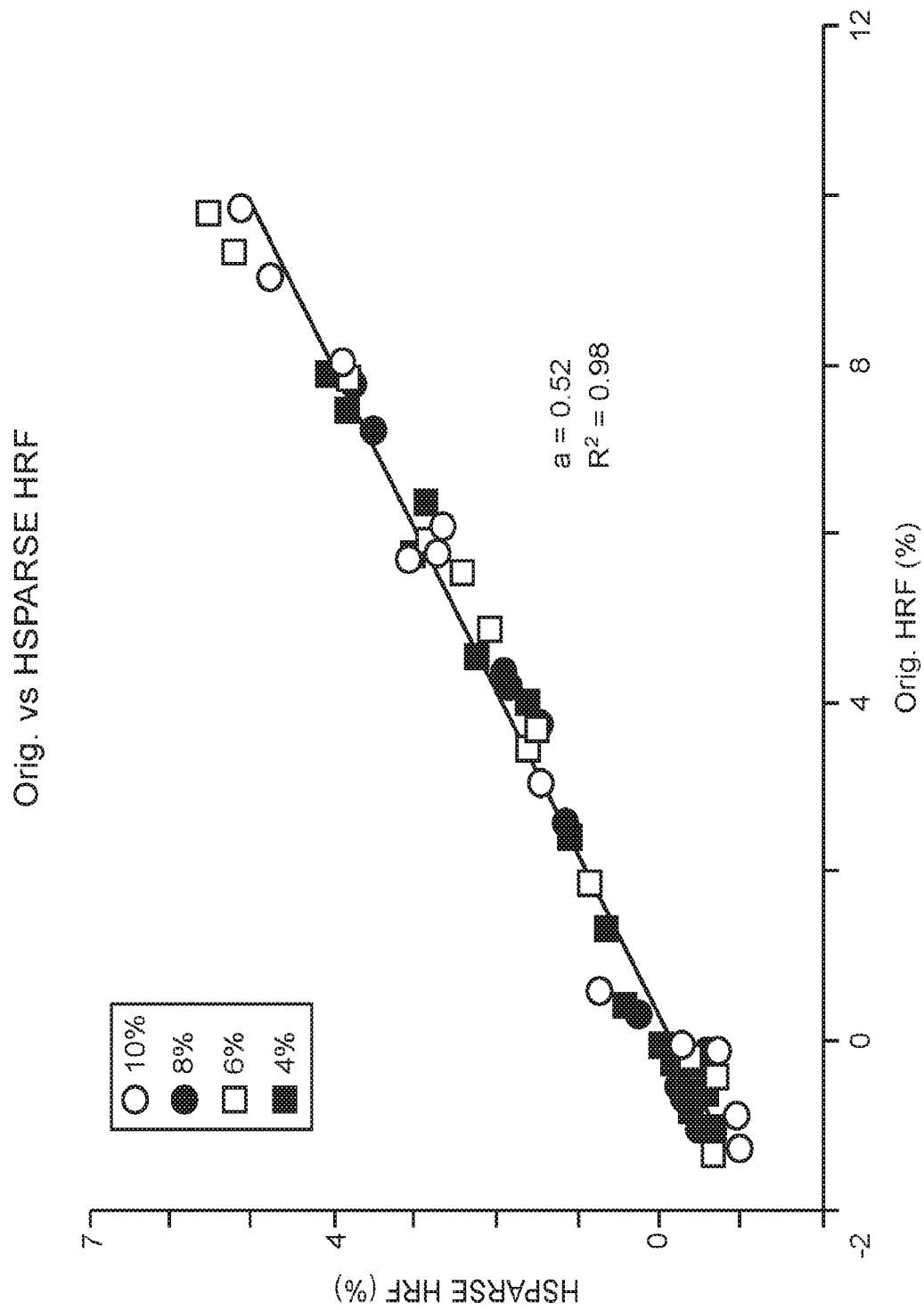

Orig. vs HSPARSE Normalized HRF

Orig. vs HSPARSE duration

Orig. vs HSPARSE time to peak

FIG. 12A
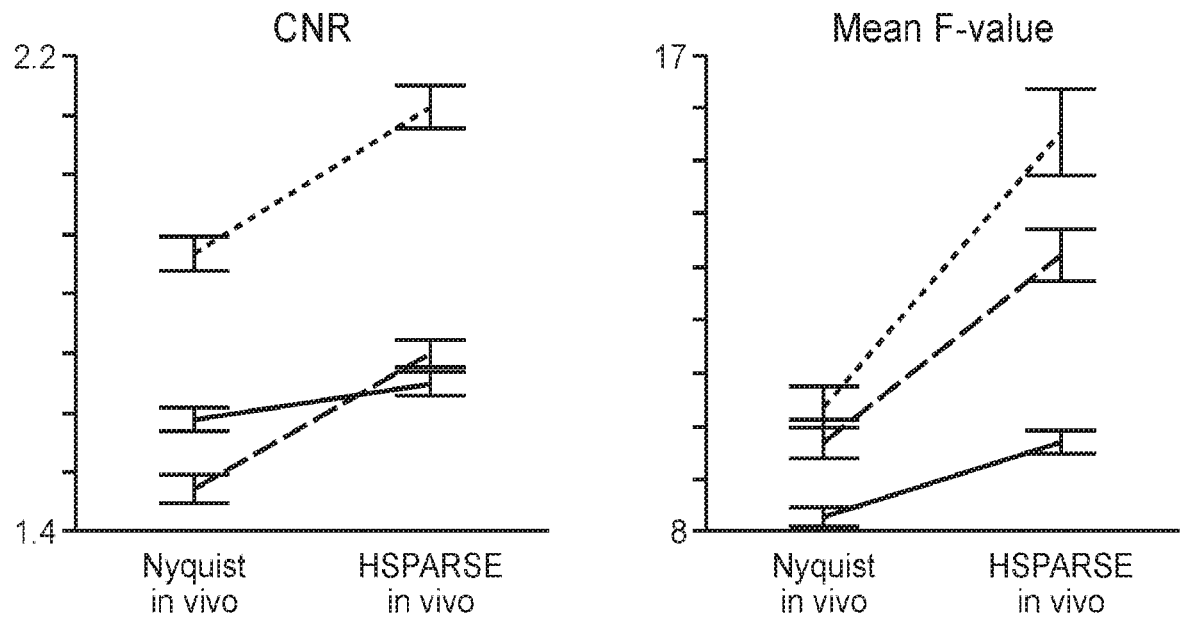
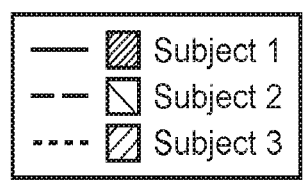
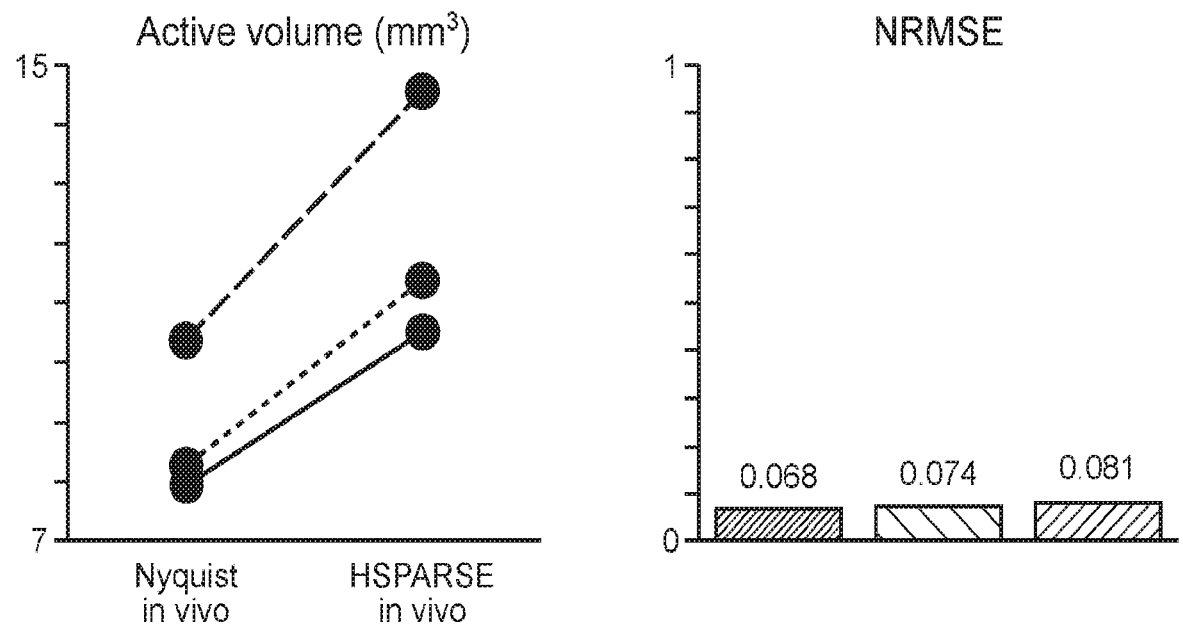

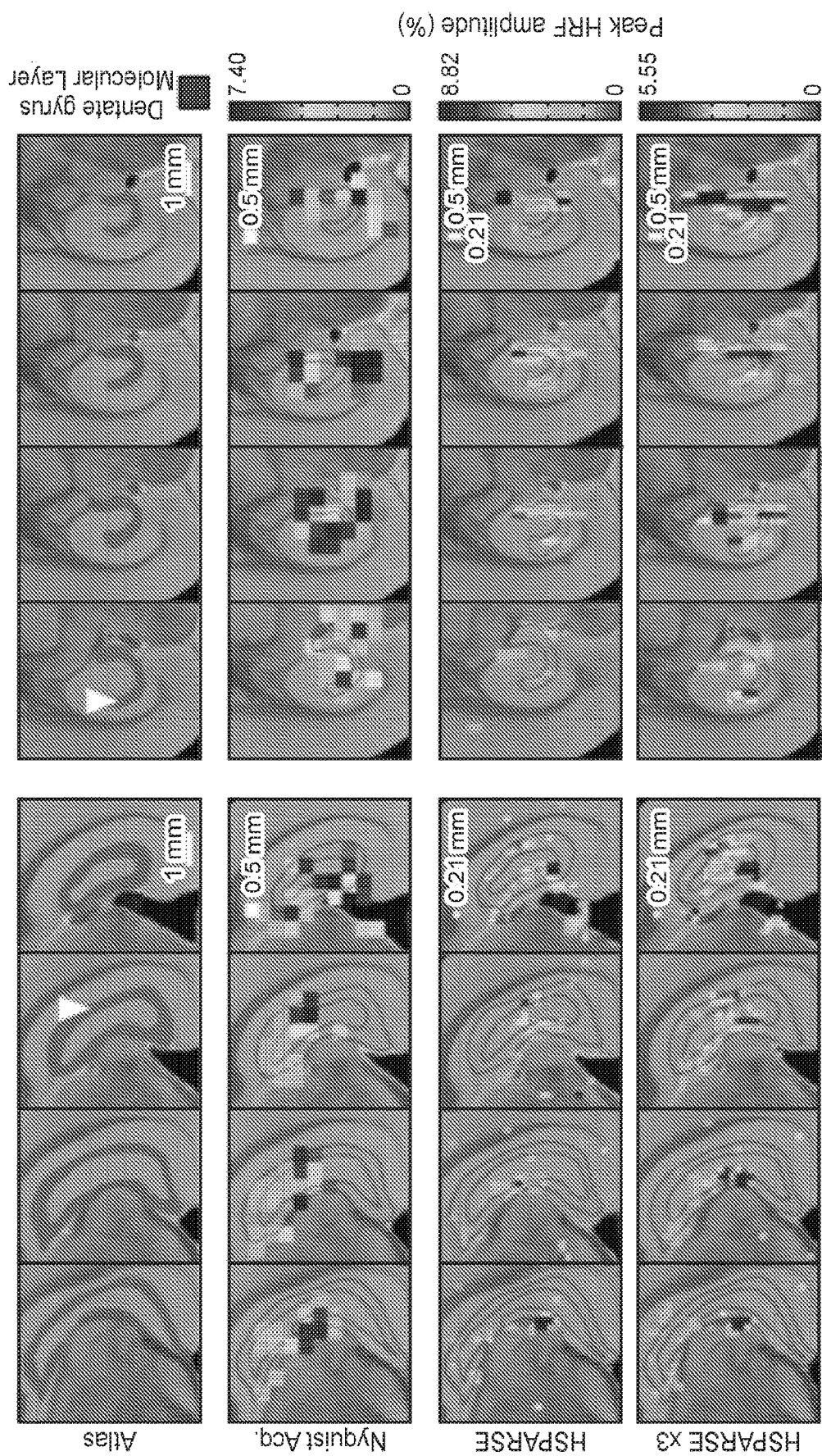

FIG. 16

|  | Time to peak(s) | | | Duration(s) | | |
|---|---|---|---|---|---|---|
|  | NAcq | HSPARSEx1 | HSPARSEx3 | NAcq | HSPARSEx1 | HSPARSEx3 |
| Subject 1 | 24 | 21 | 21 | 23.47 | 32.03 | 26.65 |
| Subject 2 | 21 | 24 | 21 | 23.26 | 32.02 | 33.60 |
| Subject 3 | 24 | 21 | 21 | 34.71 | 33.52 | 34.38 |

FIG. 17

| function / processor | CPU(s) | GPU(s) |
|---|---|---|
| DCT | 188.49 (±0.268) | 1.14 (±6.65x10$^{-3}$) |
| NUFFT | 88.76 (±6.57x10$^{-2}$) | 3.17 (±4.00x10$^{-3}$) |
| iNUFFT | 87.83 (±4.15x10$^{-2}$) | 0.81 (±4.68x10$^{-4}$) |
| One iteration | 1093.80 (±126.67) | 32.06 (±7.66) |
| Full recon | ~ 18 hours | ~ 30 min |

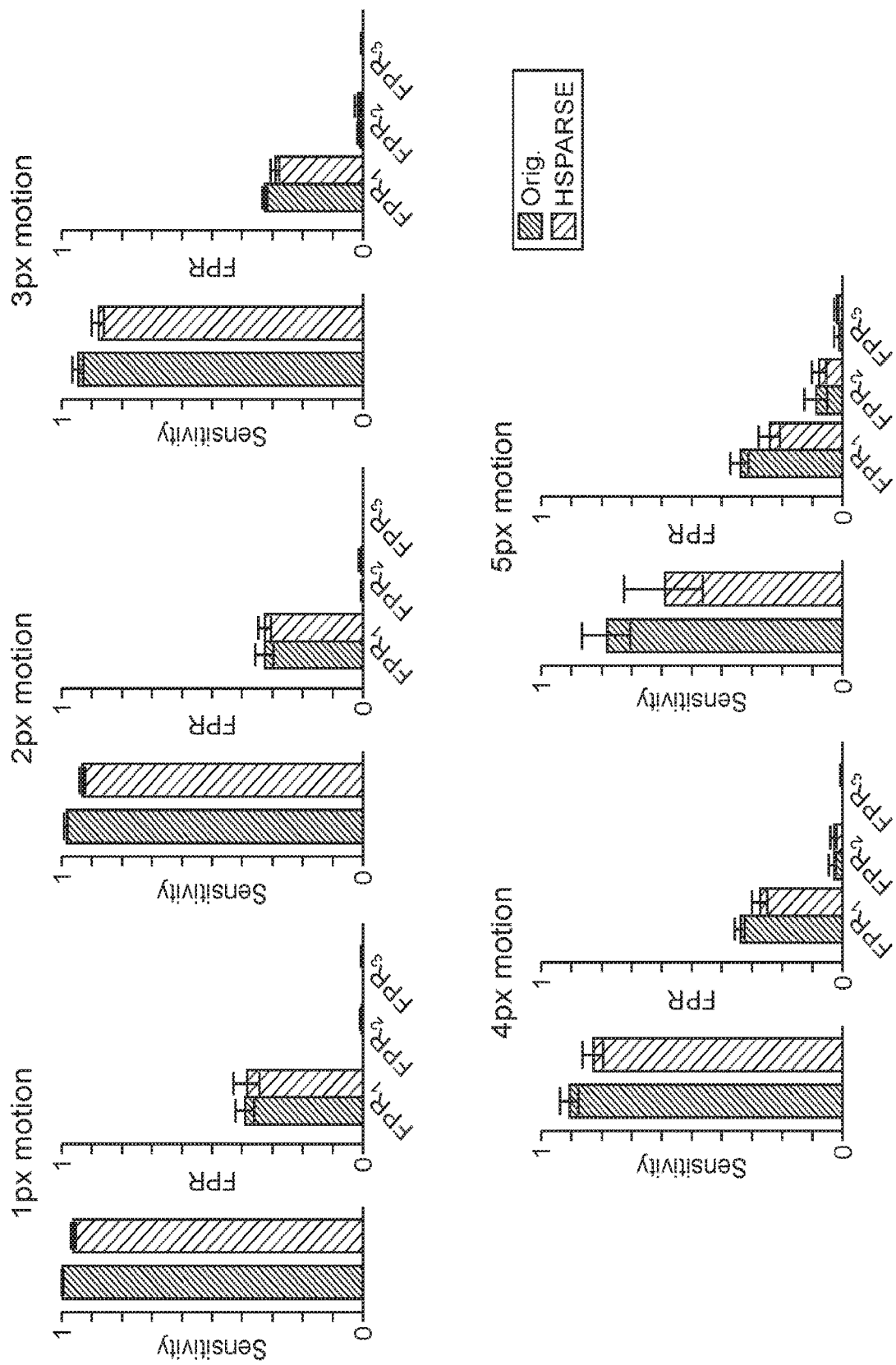

FIG. 19

Algorithm 1 FISTA MRI Reconstruction Algorithm

1:   minimize $f(m) = \frac{1}{2}\|F\Psi_s^* w - b\|_2^2 + \lambda\|w\|_1$

2:

3:   /* Initialization */
4:   $w_{-1} = w_0 = \Psi_s F^* b$
5:   $k = 1$
6:   $t_0 = 1$
7:
8:   /* Optimization loop begins */
9:   while k < maxIter do
10:     $t_k = t_{k-1}$
11:     $y = w_{k-1} + \frac{k-2}{k-1}(w_{k-1} - w_{k-2})$
12:     $w_k = prox_{t_k h}(y - t_k \nabla g(y))$
13:     /* line search */
14:     while $g(w_k) > g(y) + R\langle \nabla g(y)^H (w_k - y)\rangle + \frac{1}{2t_k}\|w_k - y\|_2^2$
15:       $t_k = \beta t_k$
16:       $w_k = prox_{t_k h}(y - t_k \nabla g(y))$
17:     end while
18:     $k = k + 1$
19:   end while
20:
21:   /* End of the optimization */
22:   Return $\Psi_s^* w_k$
23:
24:   /* Definition */
25:   $g(w) = \frac{1}{2}\|F\Psi_s^* w - b\|_2^2$
26:                         $\nabla g(w) = \Psi_s F^* (F\Psi_s^* w - b)$ 27:   $\left(prox_{t_k \lambda h}(y)\right)_i = \begin{cases} (|y_i| - t_k\lambda)\frac{y_i}{|y_i|} & |y_i| \geq t_k\lambda \\ 0 & -t_k\lambda < |y_i| < t_k\lambda \\ (|y_i| + t_k\lambda)\frac{y_i}{|y_i|} & |y_i| \leq t_k\lambda \end{cases}$

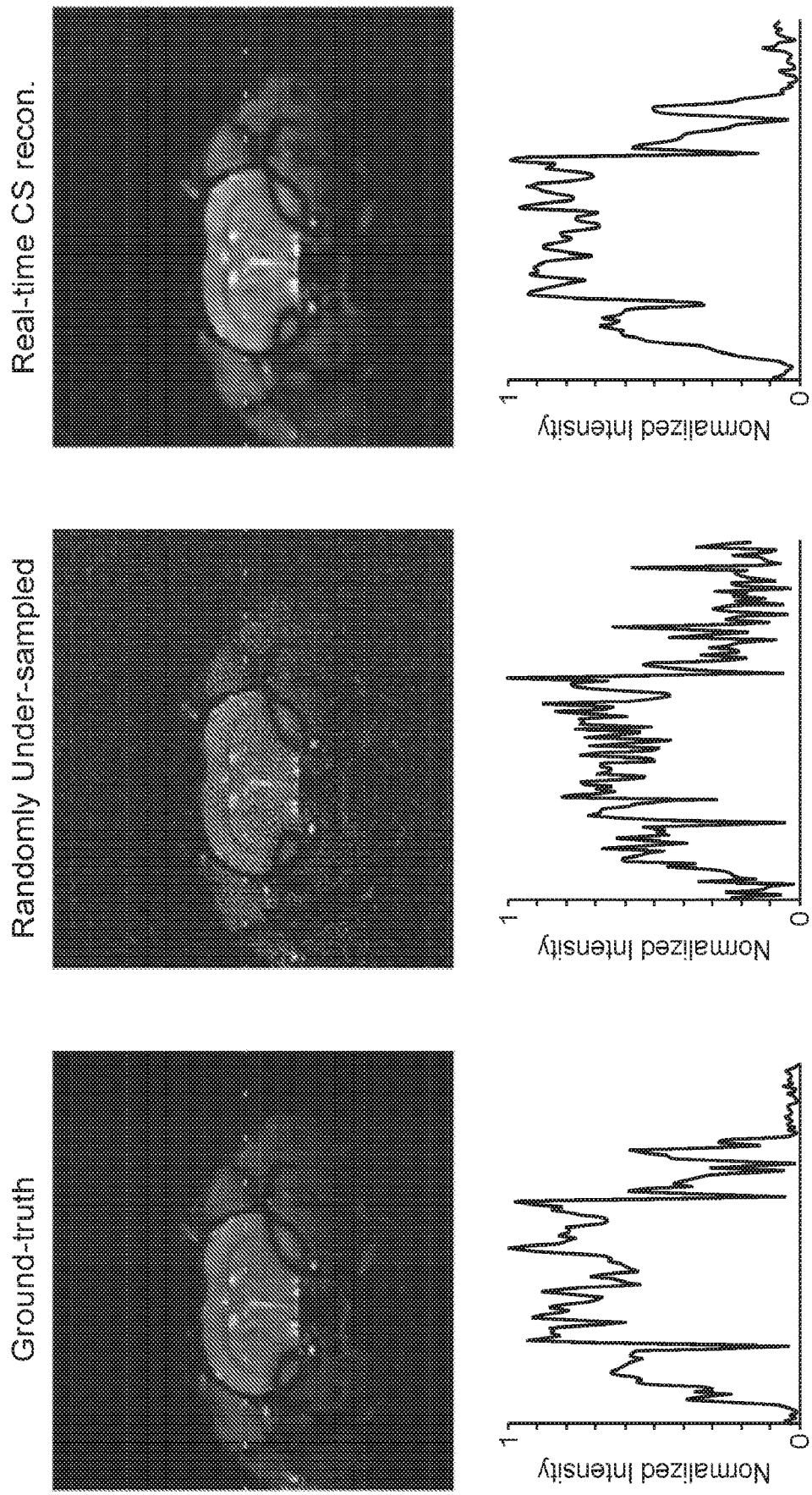

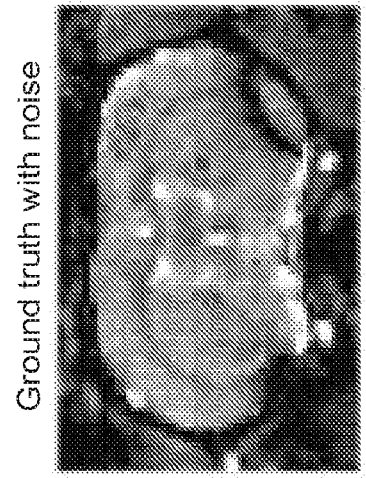
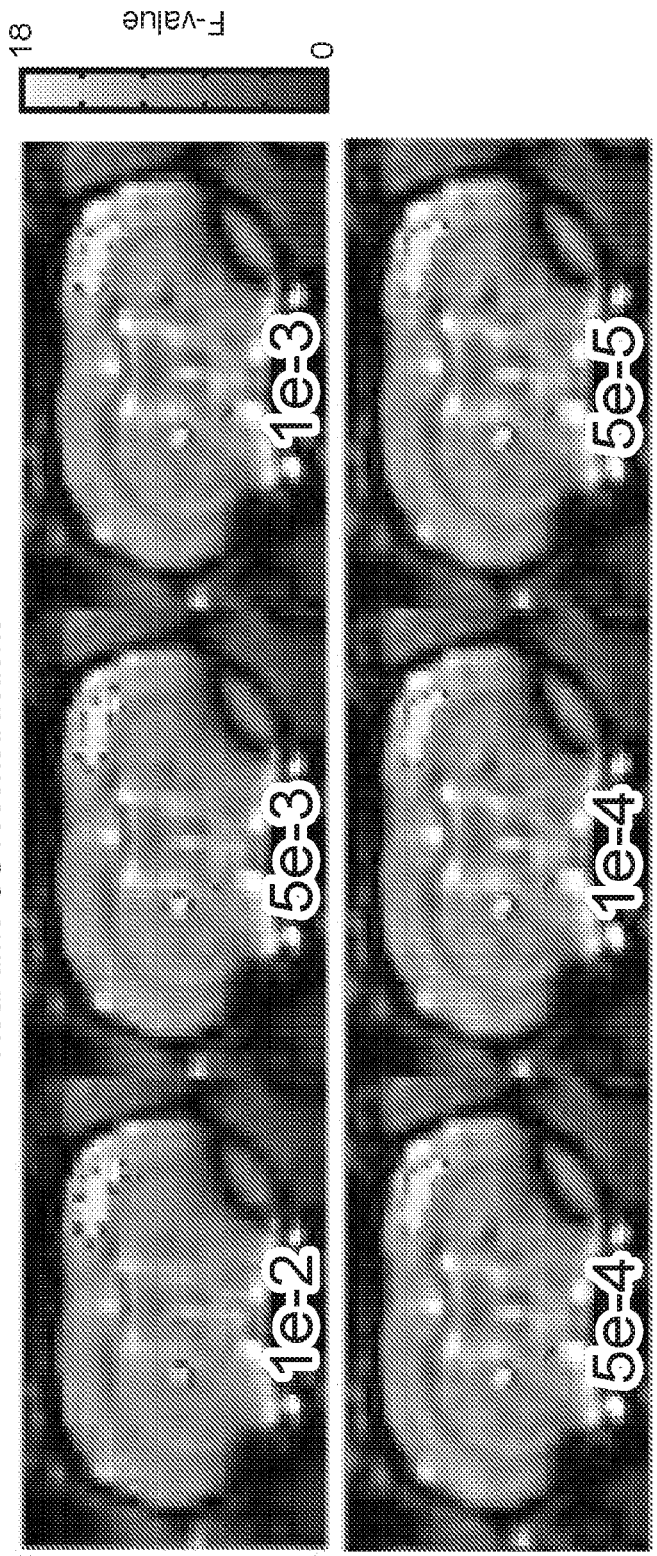
FIG. 22

COMPRESSED SENSING HIGH RESOLUTION FUNCTIONAL MAGNETIC RESONANCE IMAGING

CROSS-REFERENCE TO RELATED APPLICATIONS

This application claims priority pursuant to 35 U.S.C. § 119(e) to the filing date of U.S. Provisional Application No. 62/212,335, filed Aug. 31, 2015, the disclosure of which is incorporated herein by reference.

GOVERNMENT SUPPORT CLAUSE

This invention was made with government support under Grant Number 1460400 awarded by the National Science Foundation. The government has certain rights in the invention.

INTRODUCTION

Functional magnetic resonance imaging (fMRI) has been used in neuroscience research and for clinical applications. However, achieving high spatial resolution remains a significant challenge in fMRI because of a trade-off with decreased temporal resolution and/or lower contrast-to-noise ratio (CNR). High magnetic field systems, improvement of coil sensitivity, advancements in pulse sequences, utilization of parallel imaging, and reconstruction with partial k-space have been used to try to increase spatial resolution. However, demands for even higher spatial resolution are common.

SUMMARY

The present disclosure provides methods and systems for high-resolution functional magnetic resonance imaging (fMRI), including real-time high-resolution fMRI methods and systems.

Aspects of the present disclosure include a method for functional magnetic resonance imaging (fMRI) of a subject. The method includes applying with an MRI system, a balanced steady state free precession (b-SSFP) sequence to a target area in a subject, acquiring with the MRI system, image data of the target area in the subject using a randomly undersampled variable density spiral (VDS) trajectory, and producing an image of the target area in the subject based on the acquired image data.

In some embodiments, the producing comprises analyzing the image data using a spatial sparsifying transform. In some embodiments, the spatial sparsifying transform comprises a discrete cosine transform (DCT).

In some embodiments, the method is a real-time fMRI method. In some embodiments, the producing comprises analyzing the image data using a fast iterative shrinkage thresholding algorithm (FISTA).

In some embodiments, the method has a sampling acceleration factor of 2 or more. In some embodiments, the method has a sampling acceleration factor of 5 or more.

In some embodiments, the method produces an image having a spatial resolution of about 0.2×0.2×0.5 mm$^3$ or greater.

In some embodiments, the method produces an image having a contrast-to-noise ratio of 1.5 or more. In some embodiments, the method produces an image having a contrast-to-noise ratio of 2.5 or more.

Aspects of the present disclosure include a functional magnetic resonance imaging (fMRI) system. The system includes a coil configured to apply a balanced steady state free precession (b-SSFP) sequence to a target area in a subject, a receiver configured to acquire image data of the target area in the subject using a randomly undersampled variable density spiral (VDS) trajectory, and a processor configured to produce an image of the target area in the subject based on the acquired image data.

In some embodiments, the processor is configured to analyze the image data using a spatial sparsifying transform. In some embodiments, the spatial sparsifying transform comprises a discrete cosine transform (DCT).

In some embodiments, the system is configured for real-time fMRI. In some embodiments, the processor is configured to analyze the image data using a fast iterative shrinkage thresholding algorithm (FISTA).

In some embodiments, the system has a sampling acceleration factor of 2 or more. In some embodiments, the system has a sampling acceleration factor of 5 or more.

In some embodiments, the processor produces an image having a spatial resolution of about 0.2×0.2×0.5 mm$^3$ or greater.

In some embodiments, the processor produces an image having a contrast-to-noise ratio of 1.5 or more. In some embodiments, the processor produces an image having a contrast-to-noise ratio of 2.5 or more.

BRIEF DESCRIPTION OF THE DRAWINGS

A randomized, variable-density, under-sampled spiral acquisition scheme was designed for the HSPARSE fMRI.

Separating the spatial and temporal sparsity constraints resulted in higher image contrast, HRF amplitude, and allowed lower noise level and false positive rate. (FIG. 2A-D) The optimized 4D DCT based compressed sensing (CS) reconstruction with regularization parameter of $\lambda = 1e^{-2}$ was first compared with the 3D+1D DCT based method using a phantom. The reconstruction using 3D+1D DCT produced higher mean F-value, image contrast and lower noise level compared to the reconstruction using 4D DCT. Although slightly higher sensitivity was observed in the reconstruction using 4D DCT, the false positive rate of the 4D DCT based method was also much larger than the 3D+1D based method. Furthermore, the reconstruction using 4D DCT also resulted in smoother and lower amplitude HRFs compared to the HRFs reconstructed with the 3D+1D DCT. (FIG. 2E, 2F) Similarly, the 3D+1D method produced higher mean F-value, contrast and lower noise level in an in vivo dataset. (FIG. 2G) The reconstruction using 3D+1D DCT also allowed a higher HRF amplitude, indicating the 3D+1D DCT regularization resulted in less temporal distortion.

Design of the GPU accelerated CS reconstruction algorithm.

FIG. 4: Pre-computation of line search decompositions improved the computational efficiency of the gradient descent method.

Phantoms used for optimization and testing of HSPARSE fMRI.

HSPARSE fMRI method achieved high signal sensitivity and low false positive rate across a wide range of CNRs and phantoms. (FIG. 6A) The fMRI signal sensitivity was defined as the number of true positive (TP) voxels over the number of true positive and false negative (FN) voxels. (FIG. 6B) The false positive rate was defined as the number of false positive (FP) voxels over the number of false positive and true negative (TN) voxels within the 1- to 5-pixel perimeter layers of the designed activation volume (FPR1 to FPR5). (FIG. 6D) Sensitivity and FPR tests were performed on the A2-C2 phantoms with four different peak HRF amplitude of 10-4% (corresponding to CNR of 2.55-1.23). The mean sensitivities of the HSPARSE reconstructed datasets were found to be 69 to 99% of the original sensitivities with noise for all tested peak HRF amplitudes. (FIG. 6E) The mean false positive rates were less than 0.051 on the 1-pixel perimeter layer and less than 0.01 on the 2-pixel perimeter layer. Error bar represents standard error across the A2-C2 phantoms. Taken together, these data show that the optimal HSPARSE reconstruction results in high sensitivity and low FPR.

HSPARSE fMRI method resolved spatially adjacent yet functionally distinct regions. (FIG. 7A, 7D) A rat brain phantom with three layers of distinct peak HRF amplitude/latency in the cortex was designed. HRFs of the three layers and their corresponding principal component decompositions demonstrate clear separation of the three layers. Thicker lines in the HRF plot represent the mean HRF of each layer. (FIG. 7B, 7E) Highest spatial resolution Nyquist acquisition resulted in activity with obscured boundaries between layers. (FIG. 7C, 7F) HSPARSE reconstruction correctly identified the spatial location where the amplitude/time-to-peak transition occurs.

Resolution limit of the HSPARSE fMRI was identified. (FIG. 8A, 8D) A phantom that was challenging to reconstruct with low spatial resolution was designed with an interleaved pattern consisting of distinct peak HRF amplitude/latency features. (FIG. 8B, 8E) The highest spatial resolution Nyquist acquisition completely failed to separate the six interleaved layers. (FIG. 8C, 8F) In contrast, the HSPARSE reconstruction successfully resolved the peak HRF amplitude and latency differences for all six layers. (FIG. 8G, 8H) To identify the resolution limit of the HSPARSE method, a phantom with interleaved activation layers of variable thickness (4·1 pixels or 0.84·0.21 mm) was designed. Layers with distinct peak HRF amplitude/latency can be distinguished down to 3-pixels (0.62 mm) using the Nyquist acquisition and down to a single pixel (0.21 mm) using the HSPARSE method.

HSPARSE fMRI method resolved in vivo layer-specific activity evoked by optogenetic stimulation of dentate gyrus. (FIG. 9A) Schematic showing optogenetic targeting of the dentate gyrus. (FIG. 9B) Dentate gyrus had a unique horn shape, with its coronal and axial slices showing "O" and "U" shaped profiles, respectively. (FIG. 9C) Histological examination verified that the ChR2-EYFP expression was localized to the dentate gyrus region. (FIG. 9E, 9F) As was seen with the simulations, the HSPARSE-reconstructed HRF amplitudes at the stimulation site were lower than their respective low-resolution scans. However, the HRFs were strongly correlated between the HSPARSE reconstructed and Nyquist sampled images, which indicated that in vivo HSPARSE fMRI maintained the temporal characteristics of in vivo HRFs.

Optimal range of CS regularization parameters were identified based on quantitative assessments of the reconstructed images.

HSPARSE reconstruction using optimal regularization parameters maintained HRF temporal characteristics over a range of physiologically relevant HRF amplitudes. (FIG. 11C) The correlation analysis indicated that the HSPARSE reconstructed HRF time courses had strong linear correlation to the original HRFs (slope=0.52, R2=0.98).

HSPARSE fMRI method was robust against real physiological noise. (FIG. 12A) The HSPARSE fMRI also improved the CNR, maximum correlation coefficient, and active volume compared to their corresponding fully-sampled datasets in the presence of real physiological noise. The NRMSE values were less than 0.081 across all subjects. Error bars represent the standard error across voxels of the active area for CNR and maximum correlation coefficient.

Six-cycle time-series and analysis results corresponding to the main Figures.

FIG. 15A, 15B: Optimized HSPARSE fMRI method consistently resolved layer-specific activity of the dentate gyrus upon optogenetic stimulation. Two additional in vivo experiment results were shown. With the highest spatial resolution Nyquist rate sampled images, activity was observed throughout the hippocampus. In contrast, activities in the HSPARSE reconstructed images were confined to the dentate gyrus. The peak amplitude activities followed the geometry of the molecular layer for all three subjects. The pink area and the red lines delineate the dentate gyrus. The white arrow indicates the site of stimulation.

FIG. 16: Comparison of temporal characteristics of HRF between HSPARSE fMRI and Nyquist acquisition fMRI following optogenetic stimulation of the dentate gyrus. Three subjects were optogenetically stimulated during imaging, using the single (HSPARSE HSPARSE×1) and 3 times averaged (HSPARSE×3) high-resolution HSPARSE fMRI and a highest spatial resolution Nyquist acquisition (NAcq). For each subjects, the time-to-peak difference between the HSPARSE and NAcq images was less than the 3 s temporal resolution. Although the duration of activity was similar between the HSPARSE and NAcq images for subject 1 and 3 on average, the duration was larger in the HSPARSE reconstructed image for subject 2. This difference could be due biological variability since the Nyquist acquisition datasets and the CS datasets were separately acquired in different fMRI imaging sessions.

FIG. 17: GPU based HSPARSE fMRI method achieved a 34-fold improvement in speed. Three computationally expensive functions—the DCT, NUFFT and iNUFFT—were tested with the GPU method and its parallel CPU counterpart. The GPU methods showed 165-, 28-, and 108-fold improvements in speed, respectively, resulting in a 34-fold overall speedup.

The HSPARSE fMRI method was robust to motion within a normal physiological range. (FIG. 18C, 18D) When the amount of motion was less than 3-pixels, the HSPARSE reconstructed images were similar to the original image as measured by the mean F-value, sensitivity and false positive rate. However, when motion was larger than 4-pixels, the HSPARSE reconstructed images exhibited decrease in mean F-value and sensitivity.

FIG. 19: Algorithm 1 was implemented on a Graphical Processing Unit platform. Several repeatedly computations such as the non-uniform FFT (NUFFT), inverse NUFFT, DWT and inverse DWT were carefully optimized. For the NUFFT, a similar pre-sorting algorithm was implemented. A custom build workstation was used for the real-time reconstruction with Intel quad-core 2.66 GHz CPU, Nvidia 2048 cores CUDA GPU and 16 GB CPU memory.

High reconstruction speed was achieved with FISTA method and GPU optimization.

FIG. 21: Optimized stack of VDS achieved high incoherent sampling and FISTA method successfully reconstructs the under-sampled image. The normalized image intensities are also shown across the yellow dashed line.

Figure 1A:
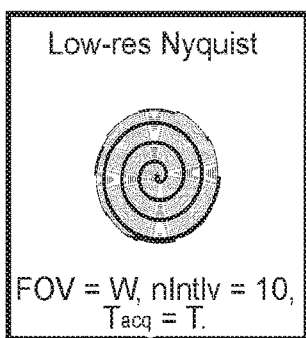
(FIG. 1A) A low spatial resolution Nyquist trajectory only covers a small range of k-space.

Real-time high-resolution CS fMRI resolves layer specific activity. Two different types of HRFs with distinct peak HRF amplitude (FIG. 23A) and latency (FIG. 23B) were added into a phantom with interleaved layer pattern. The real-time high-resolution CS fMRI method successfully resolves the peak HRF amplitude and latency differences between the two layers while the highest spatial resolution Nyquist acquisition failed.

Randomized variable density stack of spirals design. (FIG. 24A) The center k-space is designed to have a higher density than the outer k-space. Incoherence is introduced by randomly disturb the angle of each interleaf and random skipping interleaves in the outer k-space. (FIG. 24B) The effective field of view of the spiral trajectory is designed to follow a series of exponential functions shown.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an opsin" includes a plurality of such opsins and reference to "the carbon fiber" includes reference to one or more carbon fibers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods and systems for high-resolution functional magnetic resonance imaging (fMRI), including real-time high-resolution fMRI methods and systems.

In describing embodiments of the present disclosure, methods for high-resolution functional magnetic resonance imaging (fMRI) are first described, followed by a description of systems useful for performing the subject methods.

Methods

Aspects of the present disclosure include a method for functional magnetic resonance imaging (fMRI) of a subject. In certain embodiments, the method is a compressed sensing (CS) high-resolution fMRI method. Compressed sensing refers to a signal processing method where an image can be reconstructed from a series of sampling measurements obtained with a sampling rate below the Nyquist sampling rate. In general, the method may include obtaining one or more fMRI images of a target area in a subject. For instance, in general, the method may include applying with an MRI system (e.g., a permanent magnet or electromagnet of the MRI system) a magnetic field to a target area in a subject. In some instances, the method also includes applying with the MRI system (e.g., an RF coil of the MRI system) an excitation waveform (e.g., an RF excitation waveform) to the target area in the subject to produce detectable image data (e.g., magnetic resonance (MR) signals) of the target area in the subject. One or more additional fields may also be applied by the MRI system, such as, but not limited to, one or more shim fields using one or more shim coils, one or more gradient fields using one or more gradient coils, and the like. In addition, the method includes acquiring the image data (e.g., with a receiver of the MRI system) and producing an image of the target area in the subject based on the acquired image data.

The acquired image data may be saved in a computer-readable memory and analyzed at a subsequent time (also referred to herein as "offline" processing or "offline" MRI). In other cases, the acquired image data may be analyzed in real-time to produce the image of the target area in the subject. By "real-time" is meant that the acquired signals are analyzed by the MRI system (e.g., by a processor in the MRI system) immediately after signal acquisition and/or during signal acquisition.

In certain embodiments of offline fMRI, to produce the MR image data, the method may include applying an excitation waveform to the target area in the subject. In certain embodiments, the method includes applying a pulse sequence to the target area in the subject. The pulse sequence may be a balanced steady state free precession (b-SSFP) sequence that is applied to the target area in the subject. In certain cases, the pulse sequence has an echo time (TE) of 50 ms or less, such as 40 ms or less, or 30 ms or less, or 20 ms or less, or 10 ms or less, or 5 ms or less, or 3 ms or less, or 2 ms or less. In some instances, the pulse sequence has a TE of 2 ms. In certain cases, the pulse sequence has a repetition time (TR) of 500 ms or less, such as 400 ms or less, or 300 ms or less, or 200 ms or less, or 100 ms or less, or 50 ms or less, or 25 ms or less, or 20 ms or less, or 10 ms or less, or 5 ms or less. In some instances, the pulse sequence has a TR ranging from 5 to 10 ms, such as from 7 to 10 ms, or from 8 to 10 ms, or from 9 to 10 ms. In certain instances, the pulse sequence has a TR of 9.375 ms.

In some instances of offline MRI, the method includes acquiring image data (MR signals) of the target area in the subject. In certain cases, the method includes using a sampling trajectory. The sampling trajectory may be a randomized sampling trajectory. For instance, the method may include acquiring image data of the target area in the subject using a randomly undersampled trajectory, such as a randomly undersampled variable density spiral (VDS) trajectory. In certain cases, the sampling trajectory is a variable density spiral (VDS) trajectory, such as, for example, a randomized under-sampling stack of multi-interleaf variable density spiral (VDS) trajectory. In certain instances, the total number of interleaves at each kz-slice follows a Laplacian distribution. For instance, in some embodiments, the center k-space is more densely sampled than the outer k-space.

In certain embodiments of offline MRI, the sampling method has a field of view (FOV). For example, the sampling method may have a FOV of 10×10×10 mm or more, such as 15×15×15 mm or more, or 20×20×15 mm or more, or 25×25×15 mm or more, or 30×30×15 mm or more, or 35×35×15 mm or more. In certain instances, the sampling method has a FOV of 35×35×16 mm In some cases, the sampling method has a resolution of 1×1×1 mm or less, such as 0.75×0.75×0.75 mm or less, or 0.5×0.5×0.5 mm or less, or 0.25×0.25×0.5 mm or less. In certain instances, the sampling method has a resolution of 0.21×0.21×0.5 mm In certain embodiments, the sampling method achieves a sampling acceleration factor of 2 or more, such as 3 or more, 4 or more, 5 or more, 6 or more, 7 or more, 8 or more, 9 or more, or 10 or more as compared to conventional fMRI. In some cases, the sampling method achieves a sampling acceleration factor of 2 or more. In some cases, the sampling method achieves a sampling acceleration factor of 5 or more.

In certain embodiments of offline MRI, the method includes producing an image of the target area in the subject based on the acquired image data. For example, the method may include analyzing (also referred to herein as processing) the image data to produce the image of the target area. As such, in some instances, the method includes reconstructing an image from the acquired image data. In certain cases, the method includes reconstructing the image using a cost function, such as an L1 regularized cost function. In certain instances, the method includes analyzing/processing the image data using a spatial sparsifying transform, such as a discrete cosine transform (DCT). For instance, the method may include regularizing the fMRI temporal domain using a DCT. In some cases, the method includes regularizing the fMRI spatial domain using a DCT. In some embodiments, the method includes regularizing both the temporal domain and the spatial domain using a DCT.

In certain embodiments of offline fMRI, the method includes reconstructing the image using one or more regularization parameters. Regularization parameters of interest for offline fMRI processing include, but are not limited to, contrast to noise ratio (CNR), active volume within the designed active region, mean F statistic value (mean F-value), normalized root mean squared error (NRMSE), and peak hemodynamic response function (HRF) amplitude. In certain instances, a set of regularization parameters is considered to be in an optimal range if the CNR, active volume within the designed mask, and mean F-value are greater than that of the ground-truth, and its NRMSE is less than 105% of the minimum NRMSE found within the search range. For example, the subject fMRI methods may produce images having a CNR of 1.5 or more, such as 2 or more, or 2.5 or more, or 3 or more, or 4 or more, or 5 or more, or 6 or more, or 7 or more, or 8 or more, or 9 or more, or 10 or more. In some cases, the subject fMRI methods may produce images having a CNR of 1.5 or more. In some cases, the subject fMRI methods may produce images having a CNR of 2.5 or more.

In certain embodiments, the subject fMRI methods produce an image having a spatial resolution of about $0.2 \times 0.2 \times 0.5$ mm$^3$ or greater. For example, the subject fMRI methods can produce images having a spatial resolution of $1 \times 1 \times 1$ mm$^3$ or greater, such as $0.9 \times 0.9 \times 0.9$ mm$^3$ or greater, or $0.8 \times 0.8 \times 0.8$ mm$^3$ or greater, or $0.7 \times 0.7 \times 0.7$ mm$^3$ or greater, or $0.6 \times 0.6 \times 0.6$ mm$^3$ or greater, or $0.5 \times 0.5 \times 0.5$ mm$^3$ or greater, or $0.4 \times 0.4 \times 0.5$ mm$^3$ or greater, or $0.3 \times 0.3 \times 0.5$ mm$^3$ or greater, or $0.2 \times 0.2 \times 0.5$ mm$^3$ or greater, or $0.1 \times 0.1 \times 0.5$ mm$^3$ or greater. In certain instances, the subject fMRI methods produce an image having a spatial resolution of $0.21 \times 0.21 \times 0.5$ mm$^3$. In certain instances, the subject fMRI methods produce an image having a spatial resolution ranging from $0.1 \times 0.1 \times 0.5$ mm$^3$ to $1 \times 1 \times 1$ mm$^3$, such as from $0.1 \times 0.1 \times 0.5$ mm$^3$ to $0.9 \times 0.9 \times 0.9$ mm$^3$, or from $0.1 \times 0.1 \times 0.5$ mm$^3$ to $0.8 \times 0.8 \times 0.8$ mm$^3$, or from $0.1 \times 0.1 \times 0.5$ mm$^3$ to $0.7 \times 0.7 \times 0.7$ mm$^3$, or from $0.1 \times 0.1 \times 0.5$ mm$^3$ to $0.6 \times 0.6 \times 0.6$ mm$^3$, or from $0.1 \times 0.1 \times 0.5$ mm$^3$ to $0.5 \times 0.5 \times 0.5$ mm$^3$, or from $0.1 \times 0.1 \times 0.5$ mm$^3$ to $0.4 \times 0.4 \times 0.5$ mm$^3$, or from $0.1 \times 0.1 \times 0.5$ mm$^3$ to $0.3 \times 0.3 \times 0.5$ mm$^3$. In certain embodiments, the subject fMRI methods produce an image having a spatial resolution ranging from $0.1 \times 0.1 \times 0.5$ mm$^3$ to $0.3 \times 0.3 \times 0.5$ mm$^3$.

As described above, rather than offline processing of the MRI image data, the acquired image data can be processed in real-time.

In certain embodiments of real-time fMRI, to produce the MR image data, the method may include applying an excitation waveform to the target area in the subject. In certain embodiments, the method includes applying a pulse sequence to the target area in the subject to produce image data (MR signals) that can be acquired by the MRI system. As such, in some instances, the method includes acquiring the image data (MR signals) of the target area in the subject. In certain cases, the method includes using a sampling trajectory. The sampling trajectory may be a randomized sampling trajectory. For instance, the method may include acquiring image data of the target area in the subject using a randomly undersampled trajectory, such as a randomly undersampled variable density spiral (VDS) trajectory. In certain cases, the sampling trajectory is a variable density spiral (VDS) trajectory, such as, for example, a randomized stack of variable density spiral (VDS) trajectory. In certain instances, the sampling density follows an exponential function along the kx and ky plane, and the variance of the exponential function decreases along the kz direction. In some instances, randomness is introduced into the sampling for CS reconstruction by randomly perturbing the angle of each spiral interleaf. In certain cases, the trajectory has a slightly larger total number of interleaves, and interleaves on the outer k-space are randomly skipped following a Gaussian distribution to achieve the desired temporal resolution. In some instances, the kz-slice location may be adjusted to achieve variable density sampling in the kz dimension and high spatial resolution in the z dimension.

In certain embodiments of real-time MRI, the sampling method has a field of view (FOV). For example, the sampling method may have a FOV of $10 \times 10 \times 10$ mm or more, such as $15 \times 15 \times 15$ mm or more, or $20 \times 20 \times 15$ mm or more, or $25 \times 25 \times 15$ mm or more, or $30 \times 30 \times 15$ mm or more, or $35 \times 35 \times 15$ mm or more. In certain instances, the sampling method has a FOV of $35 \times 35 \times 16$ mm In some cases, the sampling method has a resolution of $1 \times 1 \times 1$ mm or less, such as $0.75 \times 0.75 \times 0.75$ mm or less, or $0.5 \times 0.5 \times 0.5$ mm or less, or $0.25 \times 0.25 \times 0.5$ mm or less. In certain instances, the sampling method has a resolution of $0.25 \times 0.25 \times 0.5$ mm In certain embodiments, the sampling method achieves a sampling acceleration factor of 2 or more, such as 3 or more, 4 or more, 5 or more, 6 or more, 7 or more, 8 or more, 9 or more, or 10 or more as compared to conventional fMRI. In some cases, the sampling method achieves a sampling acceleration factor of 2 or more. In some cases, the sampling method achieves a sampling acceleration factor of 5 or more.

In certain embodiments of real-time MRI, the method includes producing an image of the target area in the subject based on the acquired image data. For example, the method may include analyzing (also referred to herein as processing) the image data to produce the image of the target area. As described herein, the image data may be processed in real-time to produce the image of the target area. As such, in some instances, the method includes reconstructing an image from the acquired image data in real-time. In certain cases, the method includes reconstructing the image using a cost function, such as an L1 spatial regularized cost function. In certain instances, the method includes analyzing/processing the image data using a sparsifying transform, such as a Daubechies 4 wavelet. In some cases, the method includes analyzing/processing the image data using a fast iterative shrinkage thresholding algorithm (FISTA).

In certain embodiments of real-time fMRI, the method includes reconstructing the image using one or more regularization parameters. Regularization parameters of interest for real-time fMRI processing include, but are not limited to, contrast to noise ratio (CNR), mean F statistic value (mean F-value), normalized root mean squared error (NRMSE), peak HRF amplitude, sensitivity, and false positive rate in the reconstructed dataset. In certain instances, a set of regularization parameters is considered to be in an optimal range if the parameters give top 50% CNR, mean F-value, sensitivity, and bottom 50% NRMSE and false positive rate. For example, the subject fMRI methods may produce images having a CNR of 1.5 or more, such as 2 or more, or 2.5 or more, or 3 or more, or 4 or more, or 5 or more, or 6 or more, or 7 or more, or 8 or more, or 9 or more, or 10 or more. In some cases, the subject fMRI methods may produce images having a CNR of 1.5 or more. In some cases, the subject fMRI methods may produce images having a CNR of 2.5 or more.

In certain embodiments of the present disclosure, the method is a method for functional MRI (fMRI). For example, in general, the present disclosure provides a method for monitoring activity in an organ or tissue of an individual (also referred to as "a subject" herein). In some instances, the target organ or tissue is an excitable organ or tissue in the subject. "Excitable," as used herein, refers to electrically excitable cells in an organ or tissue, such as neurons and muscle cells. Excitable cells typically use changes in their membrane potential to transmit signals within the cell. Thus, an excitable cell may be characterized in having a resting state, where the membrane potential is at the resting membrane potential, and an excited state, where rapid depolarization of the membrane potential is transmitted across the cell as an action potential. The "cellular electrical activity" of an excitable cell may refer to the changes in the membrane potential or may refer to any indirect measure of the changes in membrane potential, such as the changes in intracellular calcium concentration or any other biochemical changes that is a functional measure of the change in the membrane potential.

In certain embodiments, the method includes surgically implanting a device of the present disclosure into or adjacent to an organ or tissue of an individual, and monitoring the activity of the organ or tissue using fMRI. In some cases, surgically implanting the device includes opening an access in the subject and inserting at least a portion of the device through the access. The access may be an access through the skin, bone, muscle, and/or other tissues of the subject. For instance, an access may include an access through bone (e.g., skull) of the subject to allow placement of at least a portion of the device (e.g., an optrode) adjacent to target neurons in the subject.

As indicated above, embodiments of the method include monitoring the activity of the organ or tissue. In some instances, monitoring the activity of the organ or tissue includes conducting functional magnetic resonance imaging (fMRI) on the organ or tissue. In some cases, the organ or tissue includes excitable cells (e.g., cells that express one or more light-responsive polypeptides). The terms "light-activated" and "light-responsive" in reference to a polypeptide or protein that is light-responsive, are used interchangeably and include light-responsive ion channels or opsins, and ion pumps as described herein. Such light-responsive proteins may have a depolarizing or hyperpolarizing effect on the cell on whose plasma membrane the protein is expressed depending on the ion permeability of the activated protein, and the electrochemical gradients present across the plasma membrane.

In some cases, the one or more light-responsive polypeptides include a hyperpolarizing light-responsive polypeptide. In some cases, the one or more light-responsive polypeptides include a depolarizing light-responsive polypeptide. As such, in some cases the method includes producing an image of the target organ or tissue using fMRI.

In some cases, fMRI may be used to image the organ or tissue prior to delivering light to the target organ or tissue using the optrode. In some cases, fMRI may be used to image the organ or tissue during delivery of light to the target organ or tissue using the optrode. In some cases, fMRI may be used to image the organ or tissue after delivering light to the target organ or tissue using the optrode.

The method may further include detecting and/or recording a detectable parameter of the organ or tissue using the device (e.g., optrode). The optrode may be configured to detect electrical signals, such as local field potentials produced by changes in the membrane potential of the excitable cells. Thus, in some cases, the method includes detecting and/or recording a detectable parameter of the organ or tissue using a carbon fiber electrode of the optrode.

The device (e.g., optrode) may include a light source. In these embodiments, the method includes delivering light to the target organ or tissue using the light source. For instance, the method may include stimulating the excitable cells in the target organ or tissue with light from the light source. In some cases, the light source includes an optical fiber as described herein. As such, in these embodiments, the method includes delivering light to the target organ or tissue using the optical fiber (e.g., stimulating the excitable cells with light delivered by the optical fiber). In some cases, the light source includes a laser. As such, in some embodiments, the method includes delivering light to the target organ or tissue using the laser. For example, the method may include generating light using the laser and directing the light from the laser to the target organ or tissue using the optical fiber (e.g., for stimulating the excitable cells in the target organ or tissue with light from the laser). In some cases, the light source includes a light-emitting diode (LED). As such, in some embodiments, the method includes delivering light to the target organ or tissue using the LED. For instance, the method may include generating light using the LED and directing the light from the LED to the target organ or tissue using the optical fiber (e.g., for stimulating the excitable cells in the target organ or tissue with light from the LED).

In certain embodiments, the detectable parameter of the target organ or tissue includes local field potentials, e.g., local field potentials produced by changes in the membrane potential of the excitable cells. The local field potentials may be produced by stimulating the excitable cells with light from the light source. In some instances, the detectable parameter is a single-unit activity, e.g., detectable activity from a single target area (i.e., a uniplex assay). In some cases, the detectable parameter is a multi-unit activity, e.g., detectable activity from two or more target areas (i.e., a multiplex assay).

In some instances, monitoring the activity of the organ or tissue is performed once. In other cases, monitoring the activity of the organ or tissue is performed two or more times. In some cases, monitoring the activity of the organ or tissue is performed several times over a period of time, e.g., the method includes chronically monitoring the activity of the organ or tissue. In some cases, monitoring the activity of the organ or tissue may be performed over an extended period of time, such as 1 day or more, 2 days or more, 3 days or more, 4 days or more, 5 days or more, 6 days or more, 7 days or more, 8 days or more, 9 days or more, 10 days or more, such as, for example, 1 week or more, 2 weeks or more, 3 weeks or more, 1 month or more, 2 months or more, 3 months or more, 4 months or more, 5 months or more, 6 months or more, 7 months or more, 8 months or more, 9 months or more, 10 months or more, 11 months or more, 1 year or more, or ever longer periods of time.

In some cases, the individual is a human. In some cases, the individual is a non-human primate. In some cases, the individual is a rodent (e.g., a rat, a mouse, etc.). The tissue or organ (e.g., "target tissue" or "target organ") may be an in vivo neuronal tissue, a tissue slice preparation, a nerve fiber bundle, a neuromuscular junction, etc. The in vivo neuronal tissue may be neuronal tissue of an animal that is anesthetized or non-anesthetized, and is restrained or non-restrained. The target tissue of interest includes, but is not limited to, the neocortex, the hypothalamus, entorhinal and hippocampal formation cortex, mammillary bodies, septum, bed nucleus of stria terminalis, dorsal and ventral striatum, thalamus, amygdala, accumbens, brainstem, subcortical structures in general, muscle, spinal cord, cardiac tissue, etc.

In some embodiments, the excitable cells (e.g., neurons) in a target tissue or organ are genetically modified to express a light-responsive polypeptide that, when stimulated by an appropriate light stimulus, hyperpolarizes or depolarizes the stimulated excitable cell. The term "genetic modification" refers to a permanent or transient genetic change induced in a cell following introduction into the cell of a heterologous nucleic acid (i.e., nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

In some instances, the light-responsive polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the excitable cell when activated by light of an activating wavelength. In some embodiments, the light-responsive polypeptide hyperpolarizes the excitable cell when activated by light of an activating wavelength.

In some embodiments, the light-responsive polypeptides are activated by blue light. In some embodiments, the light-responsive polypeptides are activated by green light. In some embodiments, the light-responsive polypeptides are activated by yellow light. In some embodiments, the light-responsive polypeptides are activated by orange light. In some embodiments, the light-responsive polypeptides are activated by red light.

In some embodiments, the light-responsive polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive polypeptide. In some cases, the one or more amino acid sequence motifs which enhance light-responsive polypeptide transport to the plasma membranes of mammalian cells is fused internally within a light-responsive polypeptide. Optionally, the light-responsive polypeptide and the one or more amino acid sequence motifs may be separated by a linker. In some embodiments, the light-responsive polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In some embodiments, the signal peptide sequence in the protein can be deleted or substituted with a signal peptide sequence from a different protein.

Exemplary light-responsive polypeptides and amino acid sequence motifs that find use in the present system and method are disclosed in, e.g., PCT App. Nos. PCT/US2011/028893 and PCT/US2015/23087.

The individual may be any suitable individual for analyzing the individual's brain functional activity data. In some cases, the individual is a human individual. In some cases the human is a healthy human, or a human having a neurological disorder. The neurological disorder may be any suitable neurological disorder. In some cases, the neurological disorder is caused by a disease, e.g., a neurological disease. The neurological disease may be any suitable disease associated with pathological activity of a network of neurons. Suitable neurological diseases include, without limitation, Parkinson's disease, Alzheimer's disease, dementia, epilepsy, autism, bipolar disorder, schizophrenia, Tourette's syndrome, obsessive compulsive disorder, attention deficit hyperactivity disorder, Huntington's disease, multiple sclerosis, or migraine. In some embodiments, the neurological disorder is an age-related disorder of brain function.

In certain embodiments, the methods may be used to treat a disease or condition (e.g., a neurological disorder) in the subject that is amenable to treatment using the subject methods. As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

Selective activation of neurons in order to measure subtype-specific functional activity may be done using any suitable method. Suitable methods of selective neuron activation include, without limitation, optogenetic stimulation, single unit electrophysiology, etc. Where the neurons are selectively activated by optogenetic stimulation, the neurons may express one or more light-activated polypeptides configured to hyperpolarize or depolarize the neurons. Suitable light-activated polypeptides and methods used thereof are described further below.

Light-Activated Polypeptides

A light-activated polypeptide of the present disclosure may be any suitable light-activated polypeptide for selectively activating neurons of a subtype by illuminating the neurons with an activating light stimulus. In some instances, the light-activated polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-activated polypeptide depolarizes the cell when activated by light of an activating wavelength. In some embodiments, the light-activated polypeptide hyperpolarizes the cell when activated by light of an activating wavelength. Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T), iC1C2, C1C2, GtACR2, NpHR, eNpHR3.0, C1V1, VChR1, VChR2, SwiChR, Arch, ArchT, KR2, ReaChR, ChiEF, Chronos, ChRGR, CsChrimson, and the like. In some cases, the light-activated polypeptide includes bReaCh-ES, as described herein and described further in, e.g., Rajasethupathy et al., Nature. 2015 Oct. 29; 526(7575):653, which is incorporated by reference. Hyperpolarizing and depolarizing opsins have been described in various publications; see, e.g., Berndt and Deisseroth (2015) *Science* 349:590; Berndt et al. (2014) *Science* 344:420; and Guru et al. (Jul. 25, 2015) *Intl. J. Neuropsychopharmacol*. pp. 1-8 (PMID 26209858).

The light-activated polypeptide may be introduced into the neurons using any suitable method. In some cases, the neurons of a subtype of interest are genetically modified to express a light-activated polypeptide. In some cases, the neurons may be genetically modified using a viral vector, e.g., an adeno-associated viral vector, containing a nucleic acid having a nucleotide sequence that encodes the light-activated polypeptide. The viral vector may include any suitable control elements (e.g., promoters, enhancers, recombination sites, etc.) to control expression of the light-activated polypeptide according to neuronal subtype, timing, presence of an inducer, etc.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2620) Gene Therapy 11:52-60); a motor neuron-specific gene Hb9 promoter (see, e.g., U.S. Pat. No. 7,632,679; and Lee et al. (2620) Development 131:3295-3306); and an alpha subunit of Ca$(^{2+})$-calmodulin-dependent protein kinase II (CaMKIIα) promoter (see, e.g., Mayford et al. (1996) Proc. Natl. Acad. Sci. USA 93:13250). Other suitable promoters include elongation factor (EF) 1α and dopamine transporter (DAT) promoters.

In some cases, neuronal subtype-specific expression of the light-activated polypeptide may be achieved by using recombination systems, e.g., Cre-Lox recombination, Flp-FRT recombination, etc. Cell type-specific expression of genes using recombination has been described in, e.g., Fenno et al., *Nat Methods,* 2014 July; 11(7):763; and Gompf et al., *Front Behav Neurosci.* 2015 Jul. 2; 9:152, which are incorporated by reference herein.

Systems

Aspects of the present disclosure include a functional magnetic resonance imaging (fMRI) system. In certain embodiments, the system is configured for compressed sensing (CS) high-resolution fMRI. In general, the fMRI system is configured to obtain one or more fMRI images of a target area in a subject. For instance, in general, the MRI system includes a permanent magnet or electromagnet of the MRI system that applies a magnetic field to a target area in a subject. In some instances, the system also includes an RF coil that applies an excitation waveform (e.g., an RF excitation waveform) to the target area in the subject to produce detectable image data (e.g., magnetic resonance (MR) signals) of the target area in the subject. One or more additional coils may also be included in the MRI system, such as, but not limited to, one or more shim coils that apply one or more shim fields, one or more gradient coils that apply one or more gradient fields, and the like. In addition, the system includes a receiver (e.g., a receiver coil) that acquires image data (MR signals). The system may also include a processor configured to producing an image of the target area in the subject based on the acquired image data.

As described herein, the fMRI system may be configured for offline processing of the image data, where the acquired image data is saved in a computer-readable memory and analyzed at a subsequent time. In other cases, the fMRI system is configured for real-time processing of the acquired image data, where the acquired image data is analyzed in real-time to produce the image of the target area in the subject.

In certain embodiments, the fMRI system may include an MRI device, a processor, and a memory (e.g., a non-transient memory on a computer-readable medium). For example, the memory may contain an application or program that, when executed by the processor, causes the MRI device to record functional activity of an individual's brain to generate functional activity data for the individual, and further perform a method of analyzing functional activity data, as described herein.

The MRI device may be any suitable MRI device, such as an MRI device configured to perform the high-resolution fMRI methods described herein. Suitable MRI devices are described in, e.g., U.S. Pat. No. 8,834,546, which is incorporated herein by reference.

In certain embodiments, the subject fMRI devices (and systems) are configured to produce an image having a spatial resolution of about 0.2×0.2×0.5 mm$^3$ or greater. For example, the subject fMRI devices (and systems) can be configured to produce images having a spatial resolution of 1×1×1 mm$^3$ or greater, such as 0.9×0.9×0.9 mm$^3$ or greater, or 0.8×0.8×0.8 mm$^3$ or greater, or 0.7×0.7×0.7 mm$^3$ or greater, or 0.6×0.6×0.6 mm$^3$ or greater, or 0.5×0.5×0.5 mm$^3$ or greater, or 0.4×0.4×0.5 mm$^3$ or greater, or 0.3×0.3×0.5 mm$^3$ or greater, or 0.2×0.2×0.5 mm$^3$ or greater, or 0.1×0.1×0.5 mm$^3$ or greater. In certain instances, the subject fMRI devices (and system) are configured to produce an image having a spatial resolution of 0.21×0.21×0.5 mm$^3$. In certain instances, the subject fMRI devices (and system) are configured to produce an image having a spatial resolution ranging from 0.1×0.1×0.5 mm$^3$ to 1×1×1 mm$^3$, such as from 0.1×0.1×0.5 mm$^3$ to 0.9×0.9×0.9 mm$^3$, or from 0.1×0.1×0.5 mm$^3$ to 0.8×0.8×0.8 mm$^3$, or from 0.1×0.1×0.5 mm$^3$ to 0.7×0.7×0.7 mm$^3$, or from 0.1×0.1×0.5 mm$^3$ to 0.6×0.6×0.6 mm$^3$, or from 0.1×0.1×0.5 mm$^3$ to 0.5×0.5×0.5 mm$^3$, or from 0.1×0.1×0.5 mm$^3$ to 0.4×0.4×0.5 mm$^3$, or from 0.1×0.1×0.5 mm$^3$ to 0.3×0.3×0.5 mm$^3$. In certain embodiments, the subject fMRI devices (and system) are configured to produce an image having a spatial resolution ranging from 0.1×0.1×0.5 mm$^3$ to 0.3×0.3×0.5 mm$^3$. In some cases, a processor of the device (or system) is configured to produce an image having a spatial resolution as described herein.

In certain embodiments, the system includes one or more processing units (also called herein "processors"), memory (i.e., a computer readable storage medium), an input/output (I/O) interface, and a communications interface. These components communicate with one another over one or more communication buses or signal lines. In some embodiments, the memory, or the computer readable storage media of memory, stores an operating system, programs, modules, instructions, and stored data. The one or more processors are coupled to the memory and operable to execute these programs, modules, and instructions, and read/write from/to the stored data. In certain embodiments, the programs include one or more of the algorithms as described herein that are used to apply waveforms to the target area in the subject, acquire MR signals, and/or analyze the acquired image data.

In some embodiments, the processing units include one or more microprocessors, such as a single core or multi-core microprocessor. In some embodiments, the processing units include one or more general purpose processors. In some embodiments, the processing units include one or more special purpose processors specifically programmed to apply waveforms to the target area in the subject, acquire MR signals, and/or analyze the acquired image data using one or more of the algorithms, as described herein.

In some cases, the processor is configured to analyze the signals in real-time. In other cases, the acquired signals are saved by the processor in a memory for subsequent analysis of the data (also referred to herein as offline processing).

In some embodiments, the memory includes high-speed random access memory, such as DRAM, SRAM, DDR RAM or other random access solid state memory devices. In some embodiments the memory includes non-volatile memory, such as one or more magnetic disk storage devices, optical disk storage devices, flash memory devices, or other non-volatile solid state storage devices. In some embodiments, the memory includes one or more storage devices remotely located from the processing units. The memory, or alternately the non-volatile memory device(s) within the memory, includes a computer readable storage medium. In some embodiments, the memory includes a non-transitory computer readable storage medium.

In some embodiments, the I/O interface is coupled to one or more input/output devices, such as one or more displays, keyboards, touch-sensitive surfaces (such as a track pad or a touch-sensitive surface of the touch-sensitive display), speakers, and microphones. The I/O interface may be configured to receive user inputs (e.g., voice input, keyboard inputs, etc.) from a user and process them accordingly. The I/O interface may also be configured to present outputs (e.g., sounds, images, text, etc.) to the user according to various program instructions implemented on the system.

In some embodiments, the communications interface includes wired communication port(s) and/or wireless transmission and reception circuitry. The wired communication port(s) receive and send communication signals via one or more wired interfaces, e.g., Ethernet, Universal Serial Bus (USB), FIREWIRE, etc. The wireless circuitry receives and sends RF signals and/or optical signals from/to communications networks and other communications devices. The wireless communications may use any of a plurality of communications standards, protocols and technologies, such as GSM, EDGE, CDMA, TDMA, Bluetooth, Wi-Fi, VoIP, Wi-MAX, or any other suitable communication protocol. The network communications interface enables communication between the system with networks, such as the Internet, an intranet and/or a wireless network, such as a cellular telephone network, a wireless local area network (LAN) and/or a metropolitan area network (MAN), and other devices. Network communications interface is configured to facilitate communications between the system and other devices over a network.

In some aspects, the system may include a computer, which may be a personal device (e.g., laptop, desktop, workplace computer, portable device, etc.). A computer that is a personal device may not need to be connected to a network. In some aspects, the computer is a server or a collection of servers, and may not need an I/O interface. For example, the computer may be a server, and a neural pathway analysis program of the present disclosure may be accessed by a user through a website.

In some embodiments, the operating system (e.g., LINUX®, UNIX®, OS X®, WINDOWS®, or an embedded operating system) includes various software components and/or drivers for controlling and managing general system tasks (e.g., memory management, storage device control, power management, etc.) and facilitates communications between various hardware, firmware, and software components.

It should be noted that the system is only one example, and that the system may have more or fewer components than shown, may combine two or more components, or may have a different configuration or arrangement of the components. The various components of the system may be implemented in hardware, software, firmware, including one or more signal processing and/or application specific integrated circuits, or a combination of thereof.

A neural pathway analysis program that includes one or more programs may be stored in the memory, and include instructions to perform methods according to one or more embodiments of the above methods section. The neural pathway analysis program may include any of the following exemplary modules or a subset or a superset thereof.

In some cases, a neural pathway analysis program may be configured to computationally process functional activity data for a region of a brain of an individual, as described above, to generate an estimate of the relative activities of neural pathways regulated by each of a plurality of neuronal subtypes, by generating a connectivity model from the functional activity data based on a network model of functional connections among interconnected nodes representing the region, as described above; and deriving a set of coefficients from a linear regression between a) the connectivity model; and b) neuronal subtype-specific connectivity estimates among the interconnected nodes, as described above.

The present system may include an fMRI device, configured to measure functional brain activity of an individual.

The computer system may be in communication with the fMRI device, through the communication interface, such that the computer system can control operation of the fMRI device and/or retrieve functional imaging data from the fMRI device.

The neural pathway analysis program may include a model-generating module, e.g., a spDCM module, configured to generate the connectivity model from the functional activity data based on a network model of functional connections among interconnected nodes representing the region.

The neural pathway analysis program may include a linear regression module configured to perform a linear regression between a) the connectivity model; and b) neuronal subtype-specific connectivity estimates, to derive a set of coefficients that represent the contribution to the functional activity data of a neural pathway regulated by different neuronal subtypes.

The methods described herein may be performed by the computer system. In some embodiments, the computer system is a distributed computer system. For example, the computer system includes a first set of one or more processors located remotely from a second set of one or more processors. In some embodiments, the computer system includes a web server configured to provide a web interface. In some embodiments, the web interface is configured to receive data. In some embodiments, the web interface is configured to display results.

In certain aspects, the neural pathway analysis program, may be configurable by a user. For example, a the neural pathway analysis program may include a user interface module (not shown) configured to enable a user to determine one or more settings, such as the network model, neuronal subtype-specific connectivity estimates, whether to include neural fluctuations, etc., to apply to the model generating and/or linear regression algorithms, or any other settings that would allow for one or more embodiments described in the above methods section.

In some embodiments, the system includes a brain stimulation device, such as a deep brain stimulation device or a transcranial magnetic stimulation device, configured to stimulate a brain region of the individual being monitored by the fMRI device. In some instances, the brain stimulation device is an optrode. In some embodiments, the computer system may be configured to control the brain stimulation device based on the analysis of neural pathways contributing to the functional brain activity data, according to methods of the present disclosure. For example, if the neural pathway analysis indicates that an individual has insufficient activity in a neural pathway associated with a neurological disorder from which the individual suffers, the computer system may provide an appropriate stimulation to the relevant brain region that regulates the neural pathway via the brain stimulation device, thereby rebalancing the level of the neural pathway activity in the individual's brain.

Embodiments of the present disclosure may include an implantable device, such as an optrode. Certain embodiments of the subject optrodes can be used to detect electrical signals (and/or changes in electrical signals), such as electrical signals produced near the optrode during use. In some cases, the optrode is configured to detect an electrical signal, such as a local field potential (LFP). An LFP is an electrophysiological signal (electrical potential, or voltage) generated by the summed electric current flowing from multiple nearby neurons within a localized volume of nervous tissue. Voltage is produced across the local extracellular space by action potentials and graded potentials in neurons in the area, and can vary as a result of synaptic activity. For instance, the subject optrode can detect cellular electrical activity of an excitable cell, such as neurons and muscle cells.

In some cases, the optrode is adapted for use in magnetic resonance imaging, such as functional MRI (fMRI). In certain embodiments, the optrode is configured for uniplex analysis of a target area (e.g., target tissue or organ) in a subject. By "uniplex analysis" is meant that a single target area is analyzed using the devices and methods disclosed herein. For example, a single optrode may be used for analysis of one target area in a subject. In these embodiments, the optrode is configured for detection and analysis of single-unit activity in a subject.

Other embodiments include the multiplex analysis of two or more target areas (e.g., target tissues or organs) in a subject. By "multiplex analysis" is meant that the two or more areas of excitable cells may be analyzed using the devices and methods disclosed herein. For example, the system may include two or more optrodes. In some instances, the number of target areas for analysis using multiplex devices as disclosed herein is 2 or more, such as 4 or more, 6 or more, 8 or more, 10 or more, etc., up to 20 or more, e.g., 50 or more, including 100 or more, or 500 or more distinct target areas. In certain embodiments, the devices and methods may be used for the multiplex analysis of 2 to 500 distinct target areas in the subject, such as 2 to 250 distinct target areas, including 2 to 100 distinct target areas, or 2 to 50 distinct target areas, or 2 to 25 distinct target areas, or 2 to 10 distinct target areas. In certain embodiments, 2 or more multiplex assays may be conducted in parallel substantially simultaneously.

As discussed above, the system of the present disclosure may be configured for multiplex analysis, such that the optrode is configured for detection and analysis of multi-unit activity in a subject. As such, the optrode may be configured to include an array of electrodes. An "array" includes any arrangement of individually addressable electrodes. An array is "addressable" when it has multiple electrodes and each electrode may carry a signal independent of the other electrodes in the array. Thus, an array of electrodes may be used to detect distinct signals from different target tissues or organs in a subject. An array may contain 2 or more, 4 or more, 8 or more, 10 or more, 50 or more, 100 or more, 250 or more, or 500 or more electrodes.

Embodiments of the device may also include a light source. In some cases, the light source includes an optical fiber. The optical fiber may be configured to direct light to a target area (e.g., a target tissue or organ) in a subject. For example, the optical fiber may direct light to a target area in the subject that contains excitable cells, such as neurons or muscle cells. As discussed herein, the excitable cells (e.g., neurons) in a target tissue or organ may be genetically modified to express a light-responsive polypeptide that, when stimulated by an appropriate light stimulus, hyperpolarizes or depolarizes the stimulated excitable cell. Thus, the optical fiber may be used to direct light to the target tissue or organ to stimulate the excitable cells. As discussed herein, the optrode may be used to detect electrical signals and/or changes in electrical signals produced by the excitable cells. In some cases, the distal end of the optical fiber is positioned adjacent to the target area in the subject. Light emitted from the distal end of the optical fiber may stimulate the excitable cells as discussed herein. In certain instances, the proximal end of the optical fiber is attached to a source of light. The source of light may be any source of light suitable for performing a desired assay, such as, for example, a source of light that produces light of an appropriate wavelength to stimulate the excitable cells in the target area of the subject. In some cases, the light source is a laser. In some cases, the light source is a light emitting diode (LED). In some cases, two or more light sources may be included in the device, such as light sources that produce light of different wavelengths. In some cases, the device also includes an optical switch.

Utility

Embodiments of the methods and systems described herein find use in a variety of MRI applications, such as MRI methods and systems where high-resolution MRI images are desired. In some cases, the subject methods and systems find use in producing high-resolution functional MRI (fMRI) images of a target area in an individual. For instance, the subject methods and systems find use in fMRI techniques for measuring the brain activity of an individual, such as by detecting changes associated with blood flow in one or more target areas in the brain of the individual. In other cases, the subject methods and systems find use in producing high-resolution functional MRI (fMRI) images of a target area in an individual, where the activity in excitable cells in a target organ or tissue in the individual is assessed. As described herein, the subject methods and systems may find use in detecting the activity of light-responsive polypeptides (e.g., light-activated ion channels) in excitable cells (e.g., neurons) in the individual. As such, the subject methods and systems find use in global and/or regional brain function studies, such as where the activity of one or more target regions of the brain is mapped in high-resolution.

In certain embodiments, the subject methods and systems find use in producing high-resolution fMRI images of a target area in an individual, including high-resolution fMRI images that are produced offline (i.e., where processing of the image data is performed at a time after the image data is acquired), and also high-resolution fMRI images that are produced in real-time (i.e., where processing of the image data occurs immediately following acquisition of the image data and/or during acquisition of the image data).

In some embodiments, the present methods and systems find use in screening in vitro and/or in vivo animal models of disease for neuronal circuit elements diagnostic of or causative for neuropsychiatric disease. For example, the present methods and systems find use in pre-surgical brain function diagnosis. Embodiments of the present methods and systems also find use in planning brain machine interface, such as by mapping the neuronal activity in areas of the brain to determine appropriate locations in the brain for brain machine interface.

In some embodiments, the present methods and systems find use in diagnosis of neuropsychiatric diseases of interest, which may include disorders of mood and affect, anxiety, psychosis, personality, etc. In some instances, an animal model may be used. The animal model may be any suitable model, including, but not limited to, rodents, cats, dogs, monkeys, and non-human primates. Perturbations used to model a neuropsychiatric disease include genetic models of neurological or psychiatric disease, such as autism; chronically induced models as with kainate or pilocarpine-induced epilepsy or chronic stress-induced depression; and acutely induced models as with hallucinogens or psychotogenic agents such as ketamine or phencyclidine (PCP). By comparing the difference in activity pattern between neurons in normal target tissue and neurons in abnormal target tissue, neural correlates of the neuropsychiatric disorder may be identified. Optical control of neurons in the target tissue may then allow identification of causative neuronal activity patterns for a particular neuropsychiatric disorder. These manipulations may potentially provide novel treatment targets. As such, in some embodiments, the present methods and systems find use in diagnostic methods for neuropsychiatric diseases, e.g., where the diagnosis is carried out on a human or non-human mammalian subject.

In some embodiments, the present methods and systems find use in methods for identifying a treatment, e.g., a therapeutic treatment, with a desired activity on a group of neurons. If the desired outcome is known, then the present methods and systems may be used to screen for treatments, including, but not limited to, pharmacological agents, nonchemical based therapeutic treatment; behavioral treatment; electrical, magnetic, or optical based neural-modulation treatment; etc., that will bring about the desired neuronal activity pattern. The screening may be performed in any suitable animal model, either normal, or a model for a neurological disorder, such as Alzheimer's and Parkinson's disease, mild cognitive impairment, other dementias, and Down's Syndrome, as well as schizophrenia, autism, mood, affective, anxiety, and personality/developmental disorders, or other disease models described herein.

In some embodiments, the present methods and systems find use in the treatment of a condition or disorder, such as a neurological or psychiatric condition using optogenetic control. As real-time activity of neurons is monitored using the present methods and systems, a controller or processor may be configured to modulate the activity of neurons in response to the imaged activity signals in such a way as to treat or reduce symptoms of the condition or disorder, at the behavioral and/or physiological levels.

Computer Related Embodiments

A variety of computer-related embodiments are also provided. Specifically, the data analysis methods described herein may be performed using a computer, e.g., a processor. Accordingly, provided is a computer-based system for analyzing data produced using the above methods and systems in order to provide qualitative and/or quantitative analysis of a target area of interest in a subject.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include CD-ROM, DVD-ROM, BD-ROM, a hard disk drive, a ROM or integrated circuit, a magneto-optical disk, a solid-state memory device, a computer readable flash memory, and the like, whether or not such devices are internal or external to the computer. A file containing information may be "stored" on computer readable medium, where "storing" means recording information such that it is accessible and retrievable at a later date by a computer (e.g., for offline processing). Examples of media include, but are not limited to, non-transitory media, e.g., physical media in which the programming is associated with, such as recorded onto, a physical structure. Non-transitory media for storing computer programming does not include electronic signals in transit via a wireless protocol.

In certain embodiments, computer programming may include instructions for directing a computer to perform one or more steps of the methods disclosed herein. For example, the computer programming may include instructions for directing a computer to detect and/or analyze signals acquired by the systems and devices disclosed herein (e.g., the presently disclosed fMRI systems). In certain embodiments, the computer programming includes instructions for directing a computer to analyze the acquired MR signals qualitatively and/or quantitatively. Qualitative determination includes determinations in which a simple yes/no result is provided to a user with respect to the presence or absence of a detectable signal. Quantitative determination includes both semi-quantitative determinations in which a rough scale result, e.g., low, medium, high, is provided to a user regarding the detectable signal and fine scale results in which an exact measurement of the detectable signal is provided to a user (e.g., a quantitative measurement of local field potentials in a target area of interest).

In some embodiments, the computer programming includes instructions for directing a computer to perform a uniplex analysis of an analyte in a sample. By "uniplex analysis" is meant that detection and analysis is performed on a single target area in the subject. For example, a single tissue area in the subject containing excitable cells may be analyzed. In some embodiments, the computer programming includes instructions for directing a computer to perform a multiplex analysis of two or more target areas in a subject. By "multiplex analysis" is meant that the two or more distinct areas of interest in a subject are analyzed. For example, two or more distinct tissue areas in the subject each containing excitable cells may be analyzed. In certain embodiments, the computer programming includes instructions for directing a computer to perform several multiplex assays in parallel substantially simultaneously.

With respect to computer readable media, "permanent memory" refers to memory that is not erased by termination of the electrical supply to a computer or processor. Computer hard-drive, CD-ROM, DVD-ROM, BD-ROM, and solid state memory are all examples of permanent memory. Random Access Memory (RAM) is an example of non-permanent memory. A file in permanent memory may be editable and re-writable. Similarly, a file in non-permanent memory may be editable and re-writable.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Two versions of compressed sensing (CS) high-resolution functional magnetic resonance imaging (fMRI) were developed for offline and real-time experiments. There were three different parts in each version, including data acquisition paradigm, reconstruction algorithm, and regularization parameter optimization strategy.

In the offline CS high-resolution fMRI, a randomized under-sampling stack of multi-interleaf variable density spiral (VDS) trajectory was used. The total number of interleaves at each kz-slice followed a Laplacian distribution, where the center k-space was more densely sampled than the outer k-space. The sampling paradigm achieved 35×35×16 mm FOV and 0.21×0.21×0.5 mm resolution, which was about 6 times higher than the standard fMRI resolution. This sampling paradigm was implemented into a passband balanced steady state free precession (b-SSFP) sequence with TE=2 ms, and TR=9.375 ms. To enable full brain coverage without b-SSFP banding, two acquisitions were performed and the two phase-cycled images were combined by maximum intensity projection. The undersampled image in the offline CS high-resolution fMRI was iteratively reconstructed using an L1 regularized cost function, where both the fMRI temporal and spatial domain were regularized by discrete cosine transform (DCT). The cost function was solved by gradient descent method. Many computationally intensive calculations such as the non-uniform fast Fourier transform (NUFFT), matrix arithmetic and DCT were implemented on the graphics processing unit, which achieved 34-fold overall improvement in reconstruction speed compared to the CPU implementation. The optimal regularization parameter for the offline CS high-resolution fMRI reconstruction was identified by reconstructing phantoms with a range of regularization parameters and monitoring five different metrics of the reconstructed images. Three distinct phantoms at a normal (30 dB) and low (25 dB) signal to noise ratio with different background images were used. Six-cycle 20s-on-40s-off canonical SPM hemodynamic response function (HRF) were added to phantoms. The five monitored metrics included the contrast to noise ratio, active volume within the designed active region, mean F statistic value, normalized root mean squared error (NRMSE) and peak HRF amplitude. A set of regularization parameters was considered to be in the optimal range if its corresponding CNR, active volume within the designed mask, and mean F-value were greater than that of the ground-truth, and its NRMSE was less than 105% of the minimum NRMSE found within the search range.

In the real-time CS high-resolution fMRI, a randomized stack of variable density spiral sampling paradigm was used. The sampling density followed an exponential function along the kx and ky plane and the variance of the exponential function decreased along the kz direction. Randomness was introduced into the sampling for CS reconstruction by randomly perturbing the angle of each spiral interleaf. The trajectory also had a slightly larger total number of interleaves and then interleaves on the outer k-space were randomly skipped following a Gaussian distribution to achieve the desired temporal resolution. This trajectory was implemented with 35×35×16 mm FOV and 0.25×0.25×0.5 mm spatial resolution, which was 4 times higher than the resolution of the standard fMRI. The undersampled dataset was reconstructed in real-time using an L1 spatial regularized cost function. Daubechies 4 wavelet was used for the sparsifying transform. The fast iterative shrinkage thresholding algorithm (FISTA) was applied to solve the cost function, which converged in approximately 30 iterations. The optimal regularization parameters were identified for the real-time high-resolution fMRI by reconstructing phantoms with a range of regularization parameters and monitoring the CNR, mean F-value, NRMSE, peak HRF amplitude, sensitivity and false positive rate in the reconstructed dataset. The optimal regularization parameters were identified as the intersect of the parameters that gave top 50% CNR, mean F-value, sensitivity, and bottom 50% NRMSE and false positive rate.

Example 1

In preclinical studies, a High SPAtial Resolution compressed SEnsing (HSPARSE) fMRI method was tested and a systematic evaluation was performed to assess CS high spatial resolution fMRI. fMRI spatial resolution for the HSPARSE method was maximized from multiple aspects: optimization of the contrast with a balanced steady state free precession (b-SSFP) sequence, which enabled T2 microvascular sensitive imaging (Kim et al., 2012, Park et al., 2011) with low spatial distortion (Lee et al., 2010, Scheffler et al., 2003, Miller et al., 2006, Lee et al., 2003).

In order to validate this approach, data acquisition was optimized with a randomly under-sampled variable density spiral (VDS), which enabled 6-fold spatial resolution improvement with an acceleration factor of 5.3, which was designed with a balanced steady state free precession sequence to achieve high spatial resolution data acquisition. This ratio was 32% greater than that reported in previous CS fMRI studies with a single coil (Holland et al., 2013, Zong et al., 2014). A modified k-t SPARSE method was then implemented and applied with a strategy to optimize regularization parameters for consistent, high quality CS reconstruction.

The performance and reliability of the HSPARSE method was then evaluated. Because the CS reconstruction was substantially dependent on the regularization parameters, the roles of the spatial and temporal regularizations were investigated. Accordingly, systematic evaluation of the capability of the HSPARSE in detecting functional differences between neighboring active regions (e g laminar specificity) was performed. Lastly, the HSPARSE method was tested in vivo with optogenetic fMRI (ofMRI) experiments.

The results indicated that the methods of the present disclosure improved spatial resolution by 6-fold with 12 to 47% contrast-to-noise ratio (CNR), 33 to 117% F-value improvement and maintained the same temporal resolution. It also achieved high sensitivity of 69 to 99% compared the original ground-truth, small false positive rate of less than 0.05 and low HRF distortion across a wide range of CNRs. The method was robust to physiological noise and enabled detection of layer-specific activities in vivo, which cannot be resolved using the highest spatial resolution Nyquist acquisition.

The methods of the present disclosure enabled high spatial resolution fMRI that could resolve layer-specific brain activity and demonstrated the significant improvement that CS can bring to high spatial resolution fMRI.

Materials and Methods

A randomly under-sampled variable density spiral trajectory enabling an acceleration factor of 5.3 was designed with a balanced steady state free precession sequence to achieve high spatial resolution data acquisition. A modified k-t SPARSE method was then implemented and applied with a strategy to optimize regularization parameters for consistent, high quality CS reconstruction. In this section, the methods and design of HSPARSE were described, and subsequently the in vivo testing of the HSPARSE method with optogenetic fMRI (ofMRI) experiments is described.

1.1 Randomly Under-Sampled, Variable-Density Spiral, b-SSFP Data Acquisition

A randomized under-sampling VDS b-SSFP sequence was designed for the HSPARSE fMRI method. Compared to conventional gradient-recalled-echo (GRE) sequence, the b-SSFP sequence provided lower spatial distortion and better activity localization with T2 microvascular sensitivity. The VDS trajectory also provided high sampling efficiency and robustness against motion, off-resonance, and gradient artifacts. In addition, using spiral trajectory for CS also resulted in the highest CNR compared to most CS under-sampling trajectories available (Jeromin et al., 2012).

Figure 1B:
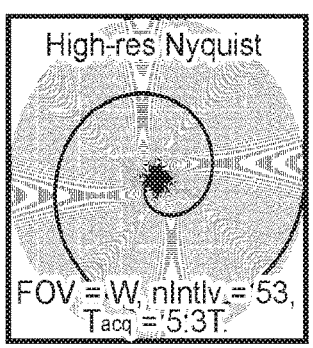
(FIG. 1B) To achieve higher spatial resolution without introducing aliasing artifacts or changing the field of view, the k-space coverage can be increased with more interleaves. This inevitably increases the data acquisition time and reduces the temporal resolution.
Figure 1C:
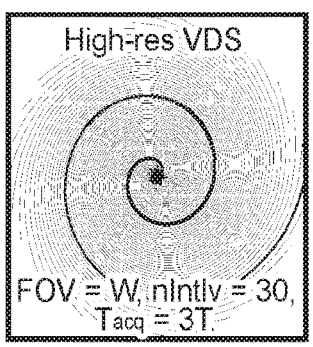
(FIG. 1C, 1D) To overcome this problem, a variable density spiral (VDS) trajectory was designed and interleaves were randomly sampled while keeping the total number of interleaves and scan time the same as the low spatial resolution Nyquist scan.
Figure 1D:
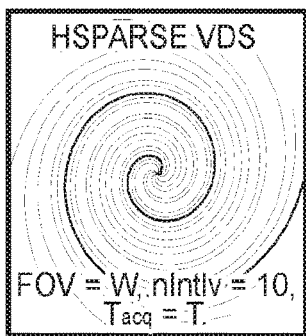
Figure 1E:
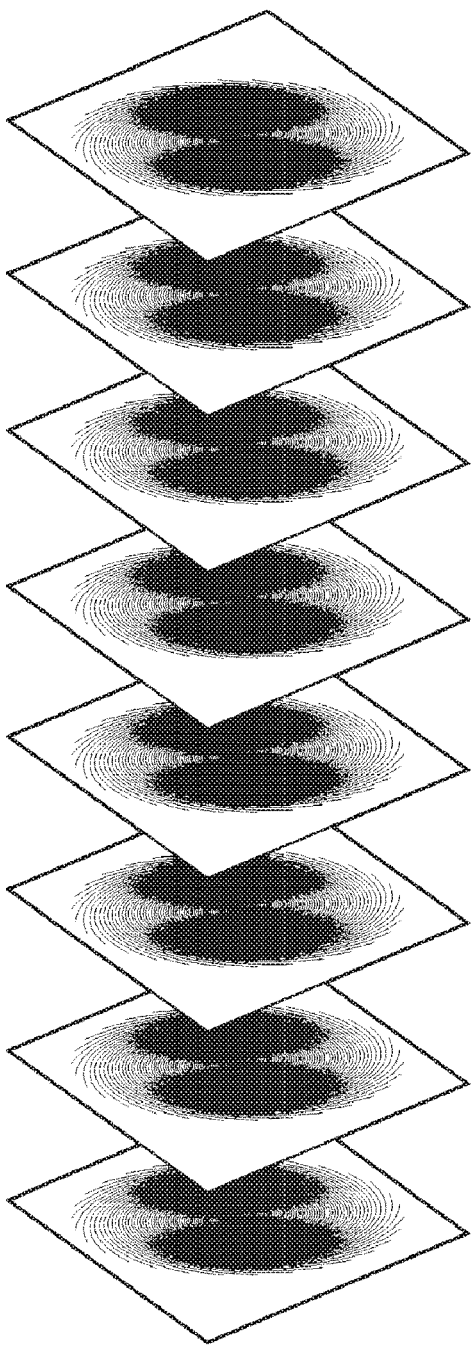
(FIG. 1E, 1F) For 3D acquisition, the HSPARSE fMRI method randomly selects 320 interleaves from a stack of VDS trajectory consisting 32 kz locations and 30 interleaves. More interleaves were sampled near the k-space center and the total number of interleaves in each kz location follows a Laplacian distribution. The sampling pattern was also chosen to be random across temporal frames to exploit the temporal sparsity. However, the total number of interleaves for each time frame was designed to be constant (320 interleaves) to maintain constant temporal resolution over time. Compared to a 3D Nyquist sampled trajectory that has the same spatial resolution, the trajectory used herein achieved a high acceleration factor of 5.3.
Figure 1F:
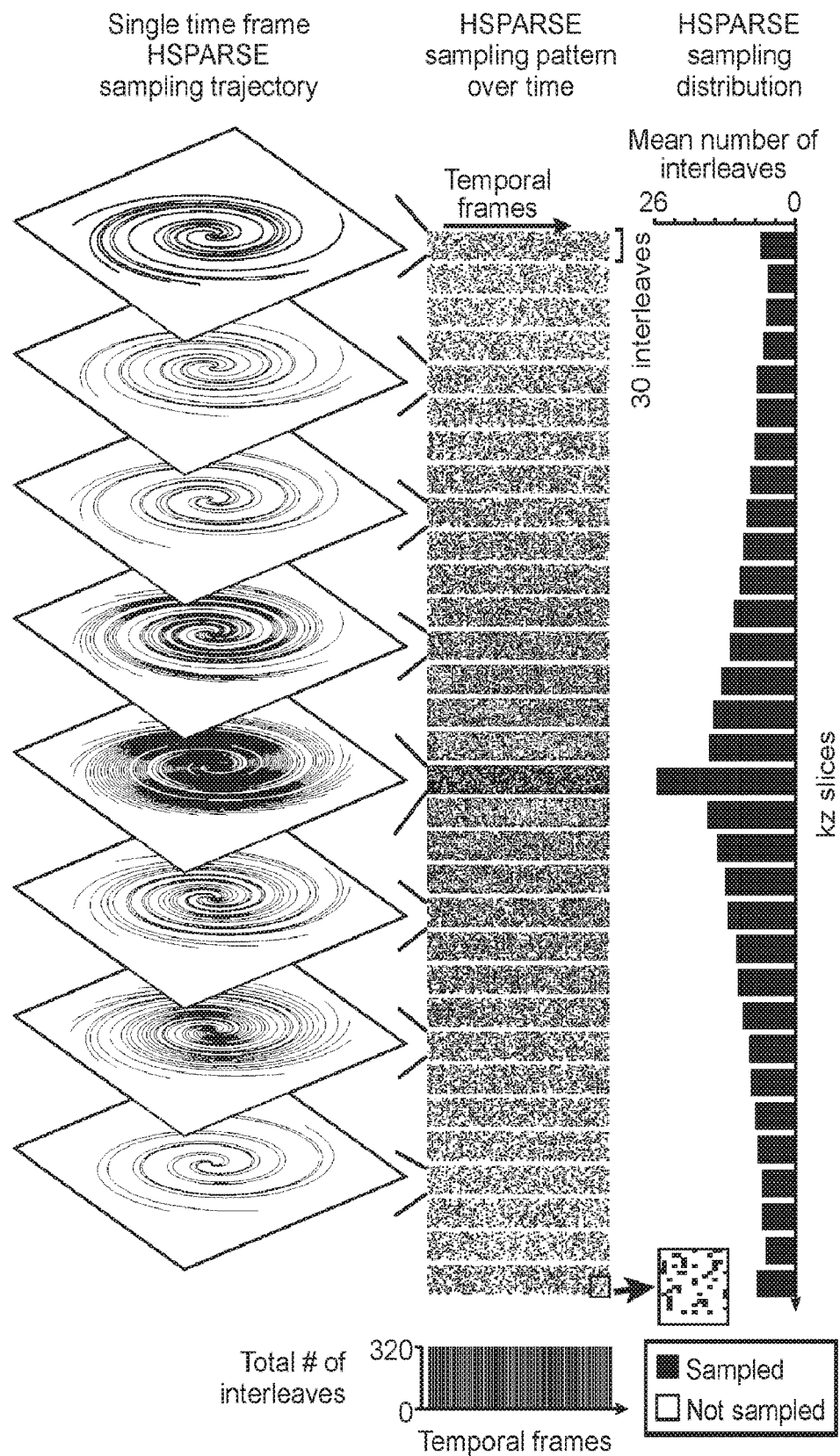

A high spatial resolution Nyquist acquisition (FIG. 1B) required longer acquisition time and resulted in lower temporal resolution compared to the low spatial resolution Nyquist acquisition (FIG. 1A) with the same field of view (FOV). To enable high spatial resolution without sacrificing the temporal resolution, the sampling was accelerated by 1.77 times with a 3D VDS trajectory consisting of 32 kz locations and 30 interleaves at each kz location (FIG. 1C, 1E). Then, 320 interleaves were randomly selected from the 3D VDS trajectory (FIG. 1D, 1F), which further accelerated the sampling by another factor of 3 and resulted in an overall acceleration factor of 5.3. To obtain more interleaves at the center k-space, the number of interleaves at each kz slice was designed to follow a Laplacian distribution (mean $\mu=16$, scaling $b=11$). The under-sampling patterns were also randomized across temporal frames to exploit the fMRI temporal sparsity. However, the total number of interleaves was identical across temporal frames to achieve constant temporal resolution. This design not only enabled rapid data acquisition but also successfully achieved the incoherent sampling for effective CS reconstruction.

The HSPARSE passband b-SSFP acquisition scheme was implemented on a 7 Tesla Bruker scanner with a single transmit and receive surface coil using TE=2 ms, TR=9.375 ms, and flip angle=30°. With a 35×35×16 mm FOV, the sequence was designed to obtain spatial resolution of 0.21× 0.21×0.5 mm and 167×167×32 matrix size at a 3 s temporal resolution. A fully-sampled b-SSFP sequence was also designed with the highest spatial resolution achievable (0.5× 0.5×0.5 mm resolution, 70×70×32 matrix size) while maintaining the same FOV and temporal resolution. To enable full brain coverage without b-SSFP banding at either resolution, two acquisitions were performed with 0° and 180° phase-cycling angles. The two phase-cycled images were then combined by maximum intensity projection (Lee et al., 2008).

1.2 Accelerated CS fMRI Reconstruction

Similar to CS MRI, spatial sparsity of each fMRI frame was used to reconstruct an under-sampled fMRI dataset (Holland et al., 2013, Hugger et al., 2011, Asslander et al., 2013):

$$\operatorname*{argmin}_{m} f(m) = \frac{1}{2}\|Fm - y\|_2^2 + \lambda \|\Psi_s m\|_1 \qquad [1]$$

where F represents the non-uniform Fast Fourier transform (NUFFT) (Fessler et al., 2007) in the spatial domain, m was the 4D image under reconstruction, y was the randomly under-sampled 4D kt-space data, $\mu$ was the regularization coefficient, and $\Psi_S$ represents a spatial sparsifying transform such as the discrete cosine transform (DCT) or discrete wavelet transform (DWT). As shown by Holland et al. 2013, the performance of this algorithm was largely dependent on the trajectory design and the algorithm may fail at a large under-sampling ratio. Therefore, an alternative constraint utilizing temporal redundancy (Gamper et al., 2008, Otazo et al., 2010, Zong et al., 2014) has been developed:

$$\operatorname*{argmin}_{m} f(m) = \frac{1}{2}\|Fm - y\|_2^2 + \lambda \|\Psi_t m\|_1 \qquad [2]$$

where $\Psi_t$ was the sparsifying transform along the temporal dimension. Low complexity transforms such as the Fourier transform and DCT can be applied in block-design fMRI, and more complicated transforms such as the Karhunen Loeve Transform (KLT) and DWT was recommended in complex designs such as event-related fMRI.

In the current implementation, a modified kt-SPARSE (Lustig et al., 2006) technique was utilized where both the temporal and spatial redundancies were exploited:

$$\underset{m}{\mathrm{argmin}}\ f(m) = \frac{1}{2}\|Fm - y\|_2^2 + \lambda_1\|\Psi_t m\|_1 + \lambda_2\|\Psi_s m\|_1 \qquad [3]$$

Figure 2A:
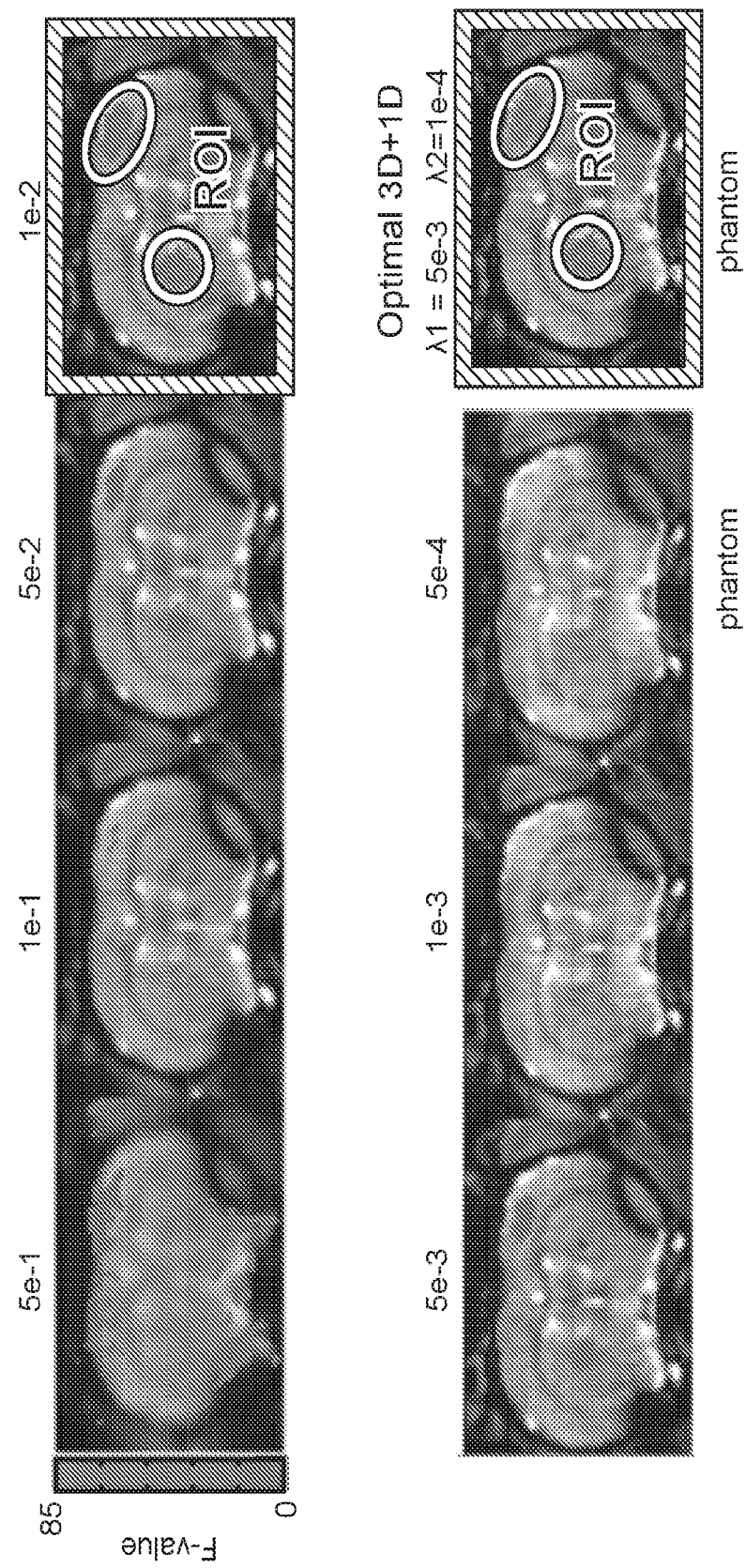
Figure 2C:
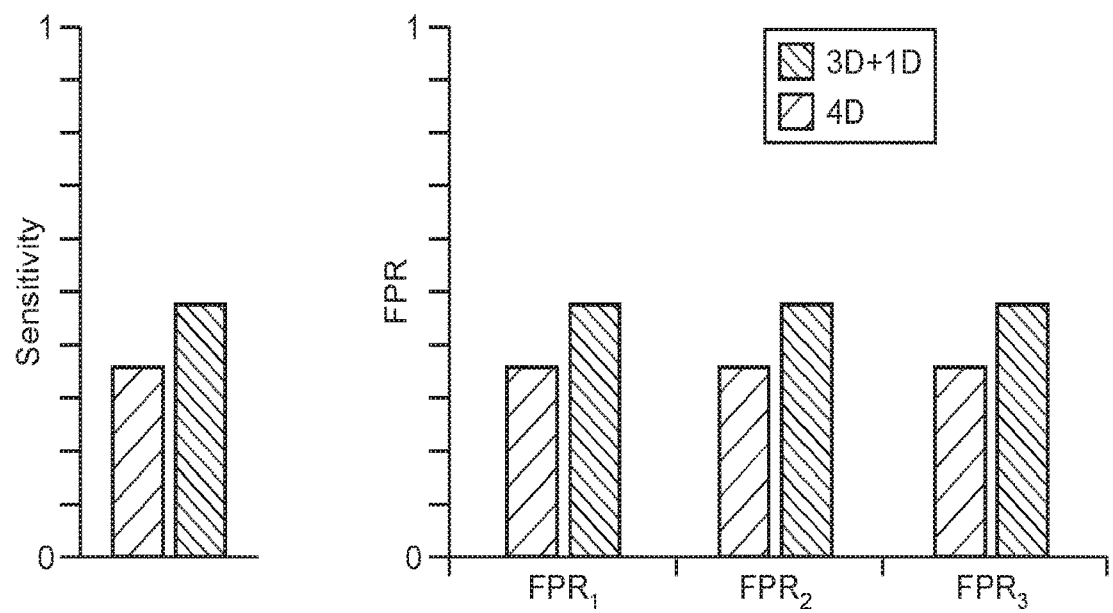
Figure 2D:
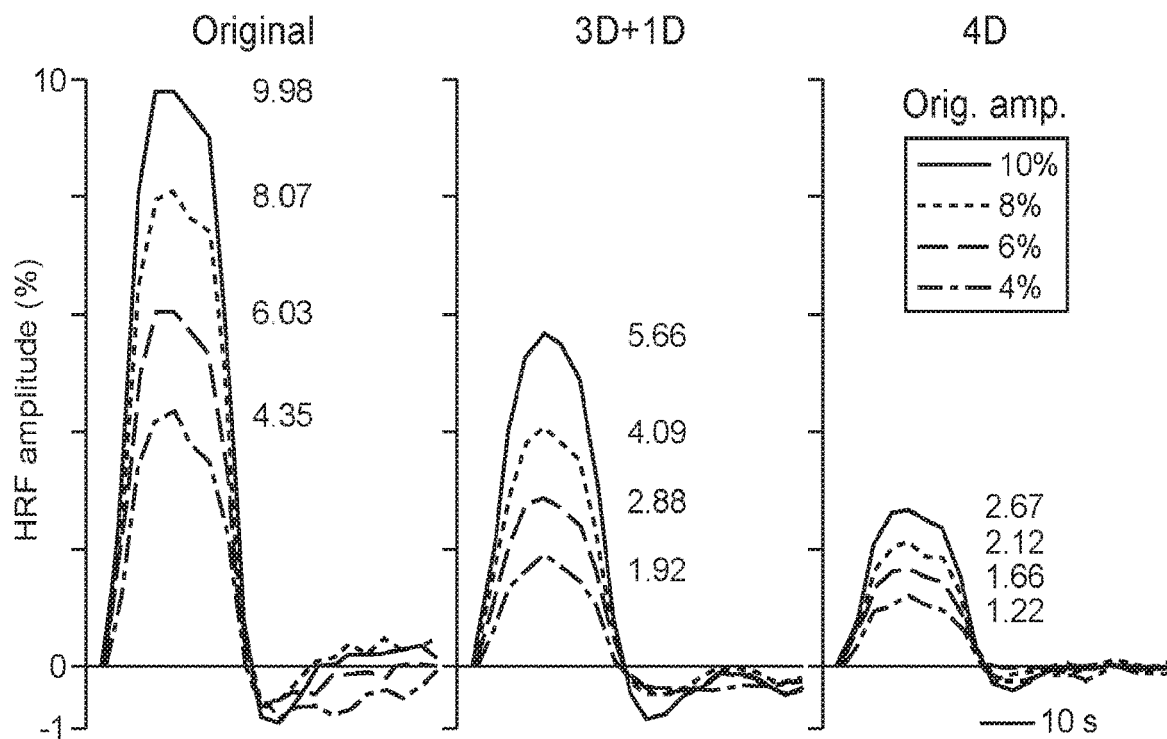

This cost function allows an acceleration factor and reconstruction quality no worse than methods utilizing only spatial or temporal sparsity constraints because its solution set contains optimal solutions of both the spatial and temporal regularization methods. Compared to the cost function that utilizes the 4D sparsifying transform, this method also gives higher image contrast, lower noise level, and lower false positive rate (FIG. 2).

DCT was chosen for both the spatial and temporal sparsifying transform in the implementation. It has previously been shown that the FT can serve as an effective transform for block-designed CS fMRI. Because DCT has a higher compression ratio than the FT, therefore, DCT can enable better reconstruction for the block-designed fMRI. In addition, DCT also has lower complexity than the data-driven KLT and faster speed than the multi-level-decomposition based DWT on a parallel platform. In order to systematically optimize the reconstruction and investigate hundreds of reconstructions under a wide range of regularization parameters, DCT was chosen to facilitate this process.

Figure 3A:
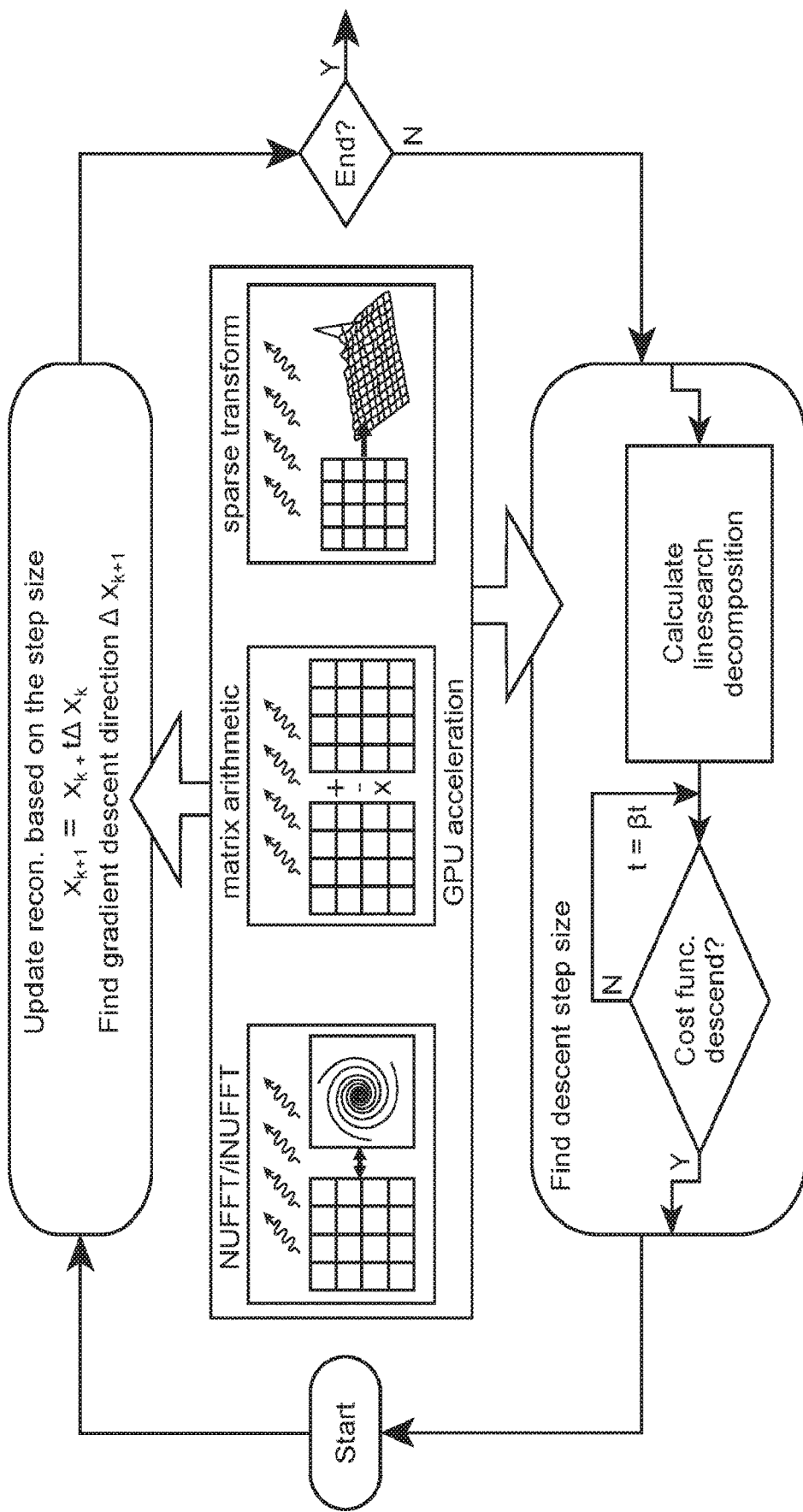
(FIG. 3A) Key computationally intensive calculations such as the NUFFT, matrix arithmetic, and DCT were parallelized on a GPU. Since these computations were repeatedly used during the iterative reconstruction loops used in HSPARSE, the GPU parallelization significantly improves the reconstruction speed. The iNUFFT and NUFFT were the most complicated and time-consuming calculations in the HSPRSE reconstruction.

A fast implementation of the gradient descent method was applied (Boyd et al., 2004) (FIG. 3 and FIG. 4) to solve equation [3]. All key processing on a GPU was computed, which reduced the reconstruction time from 18 hours to 30 minutes and achieved 34-fold acceleration. Implementation details can be found in the supporting information.

1.3 Optimization of Regularization Parameters

High-speed reconstruction achieved by the GPU parallelization enabled exhaustive testing of the HSPARSE reconstruction across different regularization parameters and phantoms to investigate roles of the spatiotemporal regularizations and to identify optimal parameters for various imaging conditions. Three distinct phantoms (denoted A1, B1 and C1) at a normal (30 dB) and low (25 dB) SNR (FIG. 5A) were designed. The A1 phantom was designed to simulate an in vivo experiment, while B1 and C1 were designed to test across different base images and activation patterns. The base image of the B1 phantom was generated from a rat MRI template (Schwarz et al., 2006). Six-cycle 20s-on-40s-off canonical SPM hemodynamic response function (HRF) were added to phantoms in this and following simulations. The peak HRF amplitudes were set to be 10% modulation of the baseline at the activation pattern center, and decreased with distance following a Gaussian function. After a coarse parameter search to find potential optimal parameter range, the following range of parameters were investigated: 1 from 1e-2 to 5e-5 with 8 steps and $\lambda 2$ from 5e-3 to 1e-9 with 14 steps. Because values of the $\lambda 1$ and $\lambda 2$ were dependent on the value of the sampled k-space, the k-space of each dataset was normalized by its corresponding maximum absolute values ($.\|k_{sig}\|_\infty=1.$) to enable comparison of the $\lambda 1$ and $\lambda 2$ among different reconstructions.

The data was analyzed with five-gamma basis set general linear model (GLM) using the SPM. F-test was then conducted and active voxels were recognized as those having an F-value greater than 4.42 (P<0.001). A set of regularization parameters was considered to be in the optimal range if its corresponding CNR, active volume within the designed active region, and mean F-value were greater than that of the ground-truth, and its normalized root mean squared error (NRMSE) between the ground-truth and the HSPARSE reconstructed images was less than 105% of the minimum NRMSE found within the search range. The peak HRF amplitude was calculated as the maximum value of the GLM regressed HRF. And the CNR was estimated as the peak HRF amplitude divided by the standard deviation of the residual time-series.

1.4 Evaluation of fMRI Signal Sensitivity and False Positive Rate

Figure 5A:
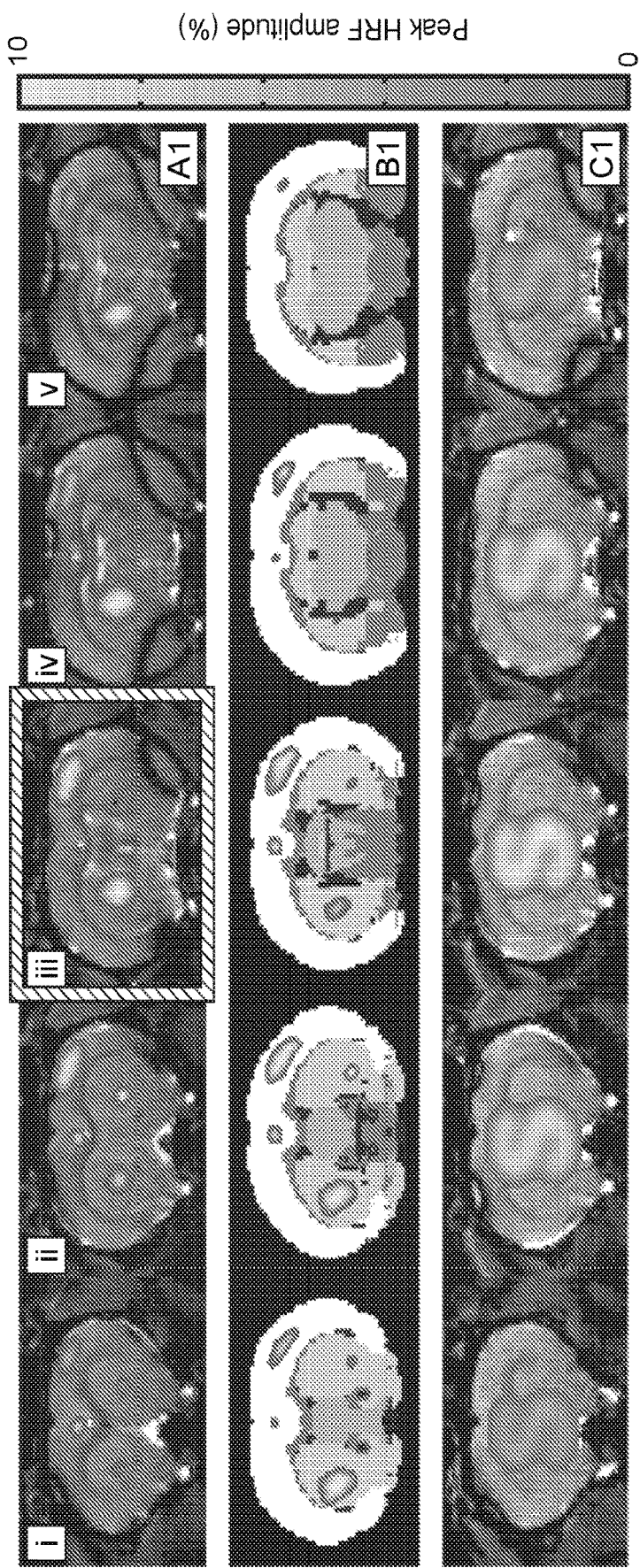
(FIG. 5A) To identify the optimal regularization parameters for reconstruction, three phantoms with two noise levels (25 dB and 30 dB) were generated. The phantoms were designed to first simulate an in vivo fMRI experiment (A1), then to assess the effects of having a distinct base image (B1) and a distinct activation pattern (C1). To simulate more realistic imaging cases, the activation patterns were designed to have decreasing amplitude towards the edge of the activation through Gaussian smoothing (see methods).
Figure 5B:
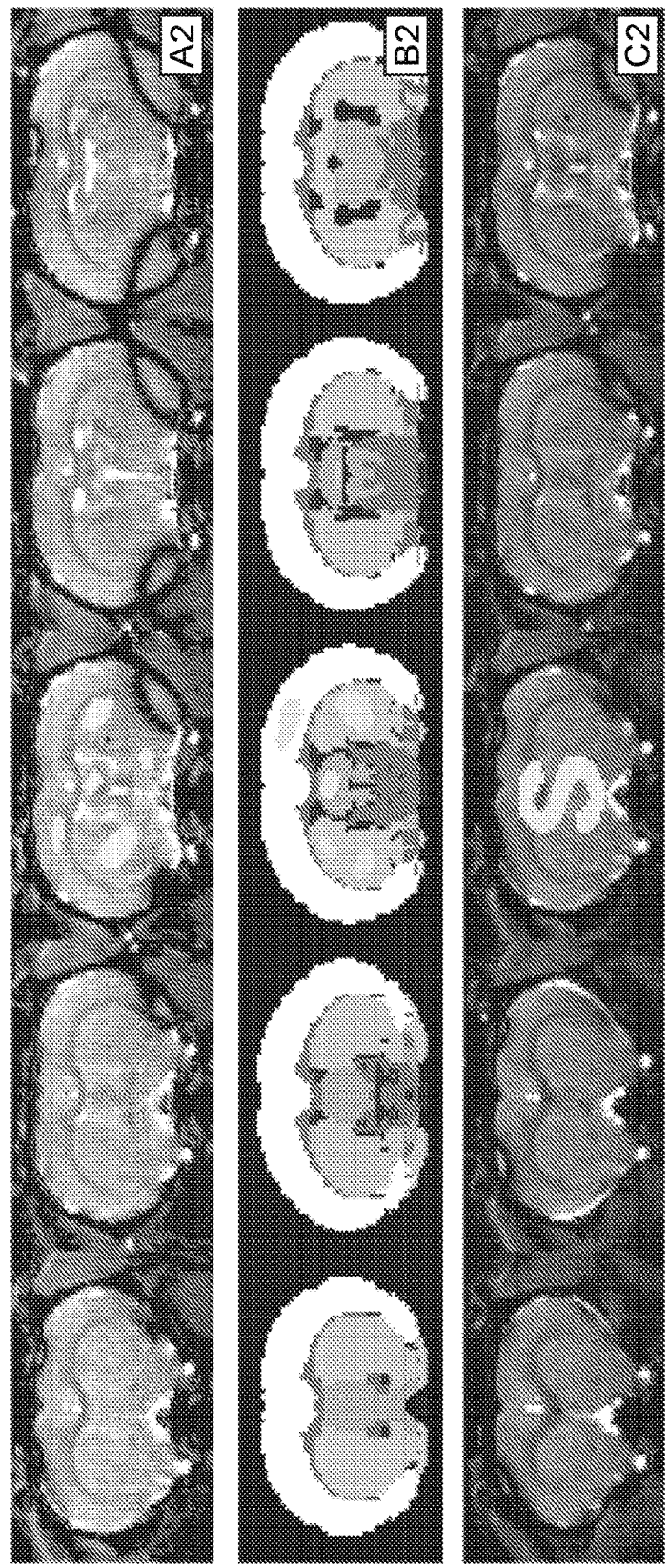
(FIG. 5B) For the assessment of fMRI signal sensitivity and specificity, three 30 dB phantoms were designed to have sharp activation boundaries with activation patterns limited to a single slice.

To quantitatively evaluate the sensitivity and false positive rate (FPR) of the HSPARSE fMRI method in 3D space, three additional 30 dB phantoms were designed (A2, B2, and C2) in which activity was confined to a single imaging slice with sharp contrast boundaries (FIG. 5B). This single-slice pattern was designed to evaluate the sensitivity and FPR under the most difficult conditions, and higher sensitivity and lower FPR was expected in real application. Four different peak HRF amplitudes (10, 8, 6 and 4%, corresponding to CNR 2.55, 2.05, 1.58 and 1.23) were tested. As shown in FIG. 6A, the sensitivity was quantified as the ratio between the number of true positive voxels and the number of true positive plus false negative voxels. The FPR was evaluated as the ratio between the number of false positive voxels and the number of false positive plus true negative voxels in the first to fifth pixel perimeter layer in 3D (FIG. 6B).

1.5 Evaluation of HRF Temporal Characteristics

Figure 5C:
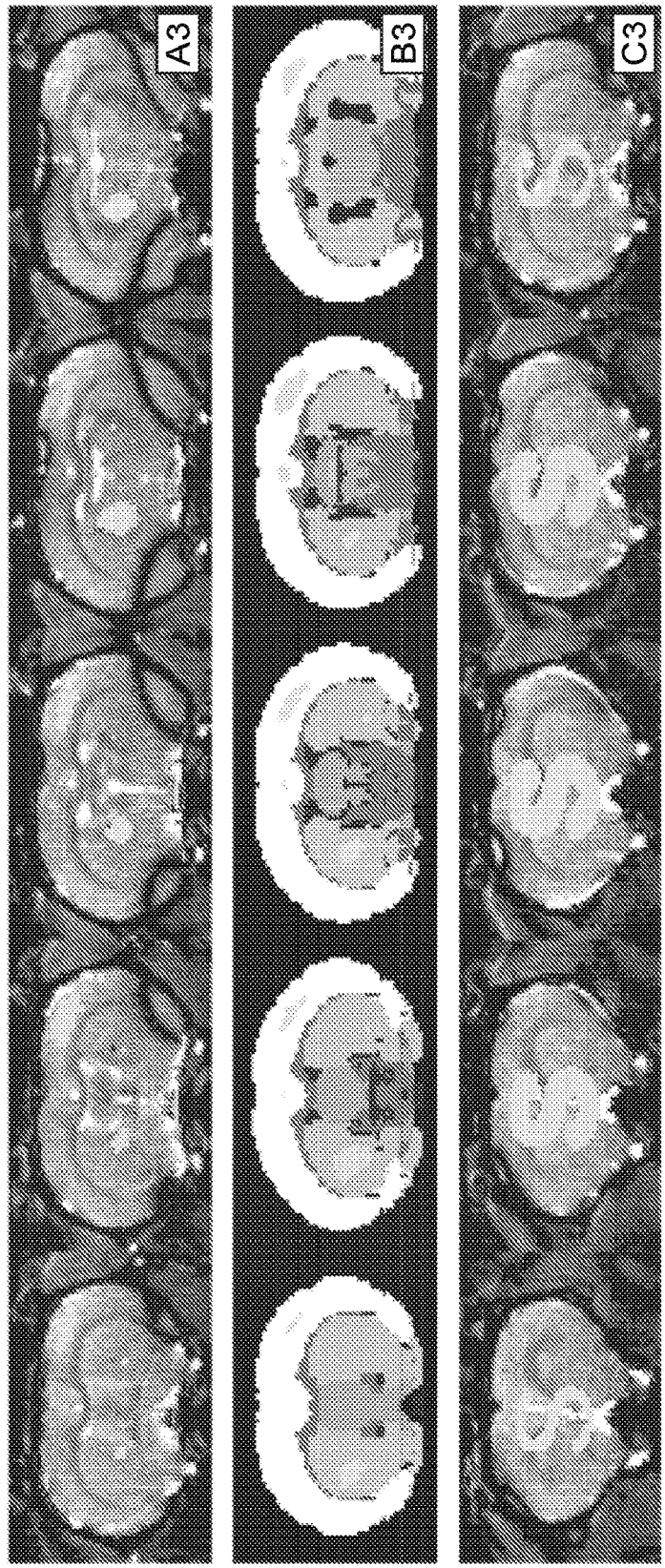
(FIG. 5C) To investigate temporal characteristics of the reconstructed HRFs, three additional 30 dB phantoms without Gaussian smoothing were generated that simulated an in vivo fMRI experiment (A3), an experiment with a different base image (B3), and an experiment with a distinct activation pattern (C3).

Because temporal redundancy was utilized to reconstruct images in CS fMRI, reconstruction may introduce a certain amount of temporal distortion into the resulting fMRI signal. Therefore, the temporal characteristics of the HSPARSE fMRI signal were evaluated to determine the nature of the resulting distortion. Three phantoms (A3, B3, and C3) were designed with SNR of 30 dB and peak HRF amplitudes of 10, 8, 6 and 4% (FIG. 5C). Each phantom was reconstructed 5 times with independent identical Gaussian distributed noise using previously identified optimal parameters ($\lambda_1$=5e-3 and $\lambda_2$=1e-4).

1.6 Evaluation of Robustness to Physiological Noise

Physiological noise in fMRI can lead to decreased sensitivity, increased FPR, and temporal distortion (Kruger et al., 2001), which could be more severe in CS fMRI due to the under-sampling. Therefore, the robustness of the HSPARSE fMRI was evaluated with fully-sampled in vivo datasets containing physiological noise. However, because a fully-sampled high spatial resolution fMRI dataset cannot be acquired without reducing the temporal resolution (due to the fundamental hardware limitations), the highest spatial resolution was acquired in fully-sampled datasets instead. Three fully-sampled in vivo dentate gryus stimulation datasets were acquired. This data was then under-sampled by 5.3 times and reconstructed with the HSPARSE method for comparison.

1.7 Systematic Evaluation of Spatial Resolution

After separately evaluating spatial and temporal distortions, the capability of the HSPARSE method was systematically evaluated to detect functional differences between neighboring active regions, such as the laminar specific responses. Three 35 dB phantoms were designed with increasing difficulty in resolving activations. First, three regions with clear boundaries consisting of signals with distinct peak HRF amplitudes (15, 10 and 5%) (FIG. 7A) or latencies (FIG. 7D) were created. Second, patterns with interleaved layers consisting of signals with different peak HRF amplitudes (12 and 4%, FIG. 7A) or latencies (FIG. 8D) were designed. Spatial distortion in the first one may only result in ambiguous region boundary whereas spatial distortion in the second phantom can result in complete loss of layers. Third, the spatial resolution limit of the HSPARSE fMRI was further explored using an activity pattern containing different widths of interleaved signals going down to the single pixel (FIG. 8G, 8H). These activity patterns were added to six continuous slices for each phantom.

1.8 In Vivo Evaluation with Optogenetic Dentate Gyrus Stimulation

Finally, the spatial resolution, sensitivity, and temporal distortion of the HSPARSE method was compared to the highest spatial resolution Nyquist acquisition in vivo by selectively stimulating dentate gyrus excitatory neurons in three rats using optogenetics. Optogenetic fMRI was performed because it allows precise stimulation of target brain regions, which can result in highly localized activations for evaluating improvements in spatial resolution. The dentate gyrus was targeted (FIG. 9A) due to its unique layered shape (FIG. 9B). It also forms the input structure of the hippocampus and its unique unidirectional nature provides a predictable pattern of activity in hippocampus and downstream structures, which can help evaluate the spatial resolution of different fMRI methods. The data was acquired at 3 s temporal resolution and each dataset included 10 baseline frames and 120 frames of 6-cycle 20s-on-40s-off optical stimulation. After reconstruction, subject motion was corrected by a GPU based motion correction method (Fang et al., 2013).

The peak HRF amplitude was calculated for voxels that has an F-value larger than 4.42 (P<0.001) and overlaid the peak HRF amplitude map onto a high-resolution atlas MRI image (86) to enable precise anatomical localization of the activity. Since an equivalent fully-sampled high spatial resolution fMRI dataset could not be acquired due to fundamental limitations, the HSPARSE fMRI method was compared with the achievable highest spatial resolution Nyquist image with the same FOV and temporal resolution (NAcq). The SNR of the Nyquist and the HSPARSE images were approximately 30 dB and 25 dB, respectively. Therefore, three HSPARSE datasets were averaged to obtain a high-resolution image with the same SNR as the Nyquist image $(25+20 \log_{10}\sqrt{3} \approx 30)$.

Results 2.1 Optimal Regularization Parameters were Identified

Figure 10A:
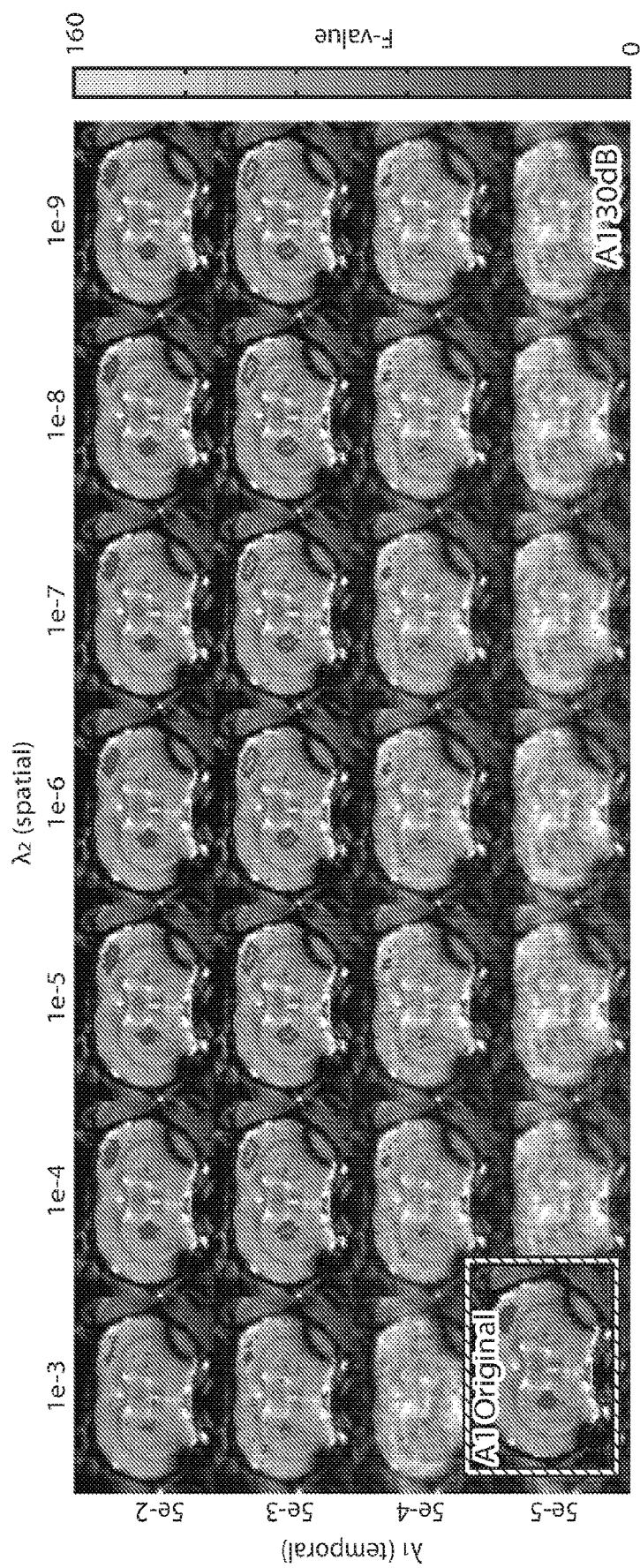
(FIG. 10A) Example reconstructed images of the A1 phantom (30 dB) with different regularization parameters. Voxels were considered to be active if they exhibit an F-value greater than 4.42 ($P<0.001$). Lower left plot shows the original ground-truth image.
Figure 10B:
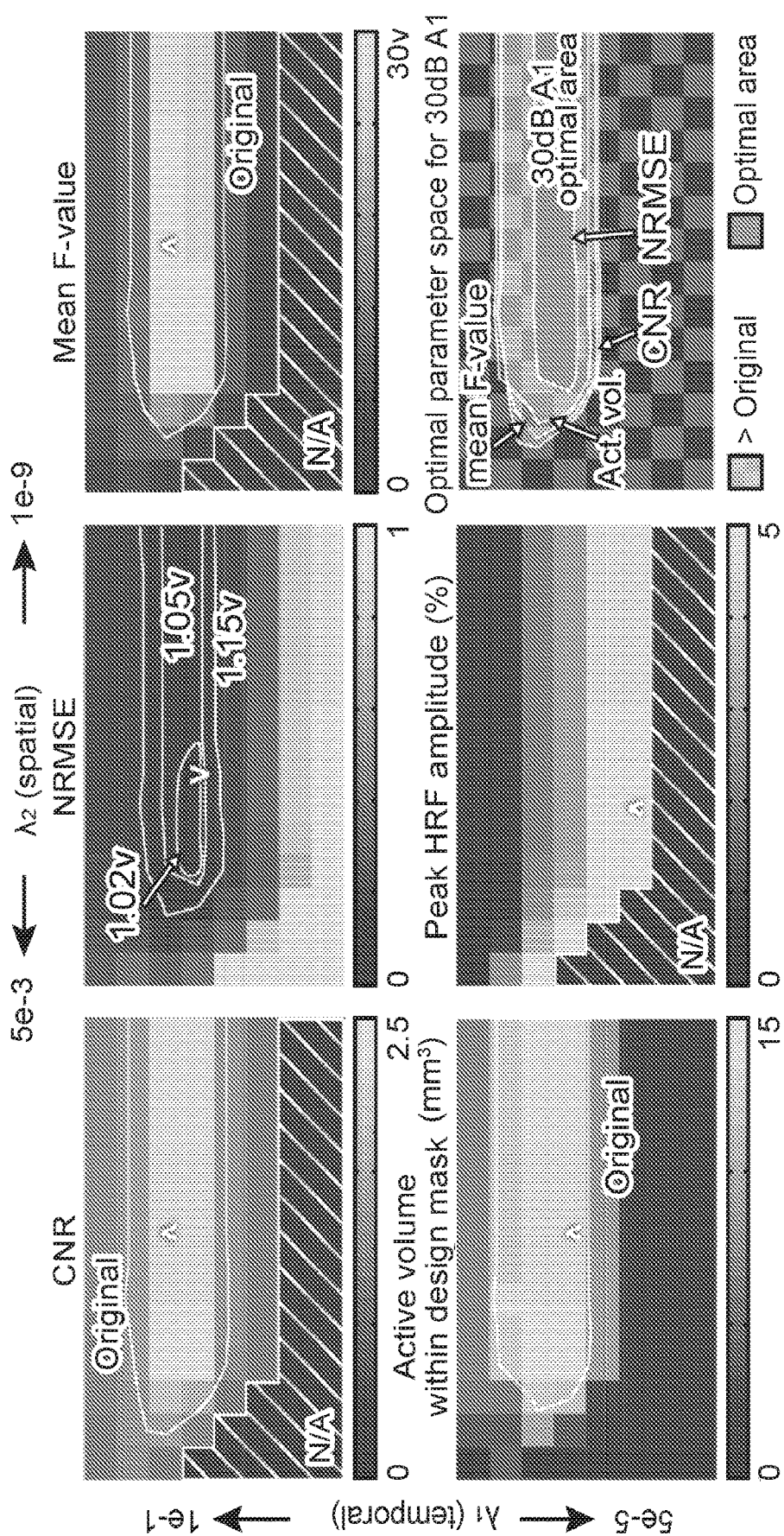
(FIG. 10B) An optimal regularization parameter range was defined as the region that achieved higher CNR and maximum correlation coefficient, larger active volume within the designed active region compared to the original ground-truth image, and NRMSE of less than 105% of the minimum NRMSE found within the search range. A range of regularization parameters were identified to yield high reconstruction quality (lower right plot, blue area) for the 30 dB A1 phantom. The symbols '^' and 'v' in each plot indicate the maximum and minimum values in the corresponding test, respectively. "N/A" indicates an area in which CNR, maximum correlation coefficient, and peak HRF amplitude cannot be computed due to limited activation. 1.02v, 1.05v and 1.15v indicate the contour lines of 1.02, 1.05, and 1.15 times the minimum NRMSE value.

The role of the regularization parameters was first assessed on the 30 dB A1 phantom reconstruction. As shown in FIG. 10A, the reconstructed image quality and fMRI signal depends significantly on the choice of the temporal and spatial regularization parameters. As shown in FIG. 10B, although the reconstructed peak HRF amplitude generally decreased for all tested regularization parameters, it was found that parameter ranges resulted in higher CNR, mean F-value, and larger active volume within the original designed region than the ground-truth phantom. When these ranges were overlaid, a parameter range was identified for $\lambda 1$ between $1e^{-2}$ and $5e^{-3}$ and $\lambda 2$ between $1e^{-4}$ and $1e^{-9}$ (blue area in FIG. 10B lower right—white arrow) that maximizes the CNR, mean F-value, and the active volume within the original designed active region with low NRMSE. Therefore, it was concluded that this range of parameters was optimal for this phantom.

Figure 10C:
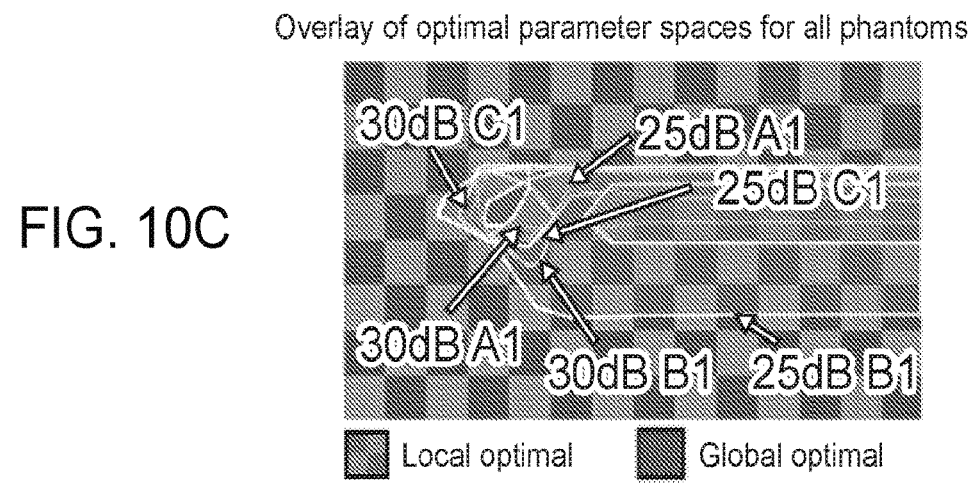
(FIG. 10C) The optimal ranges for 6 phantoms with different base images, activation patterns and SNRs were overlaid, where a set of regularization parameters were found to provide optimal reconstruction quality for all phantoms tested.
Figure 10D:
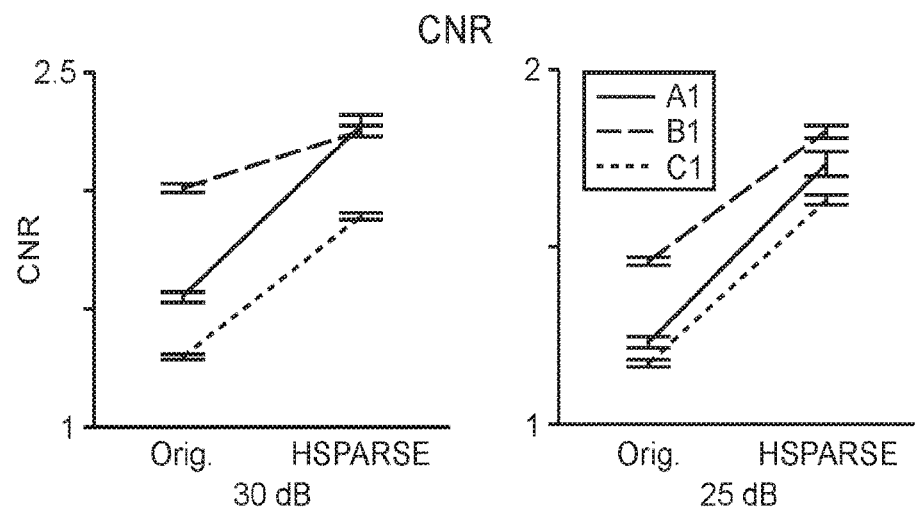
(FIG. 10D-H) With a set of parameters (=5e-3 and =1e-4) selected from the optimal range, CNR, the active volume within the original ground truth active region, and the maximum correlation coefficient of the reconstructed image were higher than the original phantom with noise, and the NRMSE was less than 0.24 across all phantoms. Although the HRF amplitudes decrease after the CS fMRI reconstruction, the CS fMRI was shown to maintain the relative amplitudes and shapes of HRFs in FIG. 11.
Figure 10E:
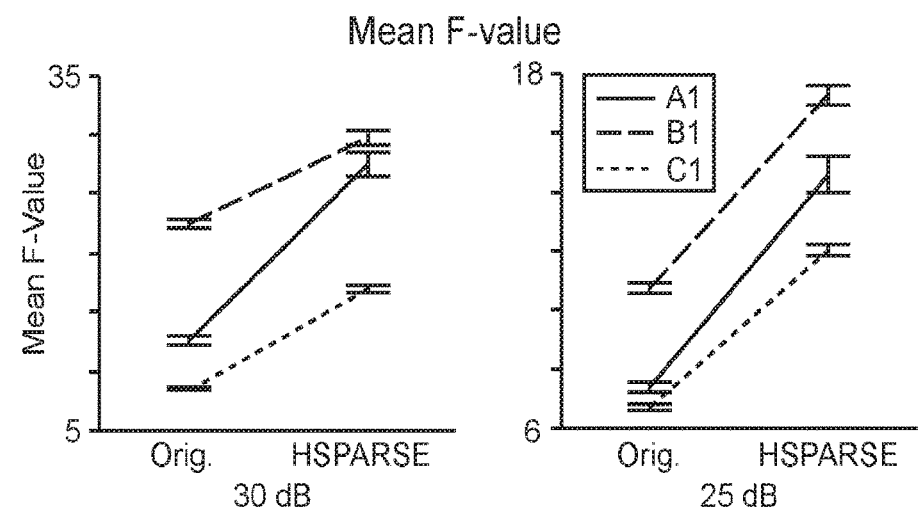
Figure 10F:
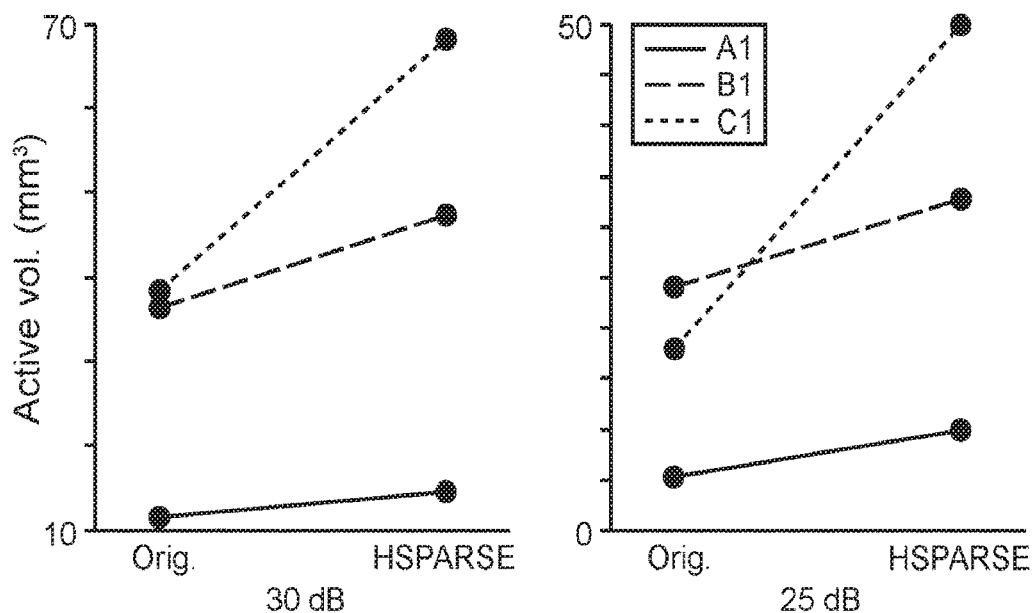
Figure 10G:
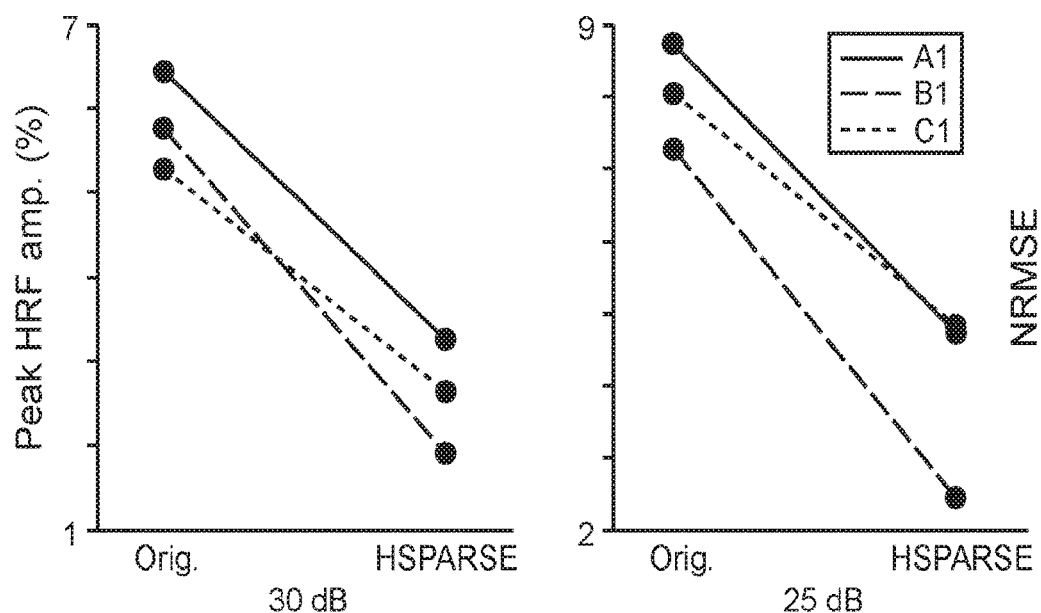
Figure 10H:
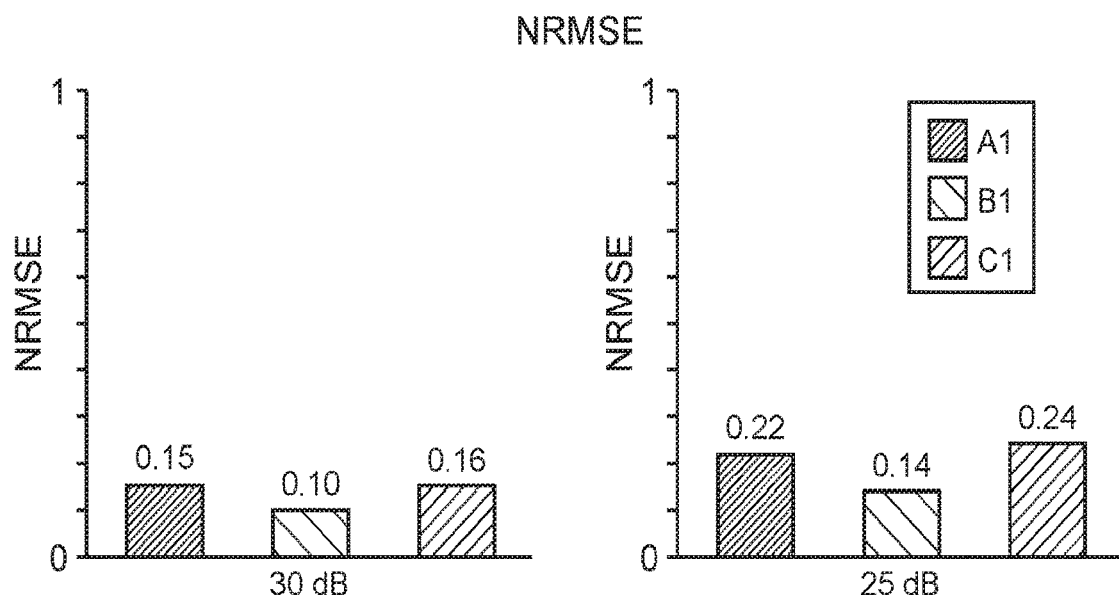
Figure 10I:
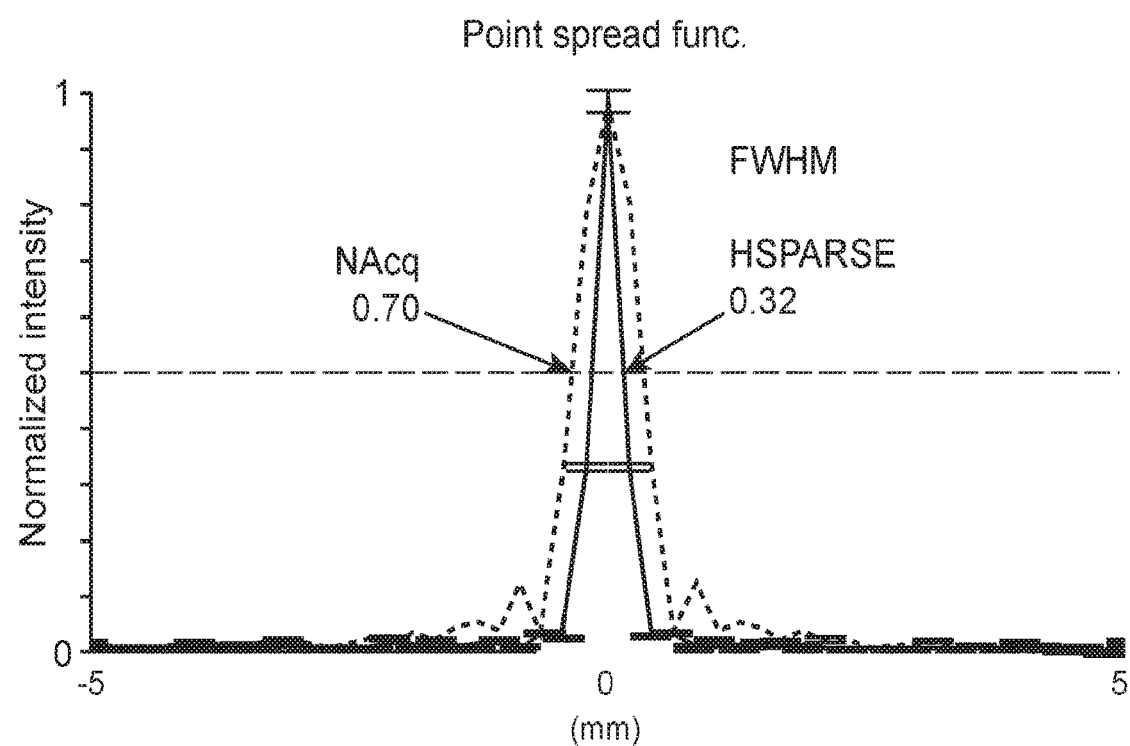
(FIG. 10I) FWHM of the point spread function was 0.70 mm with the highest spatial resolution Nyquist acquisition while it reduced to 0.32 mm for HSPARSE reconstructed images with optimal regularization parameters. The error bar shows the standard deviation of the CS point spread function across temporal frames.

The same tests were performed at higher noise levels (25 dB) and with different base images (B1 phantom) and activation patterns (C1 phantom) (FIG. 5A). A common range was identified (dark blue range in FIG. 10C—black arrow) where all the optimal ranges for different phantoms overlapped. For example, for $\lambda 1=5e^{-3}$ and $\lambda 2=1e^{-4}$, which was within this range, CNR improves by 12 to 47%, mean F-value by 33 to 117%, active volume by 36 to 178%, and the NRMSE was less than 0.24. (FIG. 10D-H). The point spread function FWHM also decreased from 0.70 mm for the highest spatial resolution Nyquist image to 0.32 mm (FIG. 10I) for the HSPARSE image with the optimal regularization parameters. Although the average peak HRF amplitude was reduced, it was later shown that the HRF shape and relative amplitude was maintained after reconstruction.

2.2 High Sensitivity and Low False Positive Rate

Figure 6C:
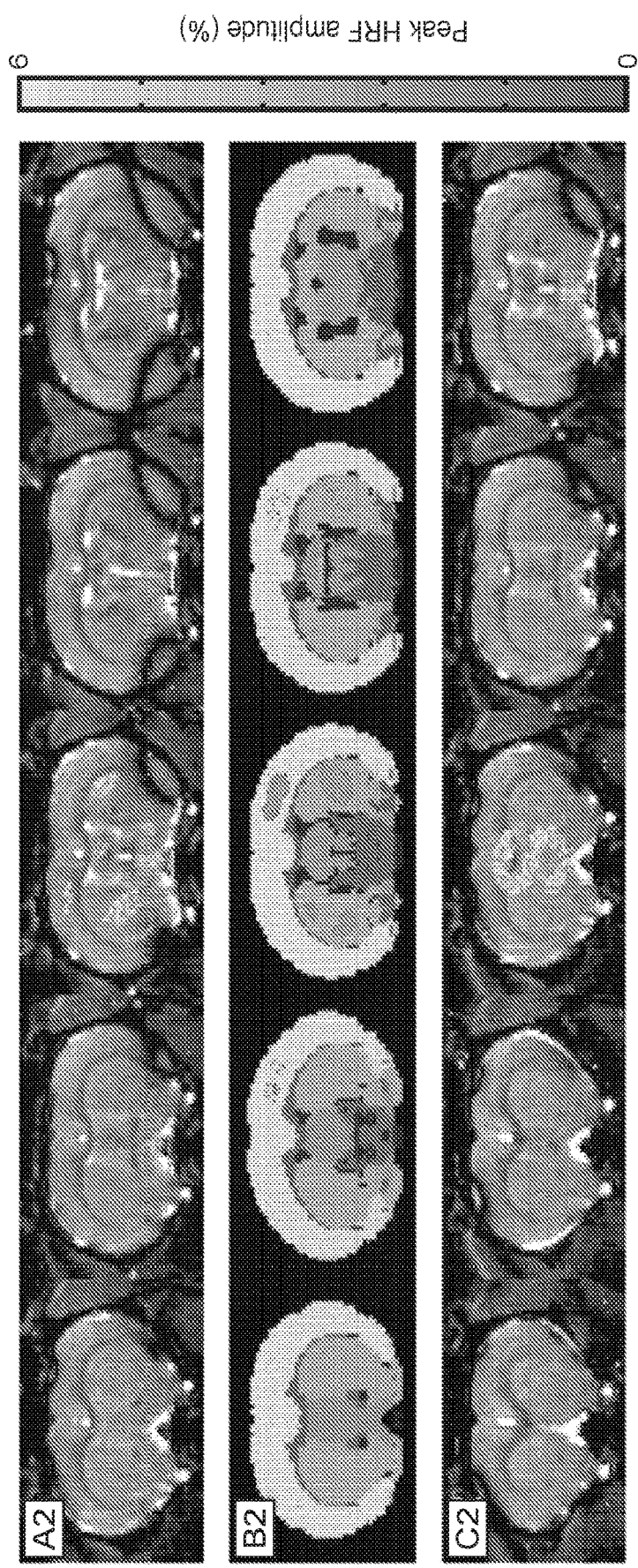
(FIG. 6C) Example reconstructions of the A2-C2 phantoms with 10% peak HRF amplitude show that the reconstructed fMRI signals were mainly confined to the designed active area with limited false positive activations outside.

The sensitivity (FIG. 6A) and FPR (FIG. 6B) was evaluated using the 30 dB A2, B2 and C2 phantoms (FIG. 5B) at four different peak HRF amplitudes (10-4%, corresponding to CNR of 2.55-1.23). Example reconstructions of the three phantoms with 10% peak HRF amplitude were shown in FIG. 6C. It was found that the activities were localized to the original volume of activation and the false positive signals were limited. As shown in FIG. 6D, the sensitivities of the HSPARSE reconstructed datasets were found to be 69 to 99% of the original datasets on average. It was also found that the FPRs were small on all perimeter layers and across all tested peak HRF amplitudes, e.g. the FPRs on the 1-pixel perimeter layer (FPR1) were less than 0.051 and the FPRs on the 2-pixel perimeter layer (FPR2) were less than 0.01. Because the single-slice activity patterns were designed for testing under the most difficult conditions, higher sensitivity and lower FPR was expected in real applications. Taken together, these data indicated that the HSPARSE reconstruction yielded high sensitivity than the ground-truth image with a low FPR.

2.3 Low HFR Distortion

Figure 11A:
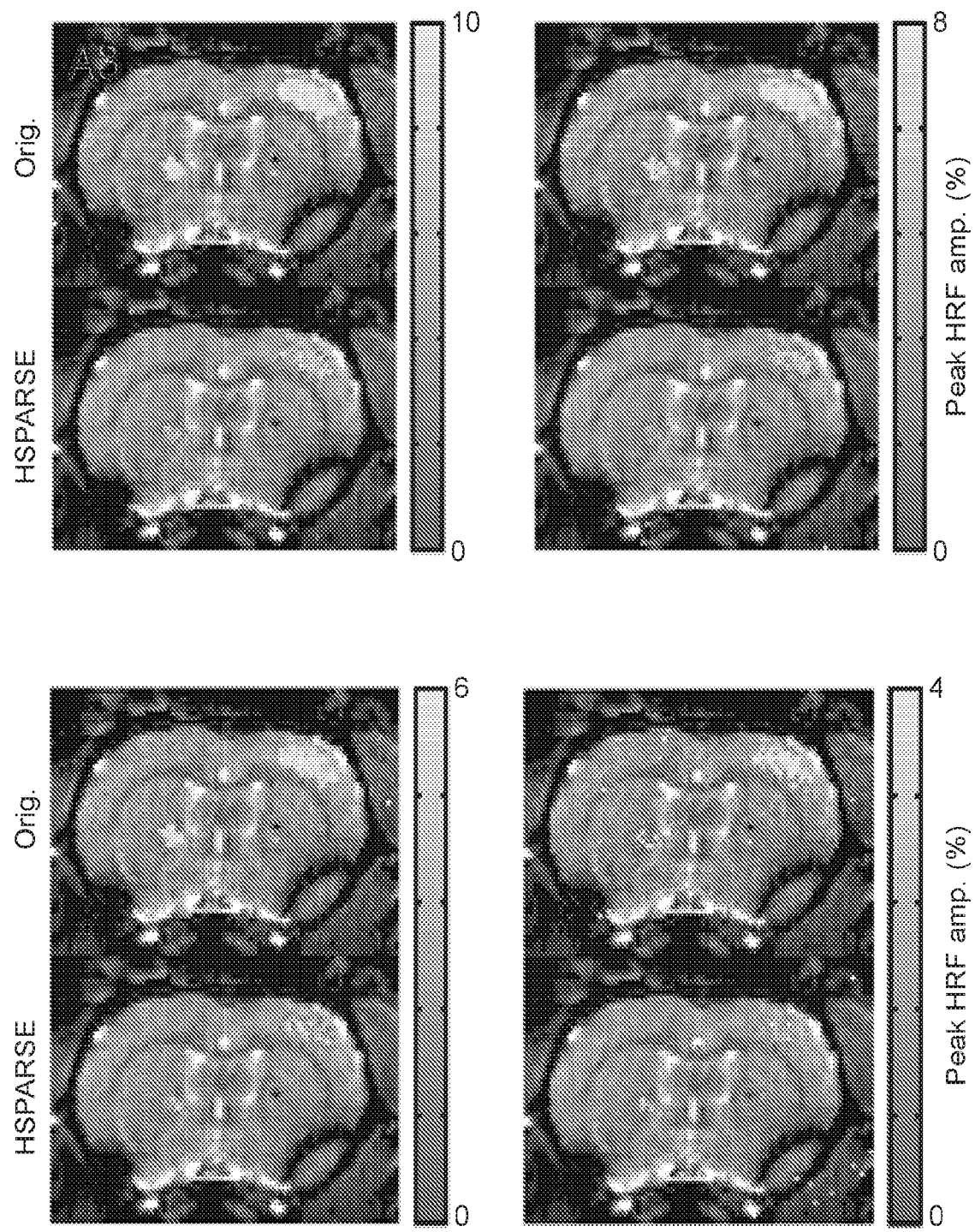
(FIG. 11A) Representative images of the reconstructed A3 phantom were shown with original HRF amplitudes of 4, 6, 8, and 10%. All phantoms were reconstructed 5 times with independent identical Gaussian distributed noise using regularization parameters ($\lambda=5e-3$ and $\lambda 1=1e-4$) within the optimal range.
Figure 11B:
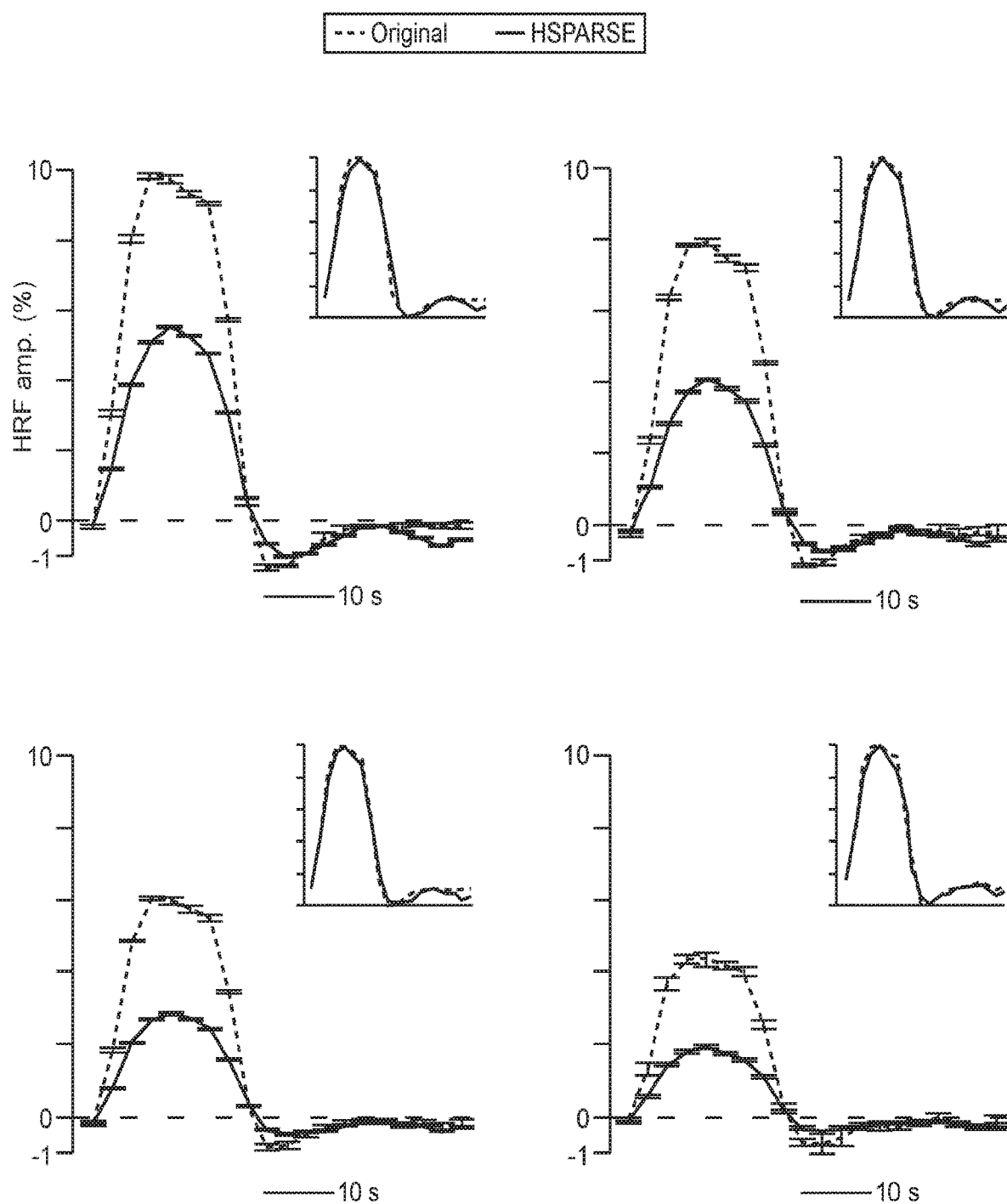
(FIG. 11B) Although the HSPARSE reconstructed HRFs exhibit lower amplitudes than the original HRFs for all tested amplitudes, the HRF shapes were similar after amplitude normalization (inset on upper right). Error bars represent standard deviation across 5 reconstructions.
Figure 11D:
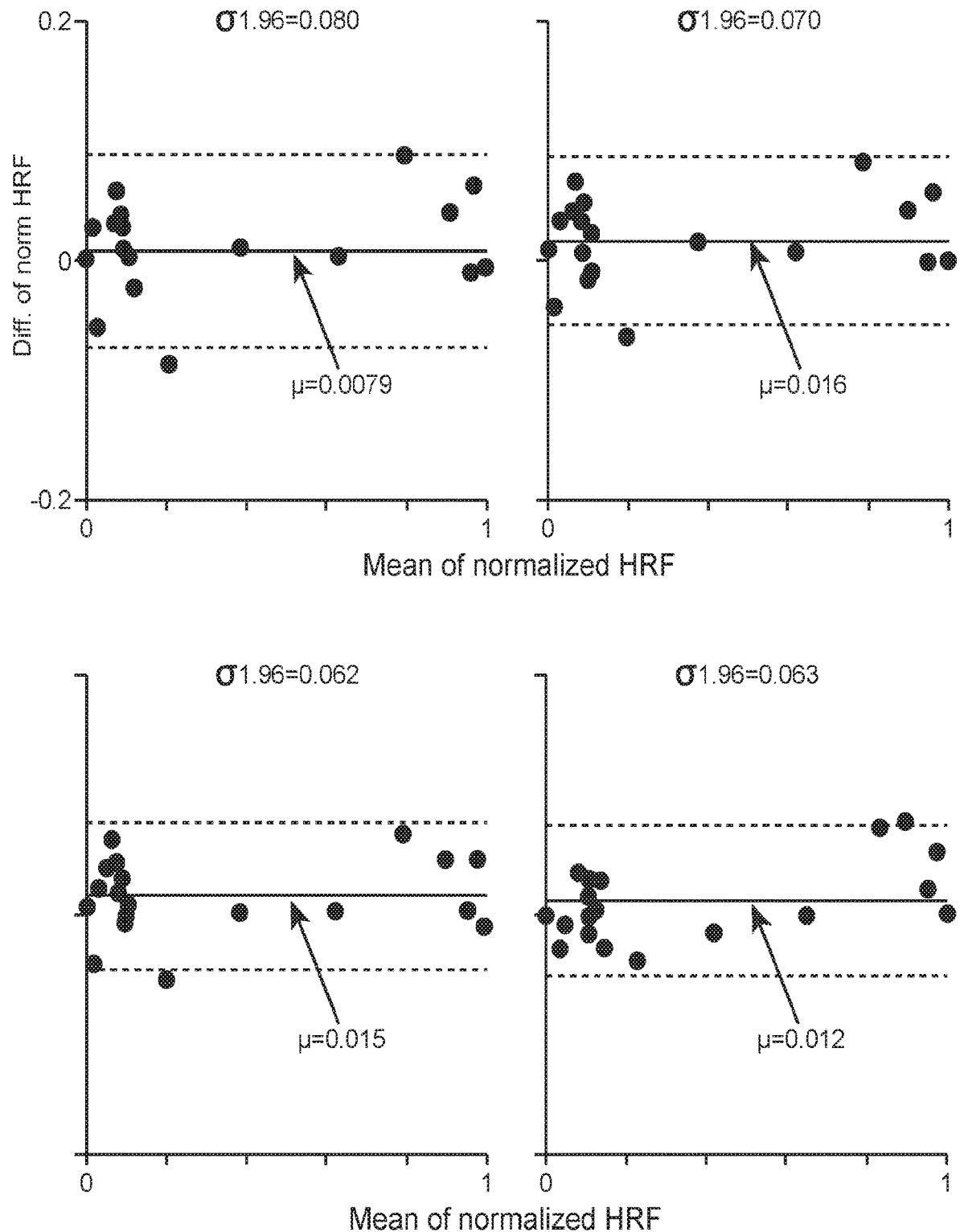
(FIG. 11D) After the amplitude normalization of all HRFs, the maximum mean difference between the HSPARSE reconstructed and the original HRFs was less than 0.016 and the limits of agreement (±1.96×standard deviation) were less than 0.080.

The temporal distortion of the HSPARSE fMRI method was investigated with a range of HRFs (peak amplitudes of 10-4%) typically observed in in vivo experiments (FIG. 11A). As shown in FIG. 11A, 11B, although the HRF amplitude was reduced, the HRF shape was maintained with the HSPARSE reconstruction. The HSPARSE reconstructed HRF amplitudes exhibited strong linear correlation with the original HRF amplitudes (R2=0.98, FIG. 11C), indicating that the HSPARSE reconstruction linearly scaled the original HRF with little distortion to the HRF shape. HRF normalization also confirmed that the temporal dynamics were well preserved following the HSPARSE reconstruction, i.e., mean differences between normalized HRFs were less than 0.016 and limits of agreement (1.96×standard deviation) were less than 0.08 (FIG. 11D) across all tested peak HRF amplitudes.

Figure 11E:
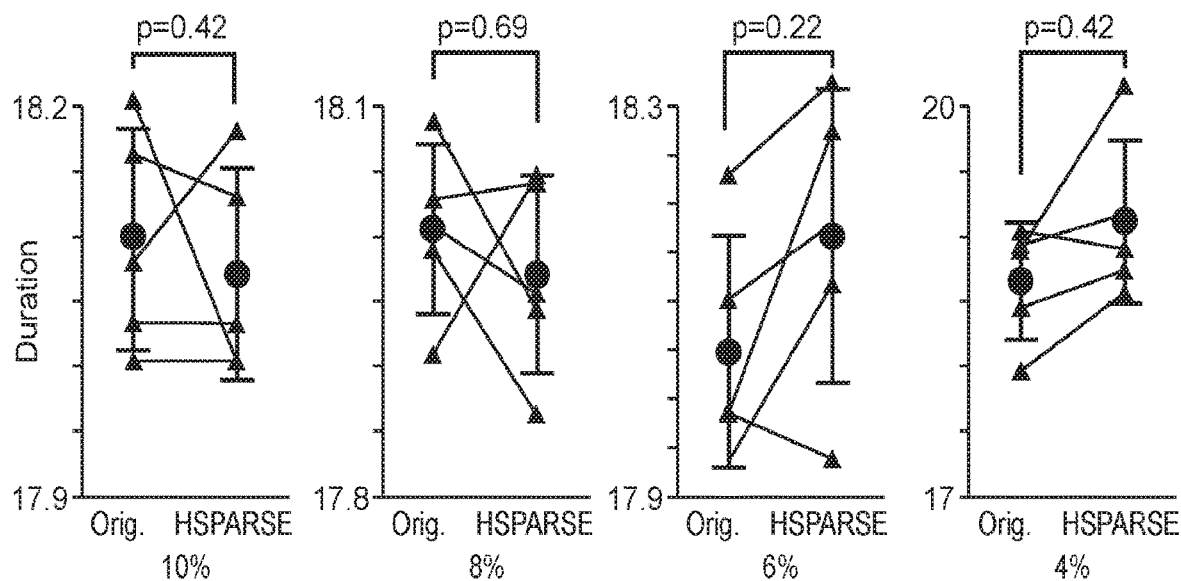
(FIG. 11E, 11F) Similarly, the durations of the HSPARSE reconstructed HRFs were not significantly different from the original HRFs ($P>0.22$, Wilcoxon ranksum test), and maximum time-to-peak differences (2.40 s) was smaller than the 3 s temporal resolution of the fMRI acquisition. Similar results were seen in B3 and C3 phantoms.
Figure 11F:
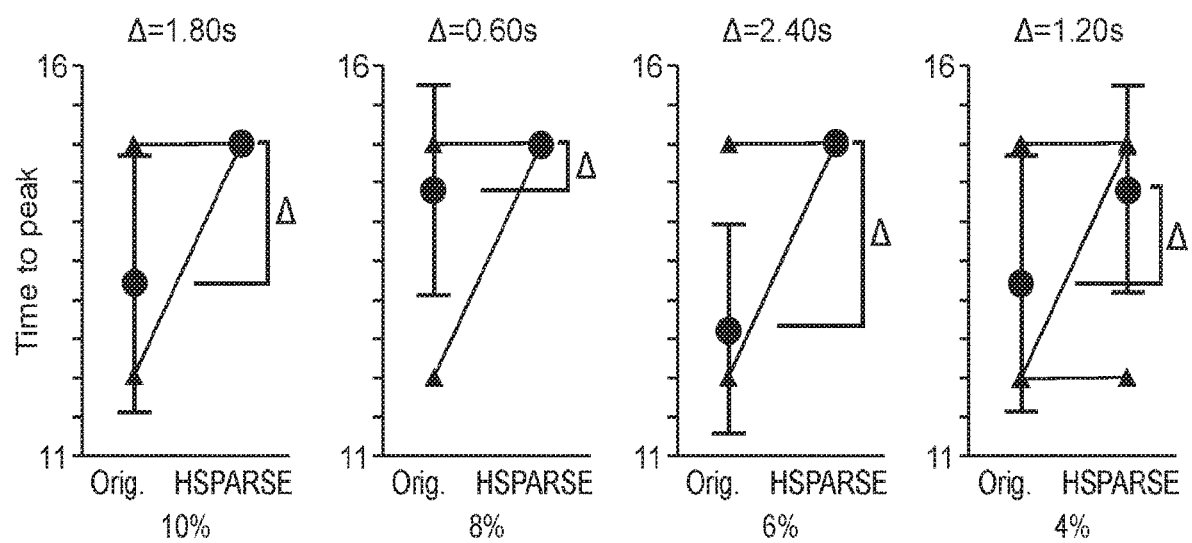

HRF characteristics such as the duration of activation and time-to-peak were also compared. The activity duration of the A3 phantom was not significantly different between the original and the HSPARSE reconstructed images for any of the four tested HRF amplitudes (FIG. 11E, Wilcoxon rank-sum test). For time-to-peak, the maximum mean difference between CS and the original signal of the A3 phantom was 2.4 s (FIG. 11F). Because this time-to-peak difference was less than 3 s, which was the temporal resolution of the data acquisition, the differences could simply be a result of having a limited temporal resolution. Similar results were also observed for the B3 and C3 phantoms.

2.4 Robust against Physiological Noise

Figure 12B:
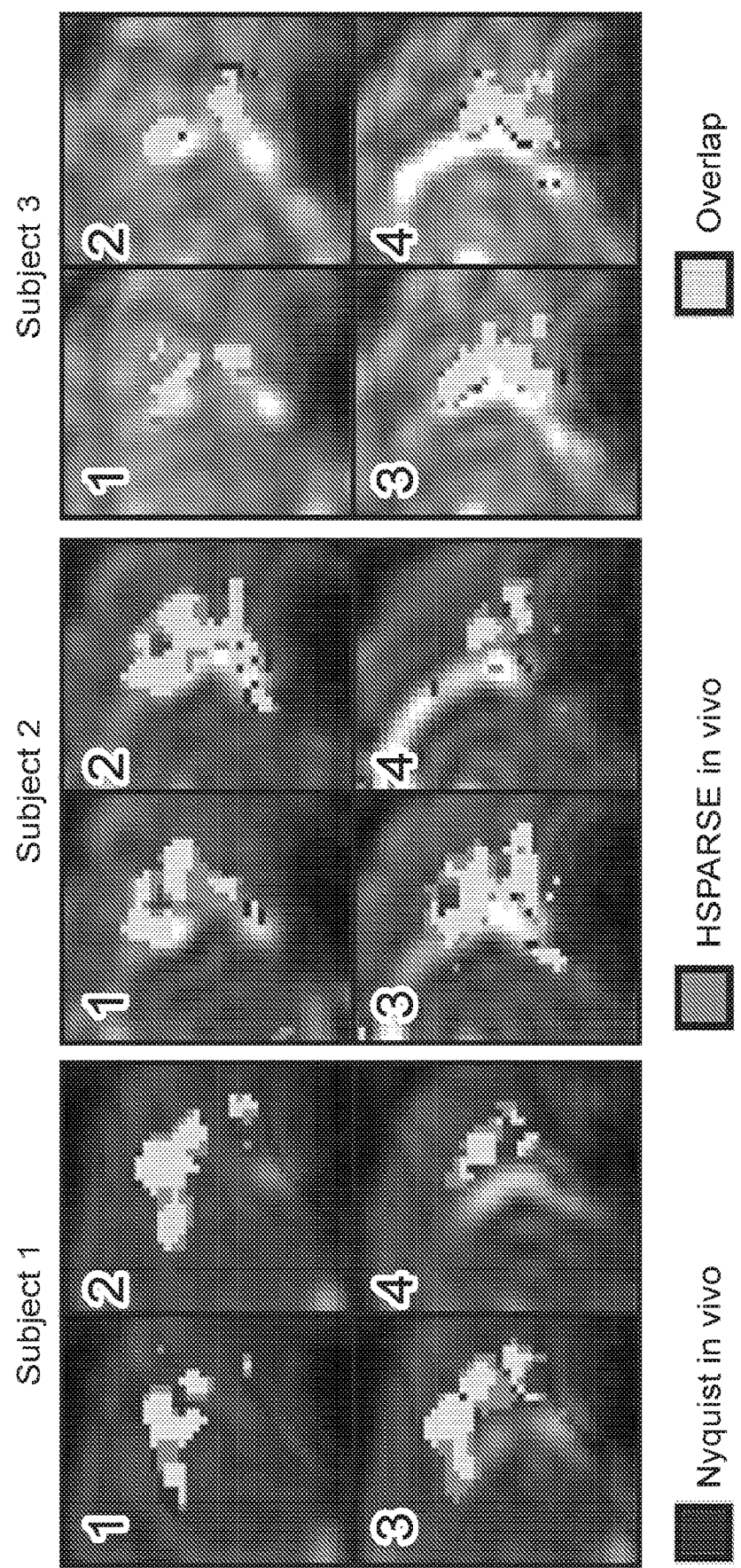
(FIG. 12B, 12C) The images reconstructed with HSPARSE detect the majority of the activity and the active voxels shared between the HSPARSE reconstructions and the fully-sampled images consist 90.3 to 93.0% of active voxels from the fully-sampled images. Because the ground-truth active region was not available for the in vivo experiment, additional active voxels only detected with HSPARSE reconstruction could either be false positive signal or a result of improved sensitivity due to CNR increase. However, active voxels only detected with HSPARSE reconstruction was limited within the 1-pixel perimeter layers of the active volume detected with the fully-sampled dataset.
Figure 12C:
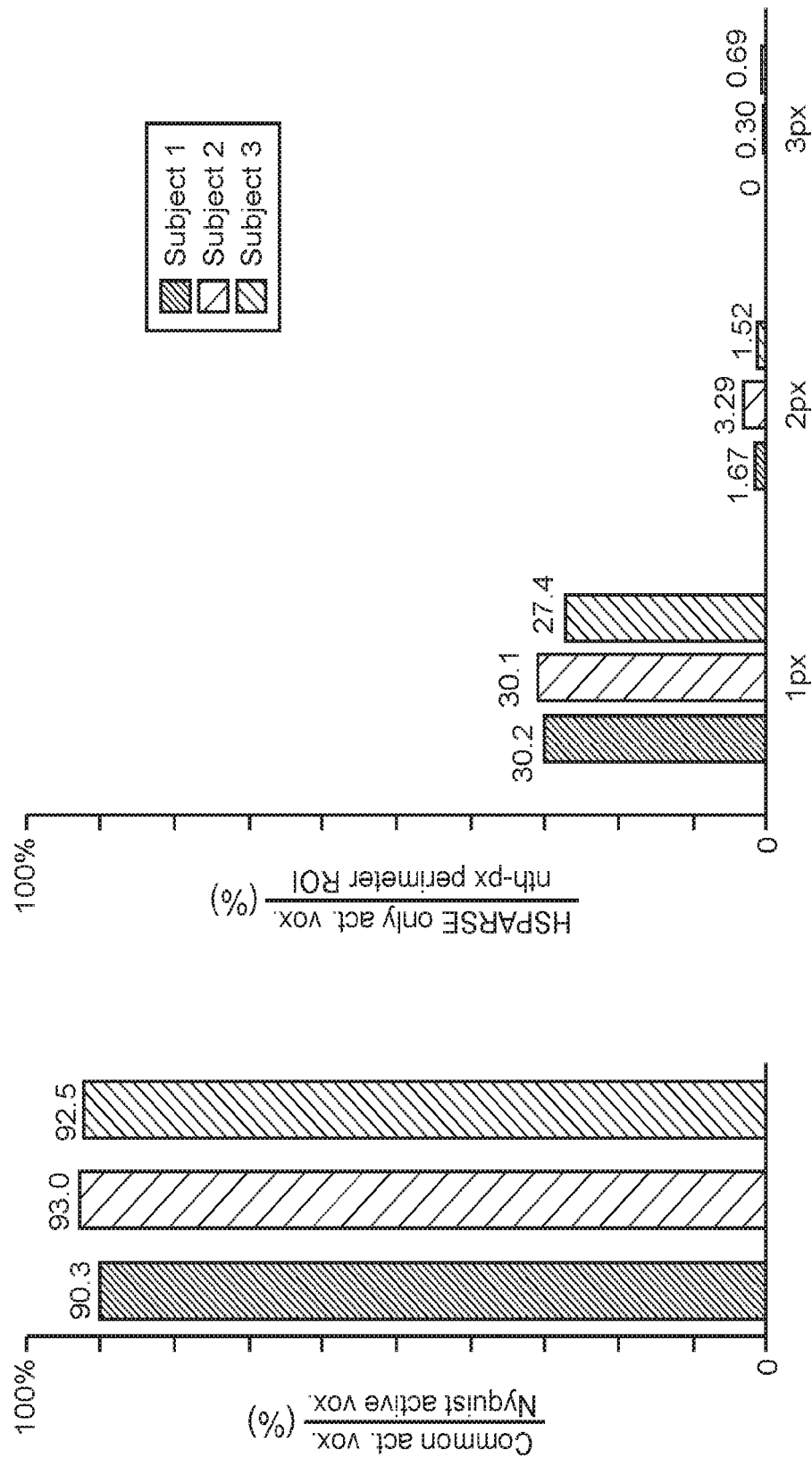
Figure 12D:
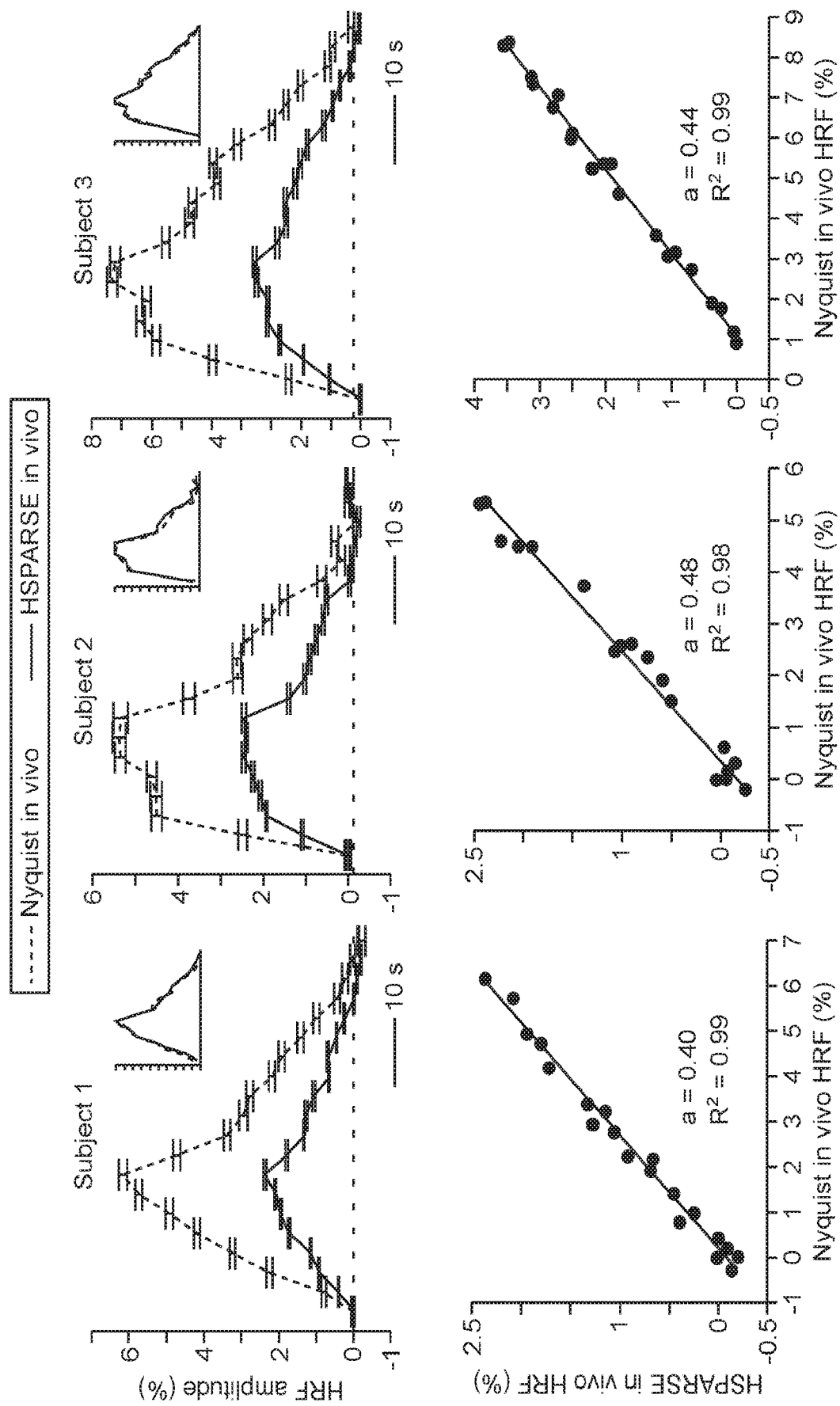
(FIG. 12D) HRF amplitude reduction from HSPARSE reconstruction has a scaling factor ranging from 0.40 to 0.48. Importantly, the HRFs from the fully-sampled datasets and the HSPARSE reconstructions had a strong linear correlation with a minimum correlation coefficient (R2) of 0.98, demonstrating that HSPARSE reconstruction maintains the temporal characteristics of the fully-sampled HRFs.
Figures 13, 14A:
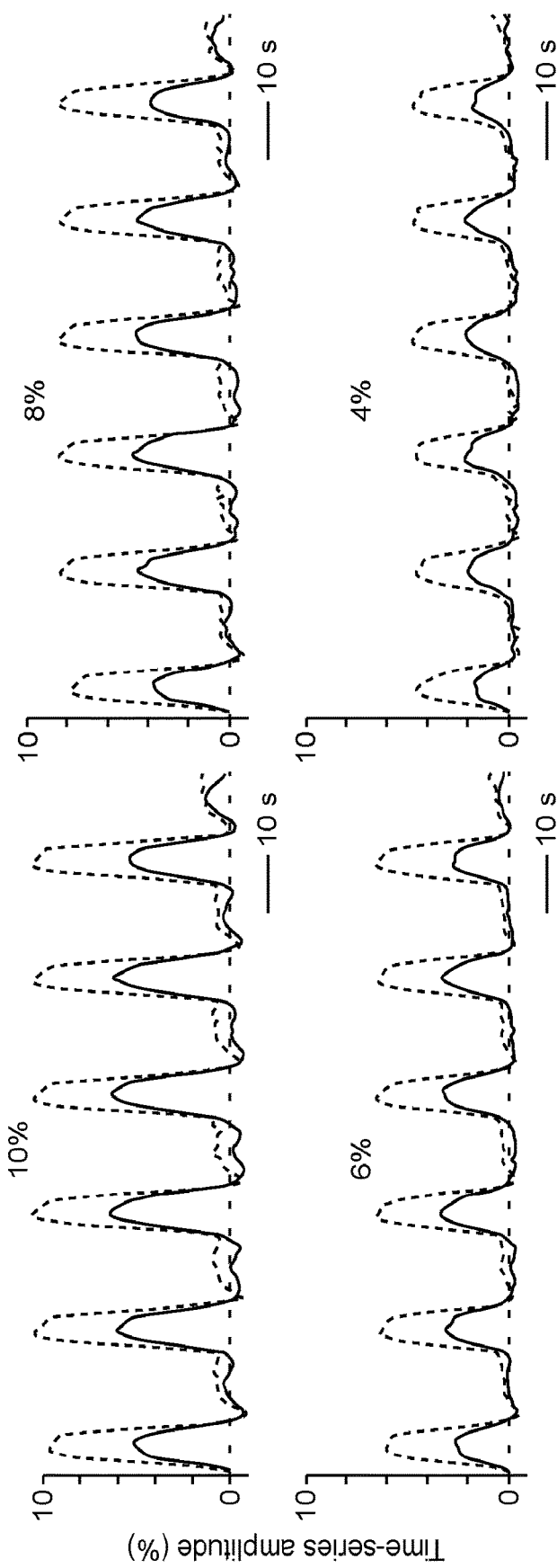
FIG. 13: Comparison of temporal HRF characteristics between the original fully-sampled and HSPARSE images in the presence of physiological noise. For all three subjects, the HRF durations were similar and the maximum duration difference was 1.67 s. The first subjects gave the same time-to-peak. The rest two subjects showed an increase in time-to-peak for the HSPARSE reconstructed image, but the difference was smaller than the 3 s temporal resolution of the acquisition.
(FIG. 14A, 14B) Six-cycle time-series corresponding to FIGS. 11 and 12. Similar to the analysis performed on the HRFs, the HSPARSE reconstructed six-cycle time-series also show a strong linear correlation with the original ground-truth time-series, which indicates the HSPARSE method maintains high temporal fidelity.
Figure 14A:
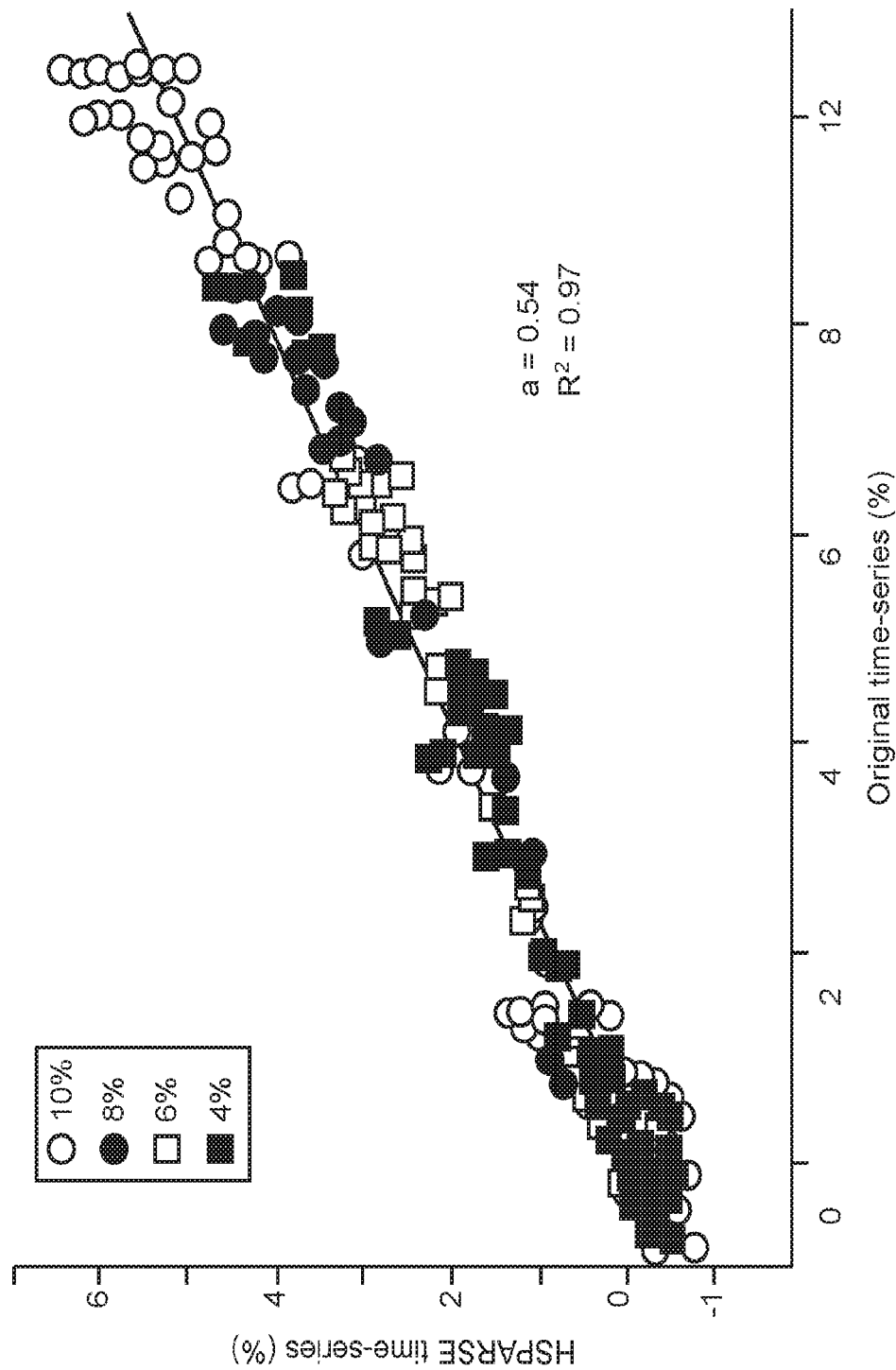
Figure 14B:
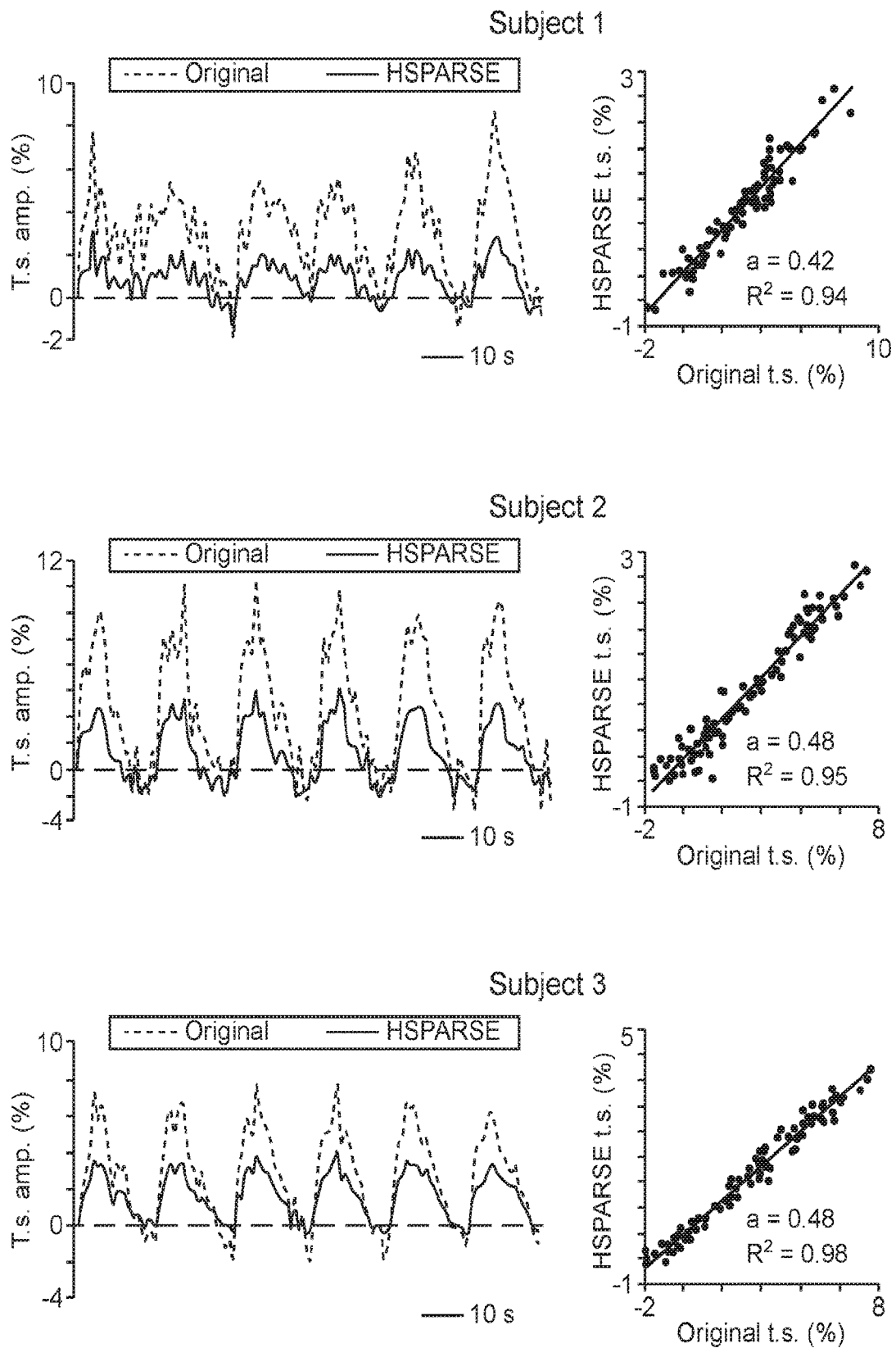
Figure 14C:
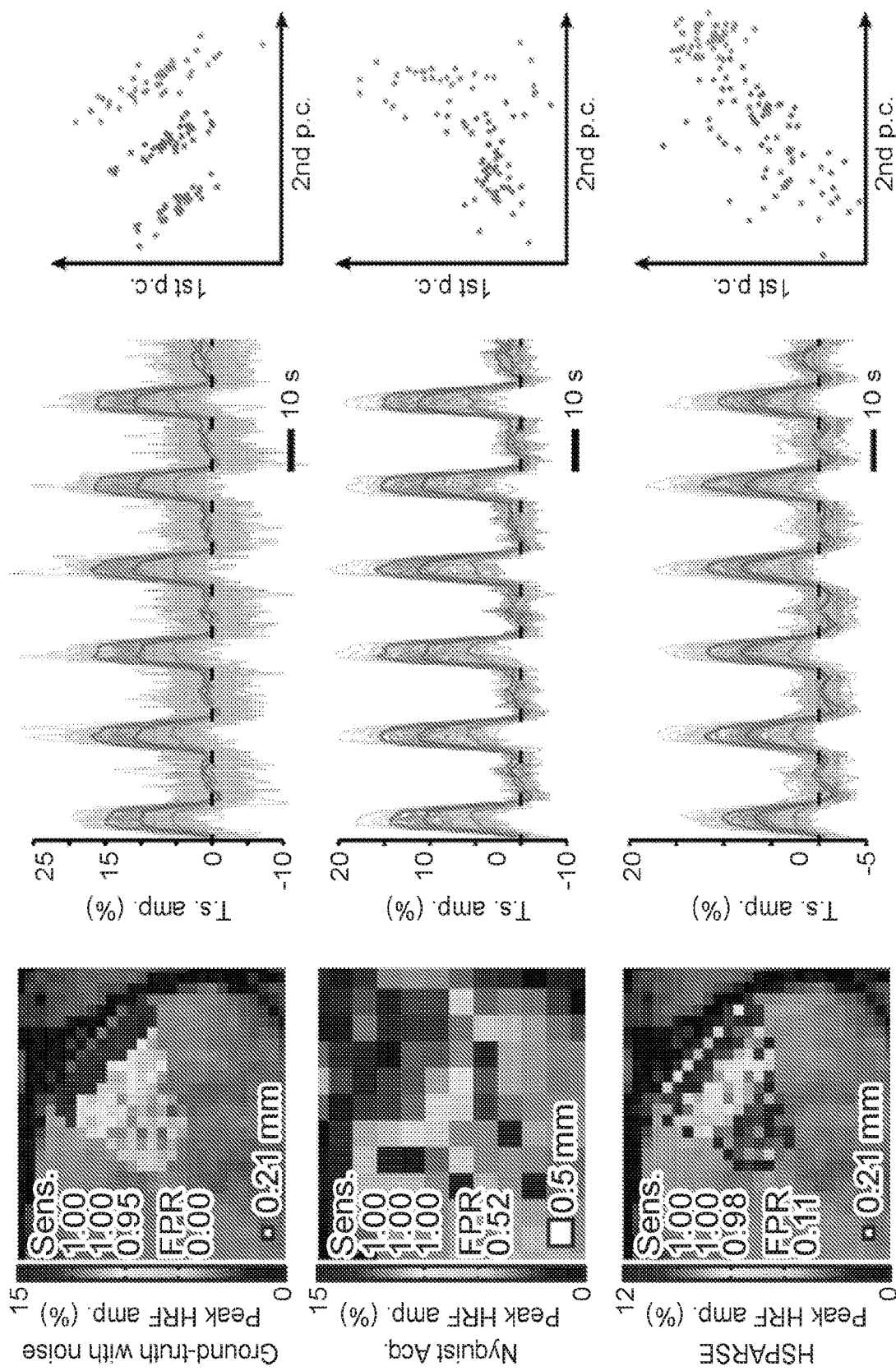
(FIG. 14C, 14D) Six-cycle time-series corresponding to FIG. 7 and FIG. 8. While some sinusoidal variations in the HSPARSE fMRI reconstructed time-series were observed (bottom left plot for both C and D), the HSPARSE fMRI was found to preserve the peak amplitude and latency differences between layers, while the highest spatial resolution Nyquist acquisitions fail. HSPARSE also maintains high sensitivity and low FPR. In contrast, Nyquist acquisitions result in high FPR, which could be the result of low spatial resolution induced partial volume effects.
Figure 14C:
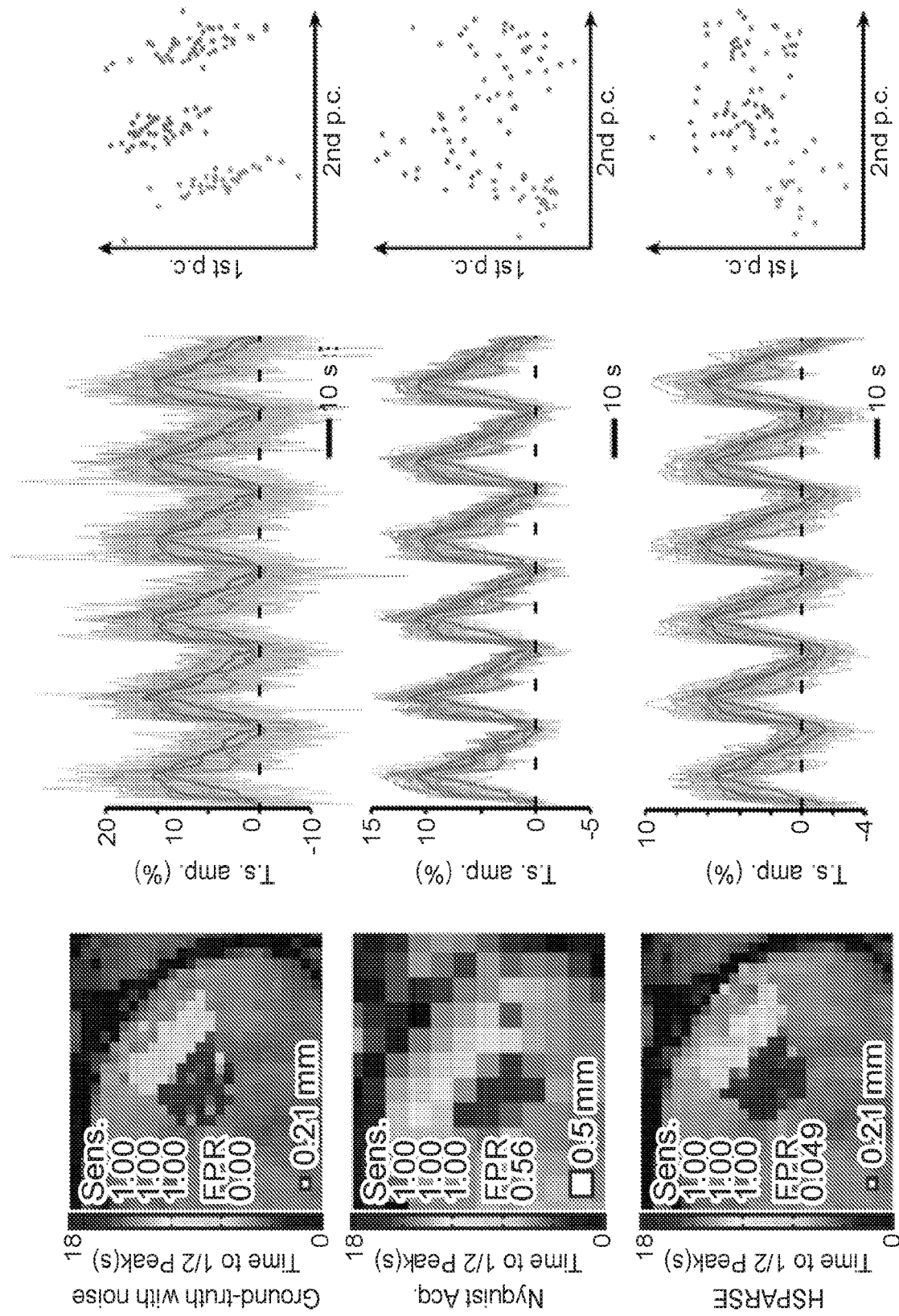
Figure 14D:
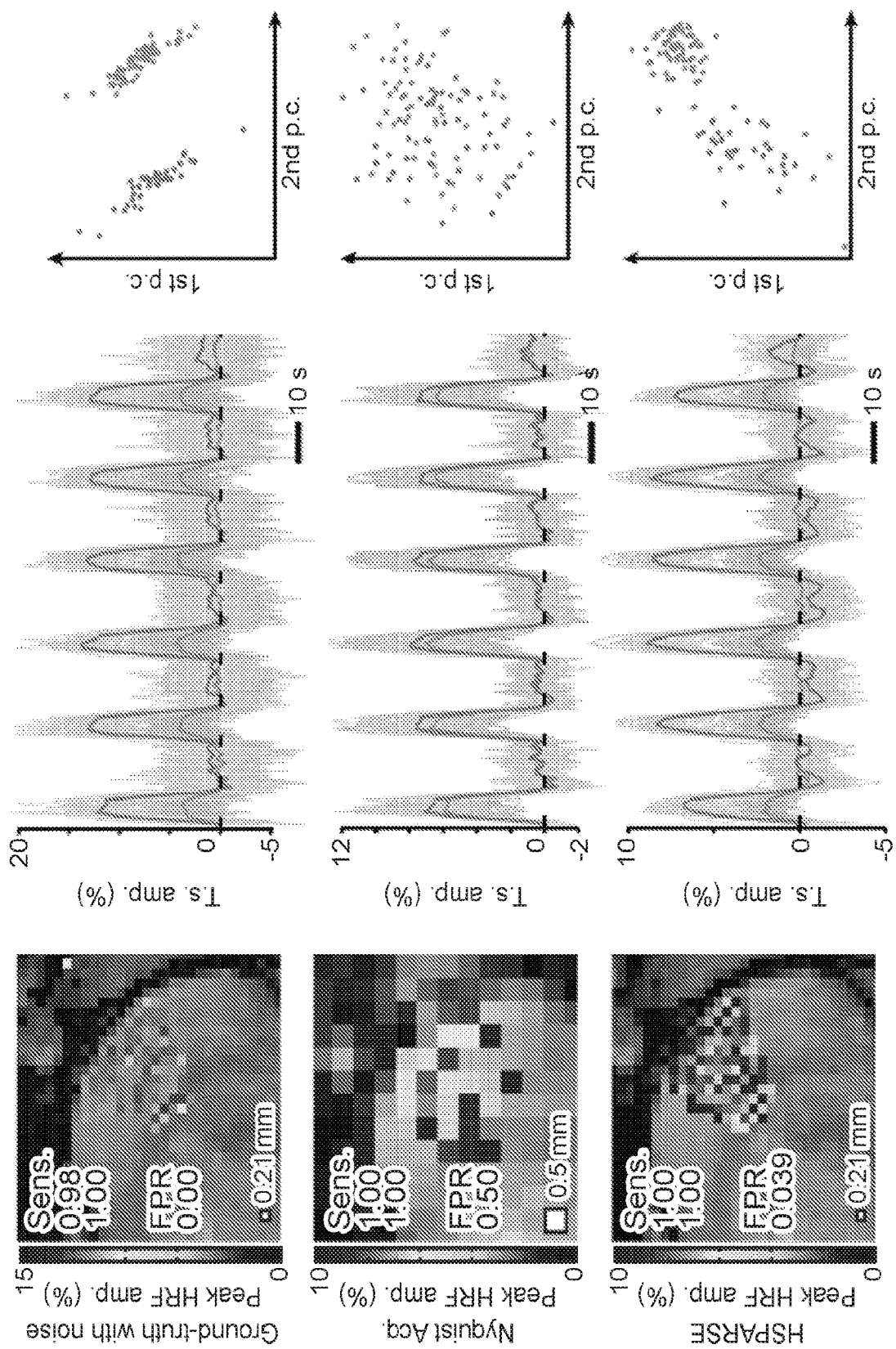
Figure 14D:
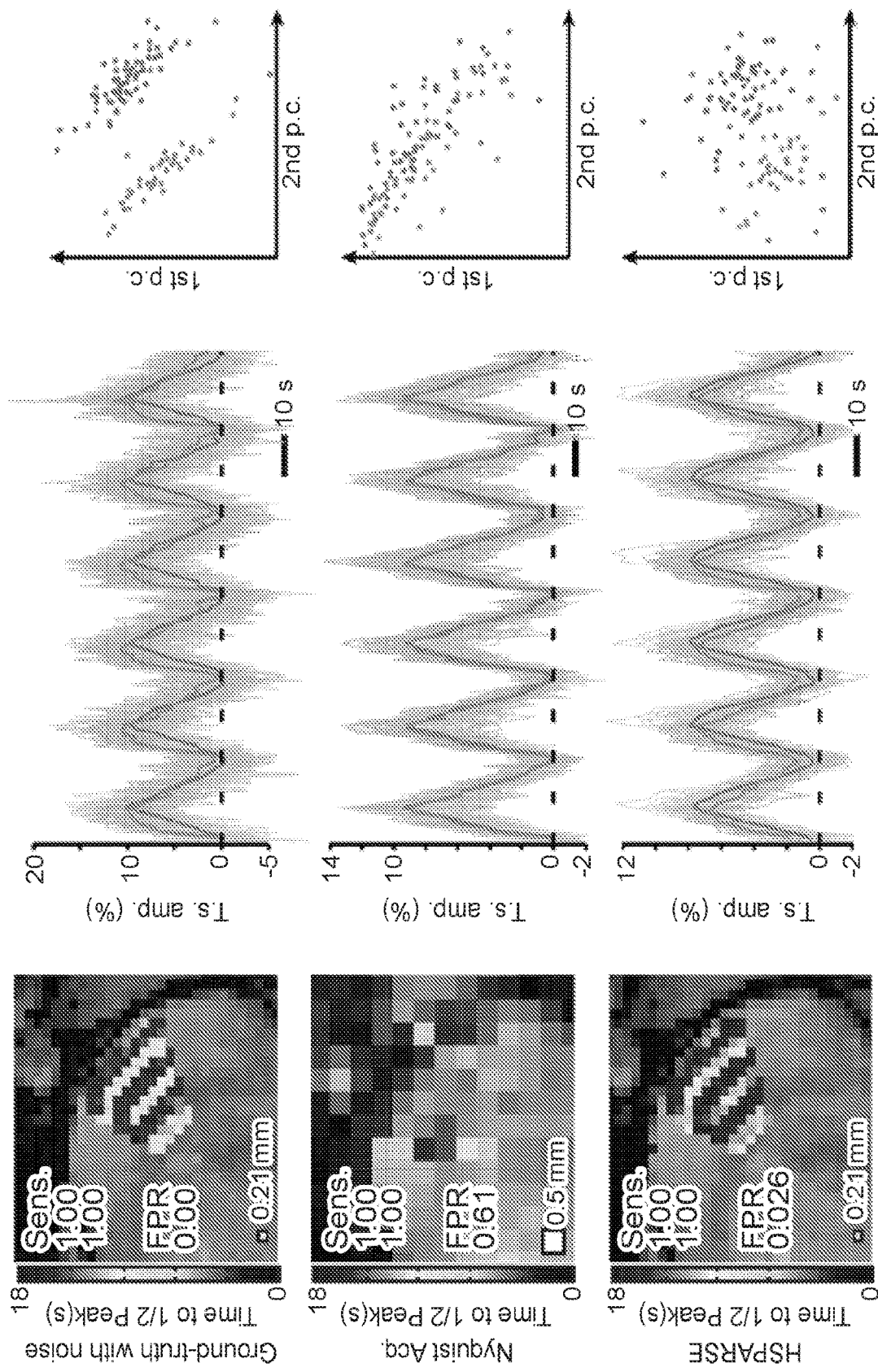
Figure 14E:
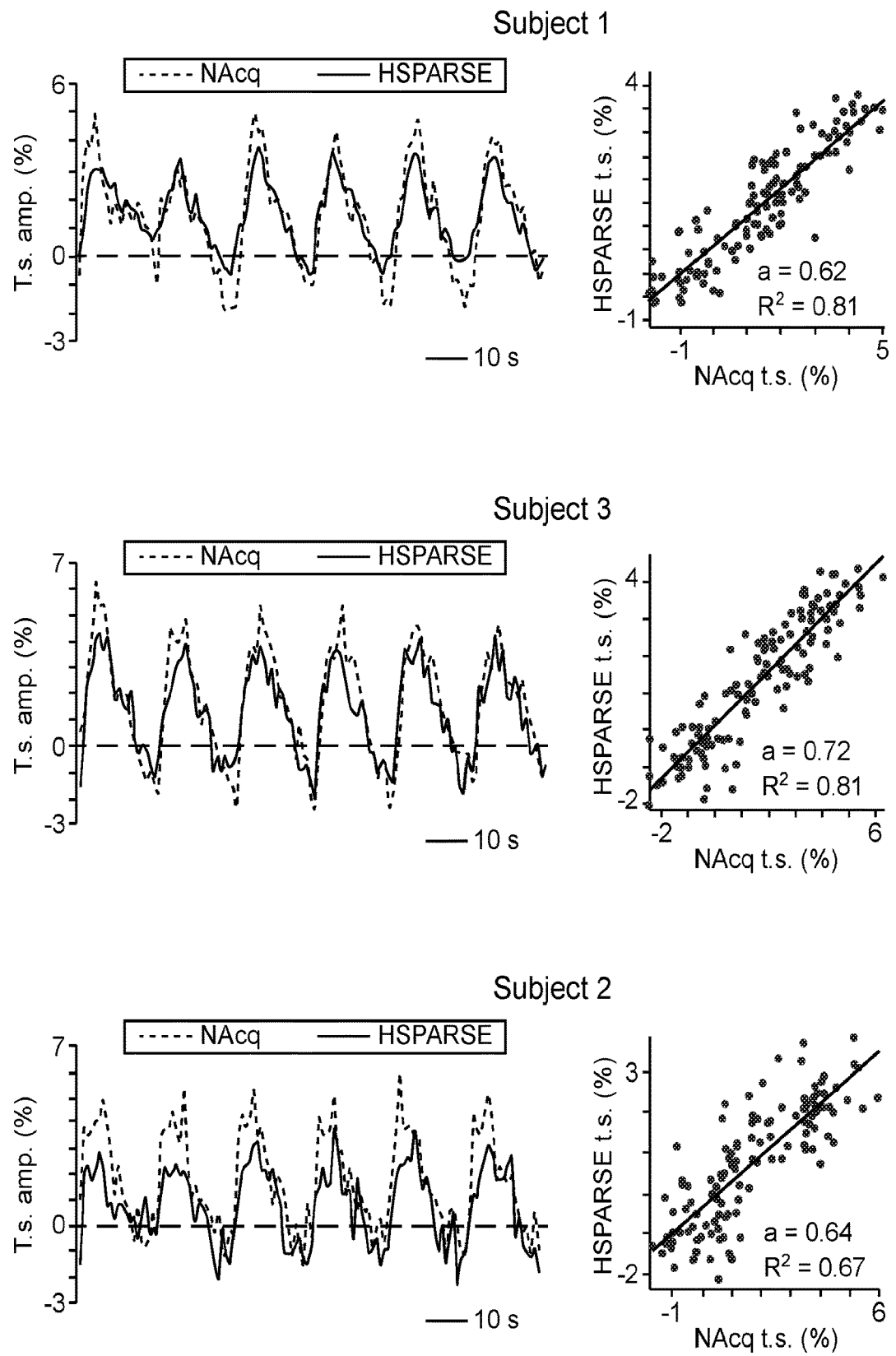
(FIG. 14E) Six-cycle time-series corresponding to FIG. 9. In vivo acquired HSPARSE fMRI six-cycle time-series also showed strong linear correlation with the time-series obtained from the highest spatial resolution Nyquist acquisitions for all three subjects, demonstrating that HSPARSE fMRI can provide high temporal fidelity for in vivo experiments.

Here, the fully-sampled datasets were compared with real physiological noise to their corresponding 5.3 times under-sampled HSPARSE images. As shown in FIG. 12A, consistent increases in CNR, mean F-value, and active volume were observed following the HSPARSE reconstructions. The NRMSEs between the HSPARSE reconstructed and the fully-sampled in vivo datasets were lower than 0.081 across subjects. The HSPARSE reconstructed datasets detect most of the activity in the fully-sampled datasets (FIG. 12B). The common active voxels in both images were 90% to 93% of the active voxels in the fully-sampled images (FIG. 12C). Additional active voxels were also observed in the HSPARSE reconstructed datasets. Because the ground-truth active region was not available for the in vivo datasets, these additional active voxels could either be false positive detections or a result of the improved CNR. Importantly, these signals were within the 1-voxel perimeter layer of the original active region across all subjects, indicating the HSPARSE activity localization was consistent with the fully-sampled image. The HSPARSE reconstructed HRFs was linear to the fully-sampled HRFs and the correlation coefficients were larger than 0.98 (FIG. 12D). Measures of the activation duration and time-to-peak also confirmed that the HRFs from the fully-sampled images and the HSPARSE reconstruction were close (FIG. 13).

2.5 Resolves High Spatial Resolution Functional Contrast

Figure 7D:
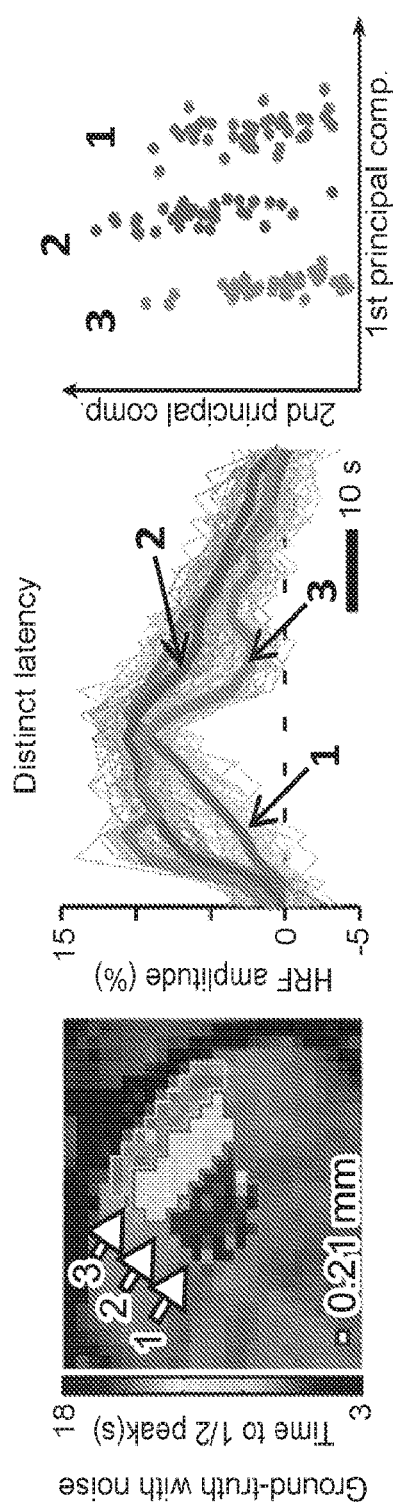
Figure 7E:
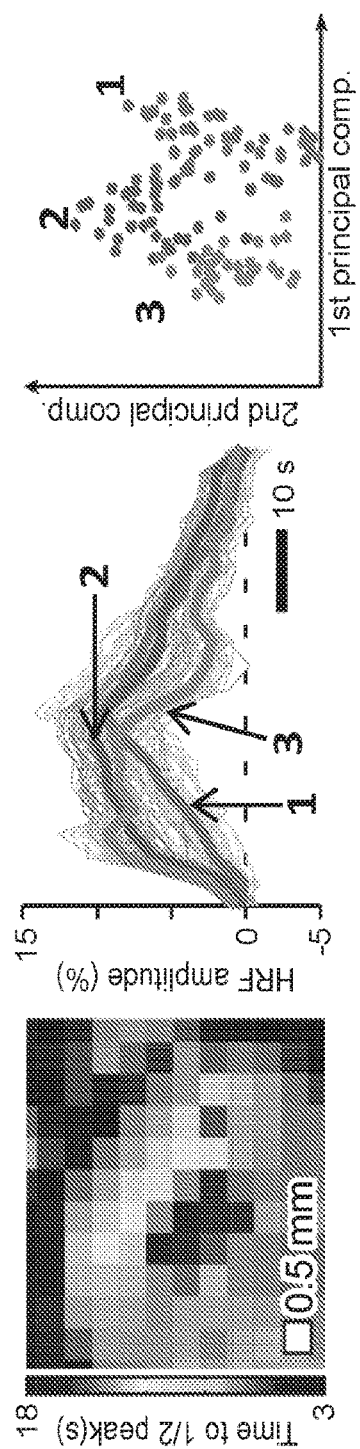
Figure 7F:
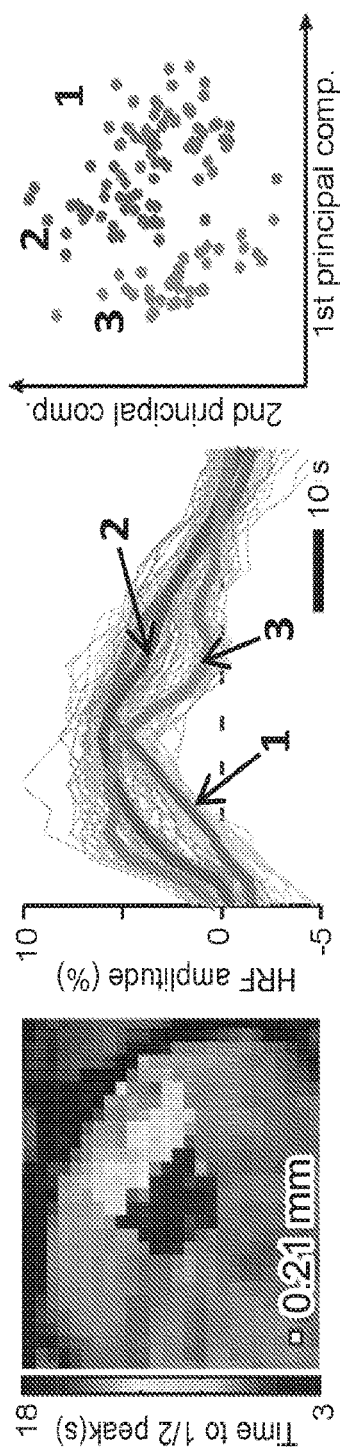

The HSPARSE method was systematically evaluated to determine whether it can detect differences between functionally distinct yet spatially adjacent regions. The first test was performed on a three-layer phantom with distinct peak HRF amplitudes of 15, 10 and 5% (FIG. 7A). With the highest spatial resolution Nyquist acquisition, the borders between the three layers became obscured (FIG. 7B). However, using the HSPARSE method, the three layers were well preserved with clear boundaries among layers. The HSPARSE raw HRFs and their corresponding first two principal component analysis (PCA) coefficients also showed better separation than those of the Nyquist image (FIG. 7C). A similar test was conducted using the same phantom containing three HRFs with distinct latency (FIG. 7D). Similarly, the borders among three layers became obscured with the Nyquist acquisition (FIG. 7E), while the three layers were accurately resolved by the HSPARSE method (FIG. 7F).

The second test was performed on a phantom with a pattern containing 6 interleaved layers of high and low (12 and 4%) amplitude activity (FIG. 8A). With the Nyquist acquisition, the layer specificity cannot be resolved (FIG. 8B). However, the HSPARSE fMRI accurately reconstructed the 6 layers of activation with clear boundaries (FIG. 8C). Similar results were also achieved with two HRFs with distinct latency (FIG. 8D, 8E).

Finally, the resolution limit of the HSPARSE fMRI method was investigated using an interleaved pattern phantom with minimum layer thickness ranging from 1- to 4-pixels. As shown in FIG. 8G, with different peak amplitudes across layers, the HSPARSE method successfully resolved layers down to 1-pixel (0.21 mm) thickness while the Nyquist acquisition can only distinguish the differences down to 3-pixel (0.63 mm). Similarly, the HSPARSE method also showed high spatial resolution down to 1-pixel thickness with layers containing distinct latency but the Nyquist acquisition failed when layer thickness below 3 pixels (FIG. 8H).

With this test, some sinusoidal variations in the HSPARSE reconstructed HRFs were observed (FIG. 7C, 8C and FIG. 14C, 14D Third plot from the top). This was likely due to the DCT regularization and can be reduced by utilizing higher compression ratio transforms such as KLT and DWT. However, importantly, key HRF characteristics were found and their differences among layers were well preserved.

2.6 Resolves In Vivo Layer-Specific Activation Localized to the Dentate Gyrus

Figure 9D:
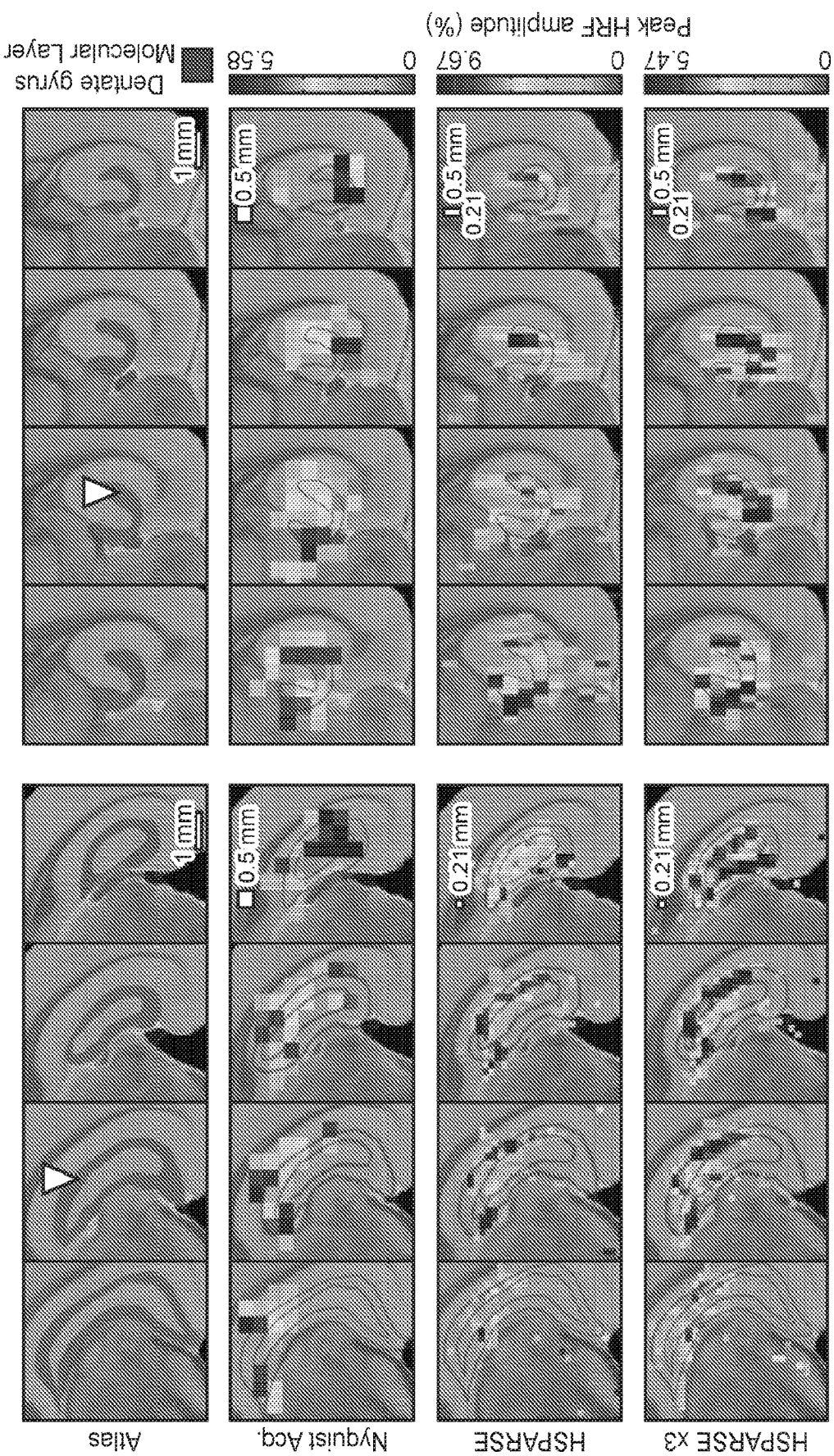
(FIG. 9D) The Nyquist acquisition failed to accurately localize dentate gyrus activity and activity occurs on both the dentate gyrus and the CAL In contrast, both the original and the three times averaged HSPARSE fMRI showed activity localized to the dentate gryus, with the voxels having high peak HRF amplitude precisely following the geometry of the structure's molecular layer. White triangles in the top row indicate the approximate site of stimulation. Active voxels were identified as those having an F-value greater than 4.42 (p<0.001). The active voxels' peak HRF amplitudes were then calculated and overlaid onto a high-resolution MRI atlas, with a threshold at the median plus 1.5 times the standard deviation of all peak HRF amplitudes for clear visualization with good dynamic range.
Figure 15B:
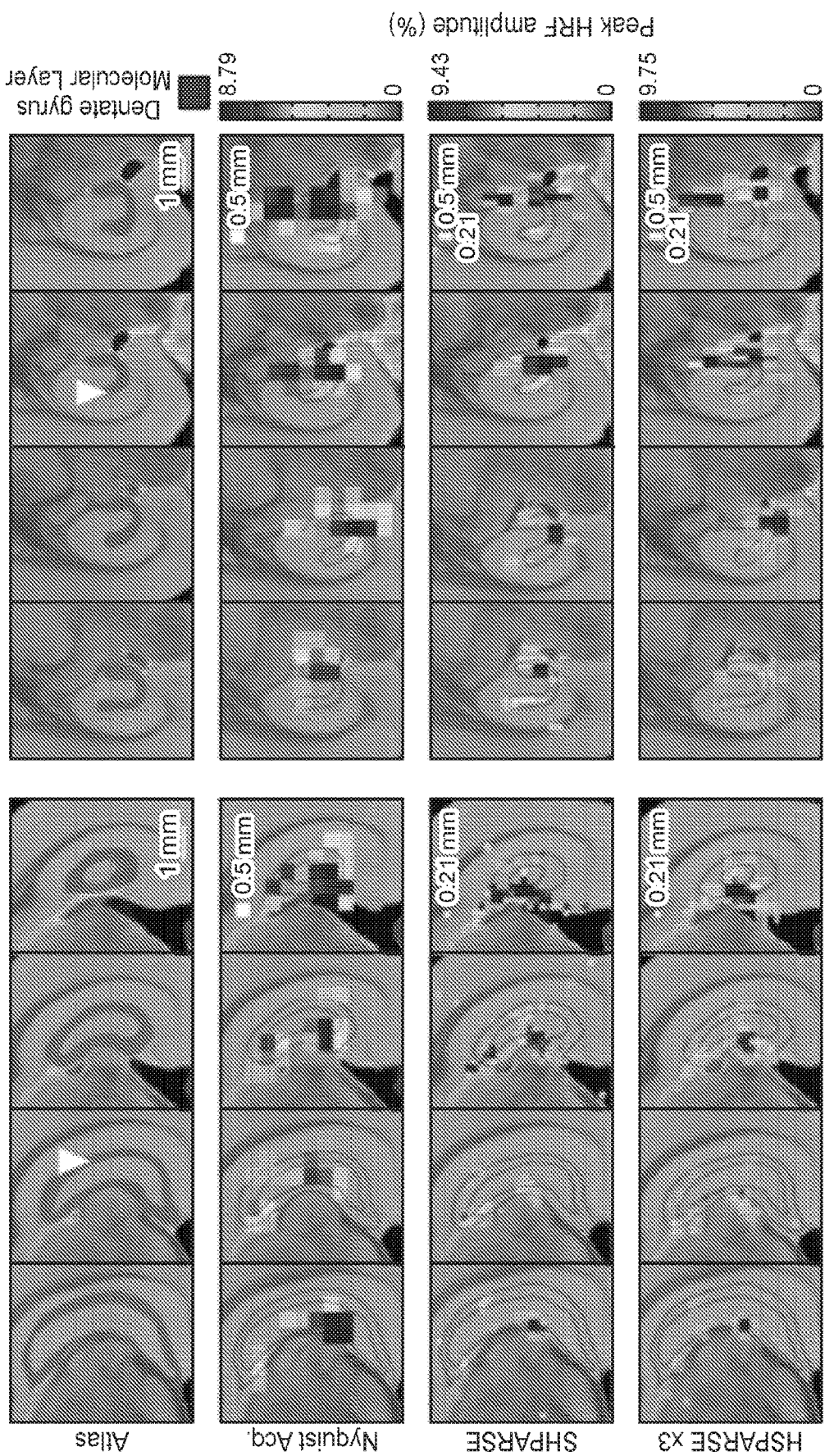

The optimized HSPARSE fMRI method was further tested in vivo using optogenetic stimulation of the rat dentate gyrus. The dentate gyrus was targeted (FIG. 9A) due to its well-defined layered structure (FIG. 9B) and its function as a gate of the unidirectional hippocampal circuit, which can provide predictable activity patterns in hippocampus and downstream structures. Histological examination confirmed that Channelrhodopsin2-EYFP expression was localized to the dentate gyrus (FIG. 9C), indicating successful targeting of this region for light stimulation. For fMRI, both the Nyquist and HSPARSE reconstructed images revealed activity in the dentate gyrus. However, in both the single and the three times averaged HSPARSE images, high peak HRF amplitude (e.g. top 40%) activities were found to be localized precisely following the geometry of the molecular layer in the dentate gyrus while there was no obvious pattern observed in the Nyquist image (FIG. 9D). The Nyquist image also showed activity in adjacent CA1. As reported by Angenstein et al., dentate gyrus activity may be localized or, when activity propagates beyond the dentate gyrus, the entire hippocampal circuit was activated together with downstream regions such as the ipsilateral entorhinal cortex and subiculum. Since no activity was detected in these downstream regions, it was likely that the adjacent CA1 activity detected by the Nyquist scan reflected a partial volume effect due to low spatial resolution. Similar results were observed when the experiments were repeated in two other subjects, indicating the consistency of the HSPARSE method's precise spatial localization ability (FIG. 15).

Figure 9F:
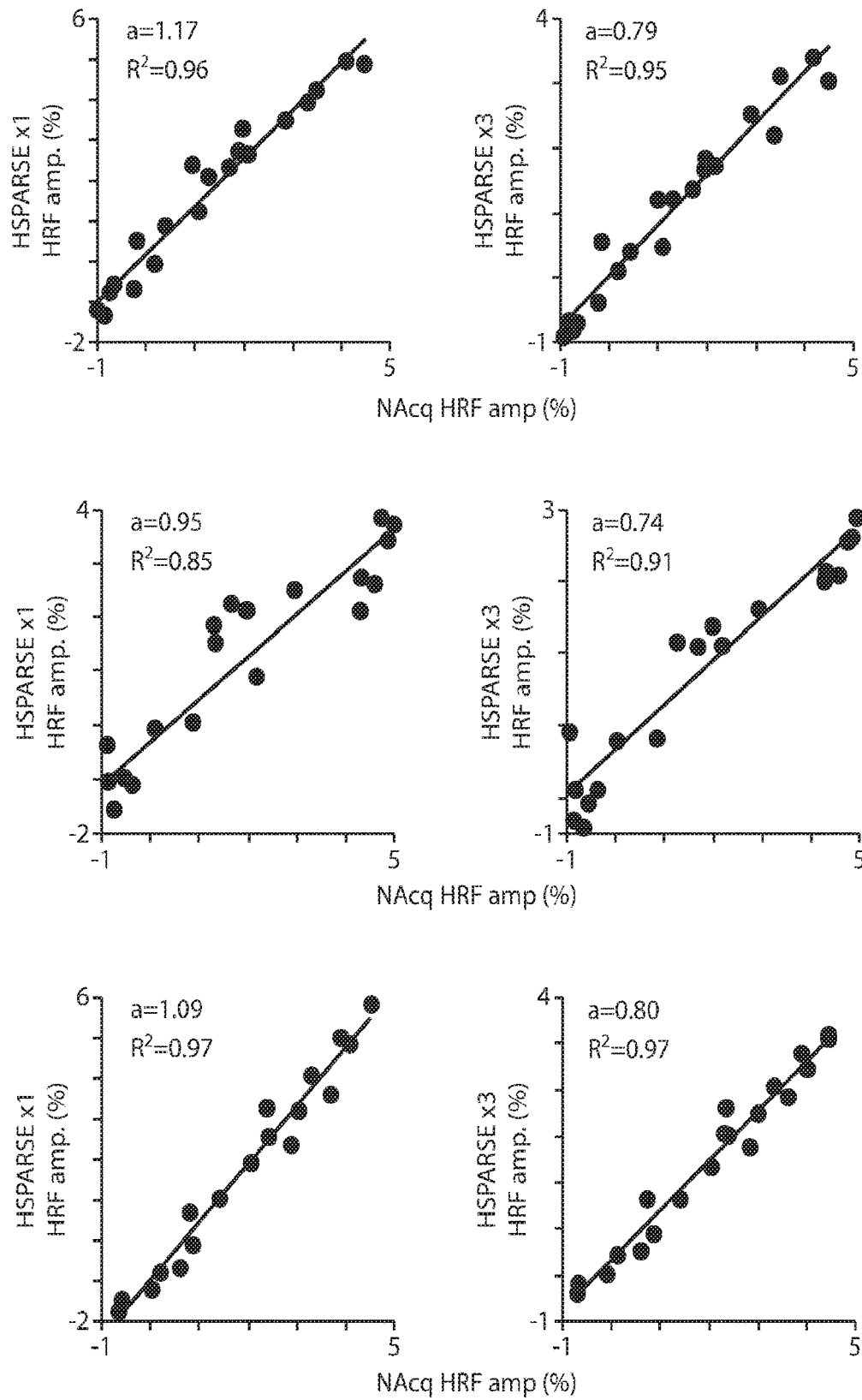

Finally, it was found that HRFs of the single and the three times averaged HSPARSE images and the Nyquist images have strong linear correlation for all three subjects (FIG. 9E, 9F). This indicates that the temporal characteristics were consistent between the Nyquist and the HSPARSE images. Also, all time-to-peak differences between the HSPARSE and the Nyquist images were found to be within the 3 s temporal resolution (FIG. 16). While the durations of activity in two subjects were similar for the HSPARSE and the Nyquist methods on average, the duration was different for one of the subjects. This may be due to biological variation in this subject because the Nyquist and the HSPARSE images were acquired in different imaging sessions. In conclusion, these results demonstrated that HSPARSE can improve localization and identify layer-specific activities in vivo.

2.7 HSPARSE fMRI

HSPARSE fMRI can provide approximately 6-fold improvement in spatial resolution and resolve layer-specific activations in vivo. The HSPARSE fMRI was shown to support an acceleration factor of 5.3, which was 32% higher than the previous fMRI studies using a single coil setup (Holland et al., 2013, Zong et al., 2014). With the HSPARSE fMRI, improved CNR, high sensitivity, low FPR, and low HRF distortion was achieved without compromising temporal resolution. The HSPARSE fMRI also showed high robustness against physiological noise, and was capable of resolving layer specific activations. Finally, in vivo experiments revealed that the HSPARSE fMRI enabled precise localization of dentate gyrus activity that could not be resolved with the highest spatial resolution Nyquist acquisition.

2.8 Optimal Regularization Parameters for HSPARSE fMRI

The role of regularization parameters in fMRI reconstruction and their systematic optimization has been studied. As shown in FIG. 10, the global optimal range does not include the smallest $\lambda_1$ or $\lambda_2$ values (i.e. $\lambda_1=5e^{-5}$ or $\lambda_2=1e^{-9}$), which indicated neither utilizing only spatial regularization nor utilizing only temporal regularization can achieve the same high quality as the combined method. As shown in FIG. 10A, only utilizing the spatial regularization was not enough to eliminate the noise-like aliasing artifact with a high acceleration factor of 5.3. On another hand, while temporal regularization alone can be used to reconstruct the image, the additional spatial regularization can further improve the HRF amplitude and reduce the NRMSE (FIG. 10B). The common optimal parameters can be identified for distinct activity patterns and background images. Because the ground-truth data was not available for real imaging situations, such generalizable optimal regularization parameters were essential for the practical feasibility of the HSPARSE fMRI.

The b-SSFP sequence used for the current implementation of the HSPARSE fMRI requires two acquisitions to avoid banding. The b-SSFP has added benefits including significantly less spatial distortion than conventional GRE acquisitions and high microvascular sensitivity.

2.9 Applications of HSPARSE fMRI

Although b-SSFP sequence was used for the current method's implementation, the random under-sampling spiral acquisition can also be applied to other sequences, such as GRE or spin-echo. In addition, the HSPARSE fMRI can be combined with other high resolution techniques such as parallel imaging to further improve SNR and image resolution. Furthermore, the technique can be generally applied to different field strengths, RF coils, and gradients, enabling wide application of HSPARSE fMRI.

The HSPARSE will also benefit a wide range of neural circuitry studies. For example, while the dentate gyrus may play a key role in pattern separation, Nyquist acquisition fMRI failed to test this hypothesis due to insufficient spatial resolution. Similarly, the HSPARSE fMRI can also resolve cortical layer-specific activities for building cortical processing models. Given these questions and the need for higher spatial resolution throughout the scientific community, the improvement provided by the HSPARSE method offers an important tool for the advancement of fMRI.

Example 2

3.1 GPU Based HSPARSE fMRI Reconstruction

Figure 3B:
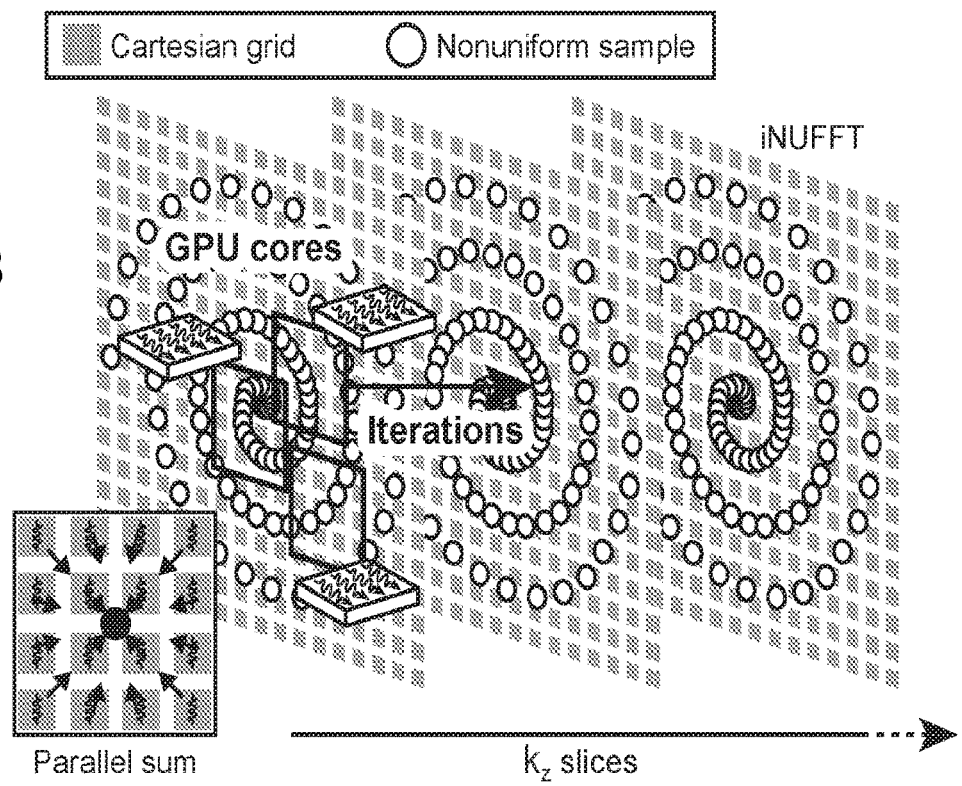
(FIG. 3B) iNUFFT resamples the gray Cartesian grid onto the blue spiral samples. In the parallel implementation, each GPU core was assigned a spiral sample, and each thread inside the GPU core was assigned a Cartesian grid within the corresponding spiral sample's convolution window. During the iNUFFT, each thread first calculates its Cartesian grid's contribution to the given spiral sample, then an efficient binary summation algorithm was performed to sum all values together.
Figure 3C:
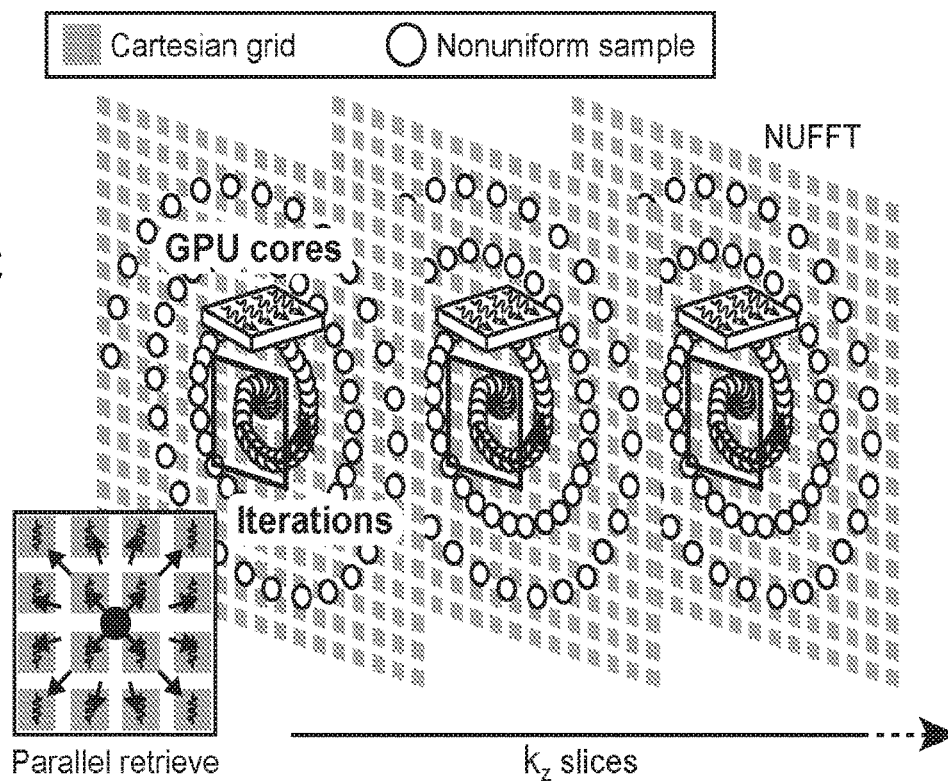
(FIG. 3C) NUFFT resamples the blue spiral samples back onto the Cartesian grids. In contrast to the iNUFFT, each GPU core was assigned to a spiral sample at a different kz-location to avoid memory write conflict. Each thread inside the core then retrieves value from the spiral sample point and adds it to the corresponding Cartesian grid inside the convolution window. Because there were thousands of kz slices in the 4D fMRI datasets, this NUFFT algorithm took full advantage of the massive number of GPU cores.

The randomly under-sampled datasets were reconstructed with a modified gradient descent method (FIG. 4). However, this iterative process was highly computationally intensive, especially when the whole 4D dataset needs to be reconstructed at the same time to fully exploit the temporal sparsity. To enable fast reconstruction, all NUFFT, inverse NUFFT (iNUFFT), matrix arithmetic, and sparsifying transform (DCT) computations were paralellized onto the GPU. Among all of the processing steps, the NUFFT and iNUFFT were the most computationally intensive. As shown in FIG. 3B, 3C, the NUFFT and iNUFFT convolution processes that resample the k-space between Cartesian grids and non-uniform trajectories can be significantly accelerated by thousands of simultaneous GPU threads. Compared to a CPU based HSPARSE fMRI reconstruction, the GPU based method achieves 34-fold overall improvement in reconstruction speed (FIG. 17).

3.2 Evaluation of Robustness with Motion

Figure 18A:
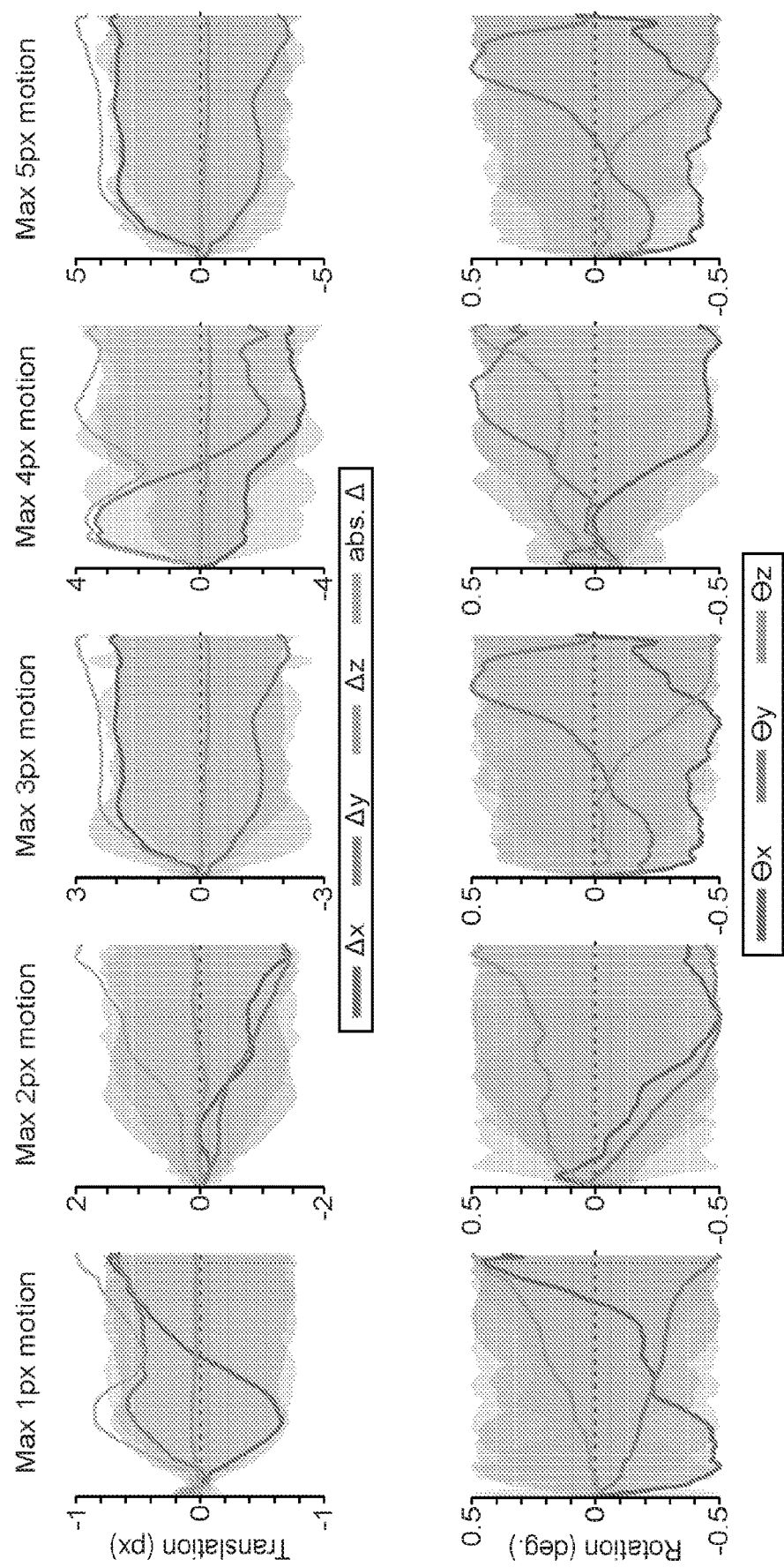
(FIG. 18A) Five sets of motion profiles with a maximum absolute translation equivalent to 1- to 5-pixels were designed. To simulate realistic motion, the z-dimension translation was restricted to be smaller than the x- and y-dimension translations, and rotations about the x-, y- and z-axis were limited to within ±0.5 degrees. Solid lines represent an example six degree-of-freedom motion profile and shaded areas represent the ranges of translations or rotations in each motion profile.

The robustness of HSPARSE fMRI was investigated to motion, which was a common source of signal degradation in fMRI. In the simulation, 25 different sets of motion profiles with maximum absolute translations of 1 to 5 pixels (0.21 to 1.05 mm) were separately added to the A3 phantom (FIG. 18A). The A3 phantom (FIG. 18C) was selected because its well-defined activity boundary could best facilitate the evaluation of motion-induced fMRI artifacts. Based on measurements from in vivo datasets, smaller translations were applied in the z dimension and the rotation angle of each axis was limited to within ±0.5 degrees. After the phantoms with motion were reconstructed, they were motion corrected by the inverse Gauss-Newton motion correction algorithm.

Figure 18B:
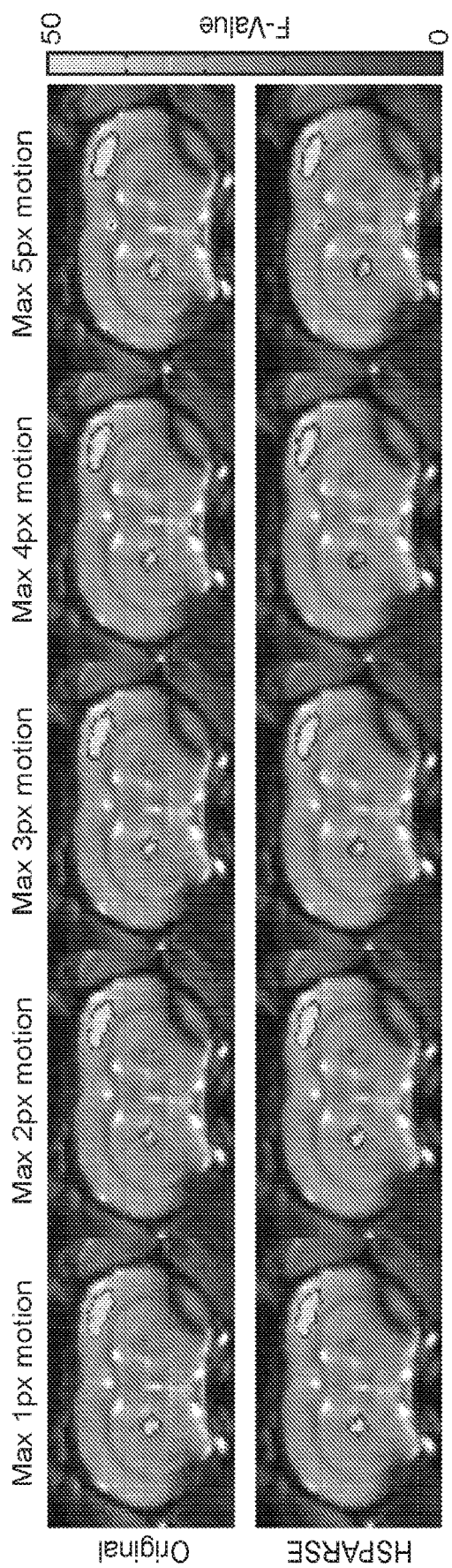
(FIG. 18B) The motion corrected HSPARSE images show similar activations as the motion corrected original images when the motion was 1-5 pixels.
Figure 18C:
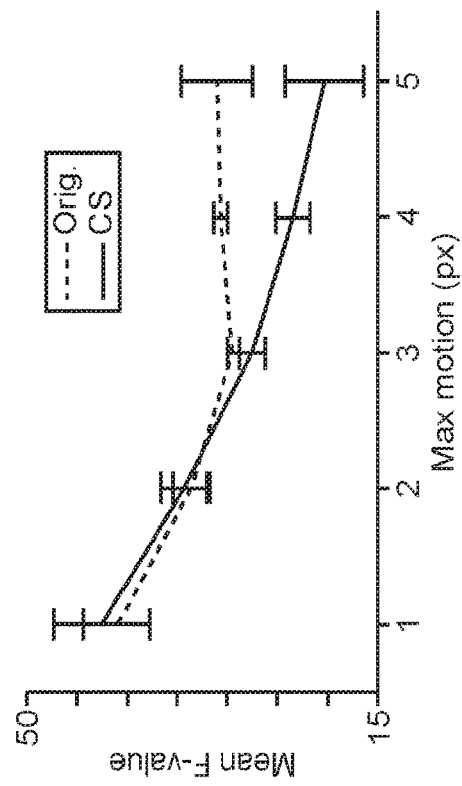
Figure 18E:
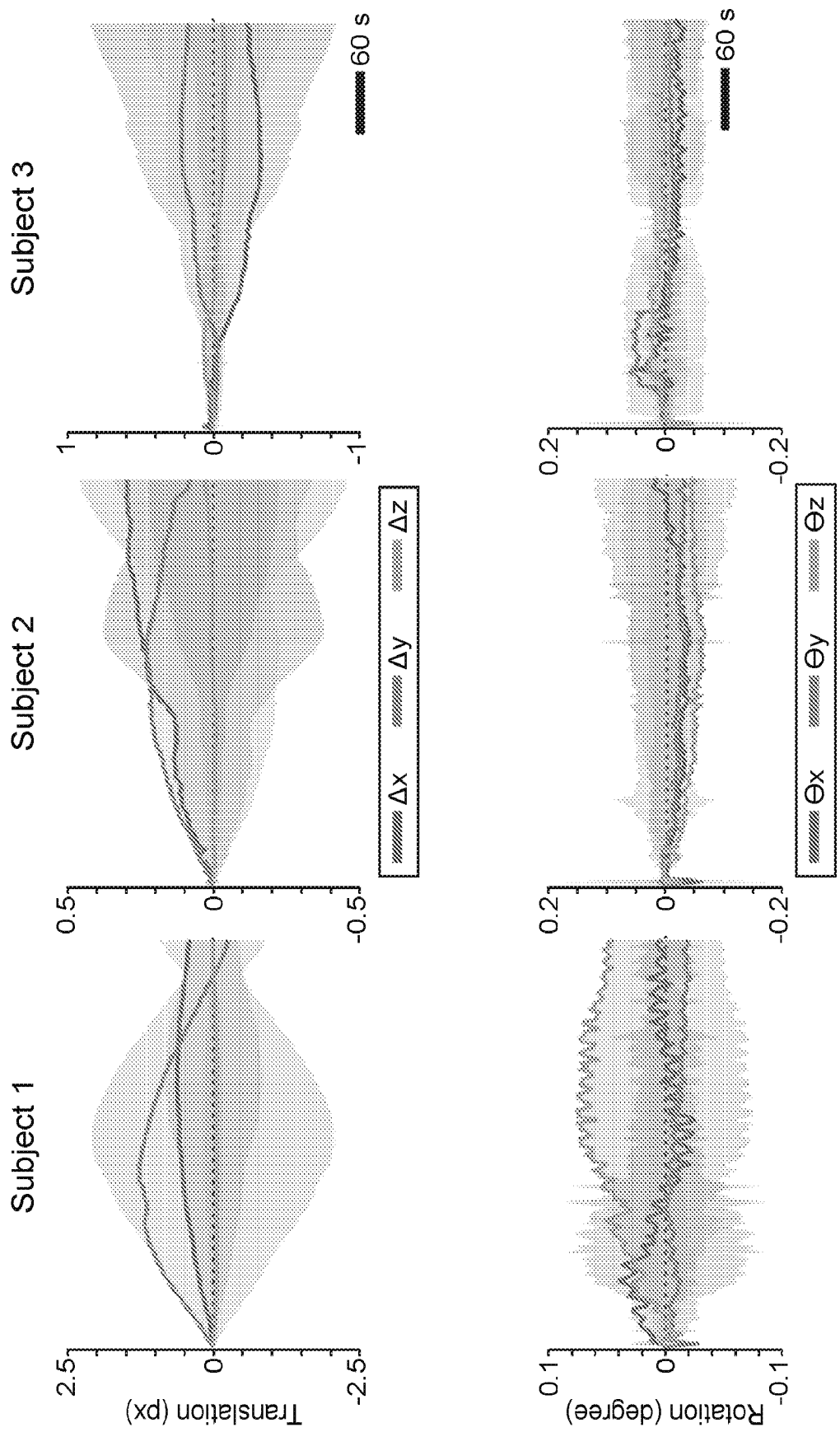
(FIG. 18E) Motion profiles of the three experiment subjects indicated that the physiological motion in the in vivo experiments were well within the 4-pixel range of robust reconstruction with the HSPARSE method. They exhibited translations of less than 2.5-pixels and rotations of less than ±0.2 degrees.

FIG. 18B shows that when the amount of motion increases, the number of false positive voxels increases in both the original and the HSPARSE reconstructed images, while the difference between the HSPARSE and the original images was small. When the motion was larger than 3-pixels, the mean F-value of the HSPARSE images decreased compared to the original images (FIG. 18C). When the motion was larger than 4-pixels, the HSPARSE images had lower sensitivity compared to the original images (FIG. 18D). Therefore, while there were minimal differences even up to 5-voxel motion, the HSPARSE fMRI method was robust to motion up to 3-pixels by all measures. The amount of motion in the high spatial resolution in vivo experiments was then evaluated, during which the subjects' heads were fixed with teeth and ear bars. FIG. 18E shows that the maximum amount of translation was less than 2.5-pixels and rotation was less than 0.2 degrees in all three subjects, which indicated the HSPARSE fMRI reconstruction method was robust for the head-fixed experimental setup.

Example 3

Real-time fMRI (rtfMRI) has been applied in many fields such as the brain machine interface, presurgical planning, and neuronal feedback control. However, it remains challenging to achieving high spatiotemporal resolution rtfMRI. This was because the resolution improvement results in a significantly high computational overhead. In addition, although many high-resolution techniques have been applied to the rtfMRI, even higher resolution may be needed when investigating functions of cortical layers and hippocampal sub-regions.

Here, compressed sensing (CS) was used to solve this problem. CS exploits the signal redundancy in certain domain and enables signal reconstruction from its under Nyquist rate sampled measurements. Due to the natural massive redundancy in the MRI image, CS can be used in MRI to achieve higher imaging speed, signal to noise ratio (SNR), and spatial resolution. For the functional MRI (fMRI), CS can improve the spatiotemporal resolution, contrast to noise ratio (CNR), and sensitivity. Being an under-sampling method, CS can be implemented within the limit of available MRI scanner hardware. CS can also be integrated with other techniques such as the parallel imaging to further improve the resolution.

In aspects of embodiments of the current disclosure, a real-time high-resolution CS fMRI method was demonstrated, which can reconstruct a 3D stack of variable density spiral sampled and 140×140×32 matrix sized image in less than 605 ms. With an optimized random stack of variable density spiral, highly incoherent sampling was achieved with an acceleration factor of 3.6 and 4-fold spatial resolution improvement. With this real-time high-resolution CS fMRI method, improved CNR, mean F-value and sensitivity with low false positive rate was also achieved. This method can also resolve layer specific activities that cannot be resolved with the highest spatial resolution Nyquist sampled image.

Materials and Methods 4.1 Randomized Stack of Variable Density Spiral

Incoherent measurement of k-space was required for CS reconstruction. Although random skipping phase encodings following a Gaussian-like distribution in Cartesian imaging results in highly effective incoherent sampling, random skipping interleaved readouts in spiral imaging does not produce enough incoherency and temporal regularization was required for eliminating the aliasing artifact. However, temporal regularization requires simultaneous reconstruction of whole/part of the fMRI dataset, which requires extremely high computational power. Furthermore, temporal regularization also introduces unavoidable temporal distortion. Therefore, a simple but effective spiral under-sampling strategy was used for the real-time compressed sensing fMRI.

A trajectory design similar to the Variable Density Randomized Stack of Spirals (VDR-SoS) technique was used for the real-time compressed sensing fMRI. VDR-SoS trajectory outperforms the standard stack of spirals trajectory with a much higher acceleration factor and sampling incoherency. The reconstruction of the VDR-SoS sampled image was also faster than other 3D compressed sensing trajectories and produced a similar reconstruction quality.

An Archimedean spiral trajectory can be described in the polar coordinate as:

$$k = k_r e^{j\theta} \quad (5.1)$$

where $k = k_x + ik_y$, $r = \sqrt{k_x^2 + k_y^2}$ and $\theta = \tan^{-1}\left(\frac{k_y}{k_x}\right)$.

Figure 24A:
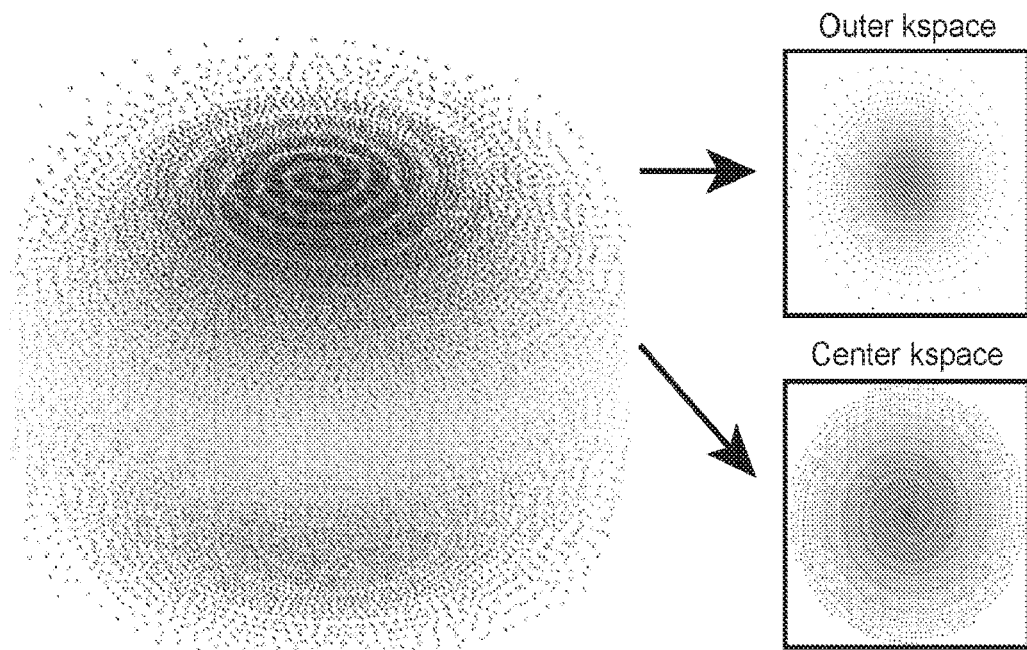
Figure 24B:
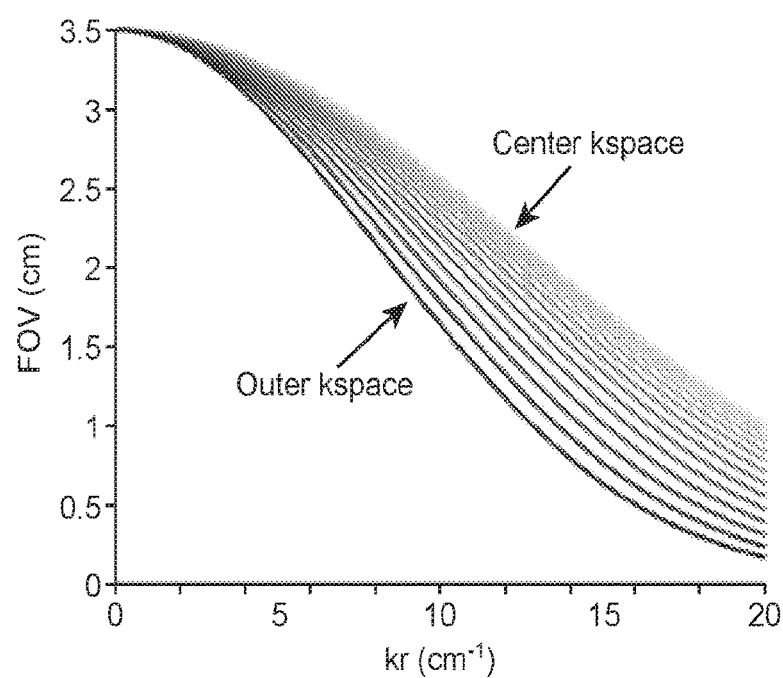

For spiral imaging, the change rate in the radial direction ($\Delta k_r$) versus the change rate in the angular direction ($\Delta\theta$) can be determined by the effective FOV ($FOV_e$) in the x and y.

$$\frac{\Delta k_r}{\Delta \theta} = \frac{N}{2\pi FOV_e} \quad (5.2)$$

where $N$ was the number of interleaves. By adjusting the effective FOV, different variable density spiral can be achieved. FIG. 24A, 24B and Eq. (5.3) show a design of a random stack of variable density spirals (VDS) trajectory with effective FOV following an exponential function:

$$FOV_e = FOV_0 \exp\left(-\left(\frac{k_r}{ak_{rmax}\exp\left(-\left(\frac{k_r}{bk_{zmax}}\right)^2\right)}\right)^2\right) \quad (5.3)$$

where $FOV_0$ was the desired field of view (e.g., 3.5 cm), $k_{rmax}$ was the maximum value of $k_r$ ($1/(2\times\text{resolution in x and y})$), $k_z$ was location for each $k_z$-slice, and $k_{zmax}$ was the number of $k_z$-slices. The parameter a and b control the variance of the exponential function along $k_r$ and $k_z$ direction and determine the acceleration factor.

Following the effective FOV constraint (Eq.(5.3)), if the number of interleaves was maintained across different $k_z$-slice, the readout duration would decrease when $k_z$ increases. Therefore, readouts on different $k_z$-slices would subject to different off-resonance effects. In order to avoid this, the number of interleaves on each $k_z$-slice was designed to decrease with the increase of $k_z$, and the number of interleaves was set to the integer that gave the closest number of readouts as the center $k_z$-slice. Because this technique also reduced the total number of interleave, a high acceleration factor can be achieved.

To introduce higher incoherency into the sampling trajectory, the angle of each interleaf was randomly disturbed with a maximum angular change of $0.05\times\pi/N_z$. Because achieving the exact total number of desired interleaves for each 3D volume was not trivial for this trajectory, the trajectory was first designed with a slightly larger total number of interleaves by adjusting the parameters a and b. Then sampling was randomly skipped on some of the interleaves on the outer k-space following a Gaussian distribution.

The random stack of VDS trajectory was then applied for the high spatial resolution fMRI. A fully-sampled stack of spirals trajectory with the highest achievable spatial resolution was first designed, with 35×35×16 mm field of view, 0.5×0.5×0.5 mm spatial resolution, and 70×70×32 matrix size. There were 10 interleaves in each $k_z$-slice and 432 readouts in each interleaf. A randomized stack of VDS trajectory was then designed with same FOV but 4 times spatial resolution improvements in both the x and y dimension (i.e., 0.25×0.25×0.5 mm spatial resolution) compared to the fully-sampled trajectory. Parameter a, b, and the number of readout and interleaves were empirically picked based on the sparsity of the resultant point spread function (a=0.9, b=1.4). With these parameters, an acceleration factor of 3.6 was achieved compared to the fully-sampled high spatial resolution spiral sequence. The results show that this parameter choice also produced highly incoherent sampling. The fully-sampled and the random under-sampled trajectories were implemented into a balanced steady state free precession sequence with TR/TE=9.237/2 ms and 3 s temporal resolution.

4.2 Reconstruction with the FISTA

The randomly under-sampled dataset was reconstructed in real-time using an l1 Wavelet spatial regularization:

$$f(m) = \tfrac{1}{2}\|Fm-b\|_2^2 + \lambda\|\Psi_S m\|_1 \quad (5.4)$$

where m was the image under-reconstruction, b was the raw k-space sample, F was the non-uniform Fourier transform, and $\Psi_S$ was the three dimensional Daubechies-4 discrete Wavelet transform (DWT).

This cost function was solved in real-time with the fast iterative shrinkage thresholding algorithm (FISTA), which provides a high convergence speed. In addition, because computation of the l1 norm gradient was not required in FISTA, the computational complexity of the FISTA in each iteration was much lower than the gradient descent based methods.

Because FISTA only supports $\|x\|_1$ instead of $\|\Psi x\|_1$ regularization, the cost function was modified to reconstruct the image in the Wavelet domain.

$$f(m) = \tfrac{1}{2}\|F\Psi_S^* w - b\|_2^2 + \lambda\|w\|_1 \quad (5.5)$$

where $\Psi_S^*$ was the inverse Wavelet transform. After reconstruction with Algorithm 1(FIG. 19), the final image can be obtained by taking the inverse DWT of w.

Algorithm 1, shown in FIG. 19 was implemented on a Graphical Processing Unit platform. Several repeatedly computations such as the non-uniform FFT (NUFFT), inverse NUFFT, DWT and inverse DWT were carefully optimized. For the NUFFT, a pre-sorting algorithm was implemented. A custom build workstation was used for the real-time reconstruction with Intel quad-core 2.66 GHz CPU, Nvidia 2048 cores CUDA GPU and 16 GB CPU memory.

4.3 fMRI Analysis

The general linear model analysis was performed with five gamma basis for the real-time reconstructed datasets. An F test was then performed with active voxels recognized as those having an F-value larger than 4.12 (P<0.001).

A phantom with 30 dB SNR was first designed to identify the optimal CS regularization parameter and evaluate the real-time reconstruction quality. Six-cycle 20s-on-40s-off canonical statistical parametric map (SPM) hemodynamic response function (HRF) were added to the phantom with a spatial distribution simulating in vivo experiments. The peak HRF amplitude of the fMRI signal was set to be 5% modulation, resulting into a CNR of 1.28. Six different regularization parameters were tested ($1e^{-2}$, $5e^{-3}$, $1e^{-3}$, $5e^{-4}$, $1e^{-4}$, $5e^{-5}$). The quality of the reconstructed fMRI images was then evaluated by comparing the contrast to noise ratio (CNR), mean F-value, peak hemodynamic response function (HRF) amplitude, sensitivity, and false positive rate to the corresponding metrics of the ground-truth image. Normalized root mean squared error between the reconstructed and the ground-truth images were also compared. The sensitivity was measured by the number of active voxels within the originally designed active region over the total number of voxels of the designed active region. The false positive rate was measured by the number of active voxels within the first and the second voxel perimeter layers of the designed active region over the total number of voxels within the first and the second voxel perimeter layers.

Results

5.1 Real-Time CS Reconstruction

Figure 20A:
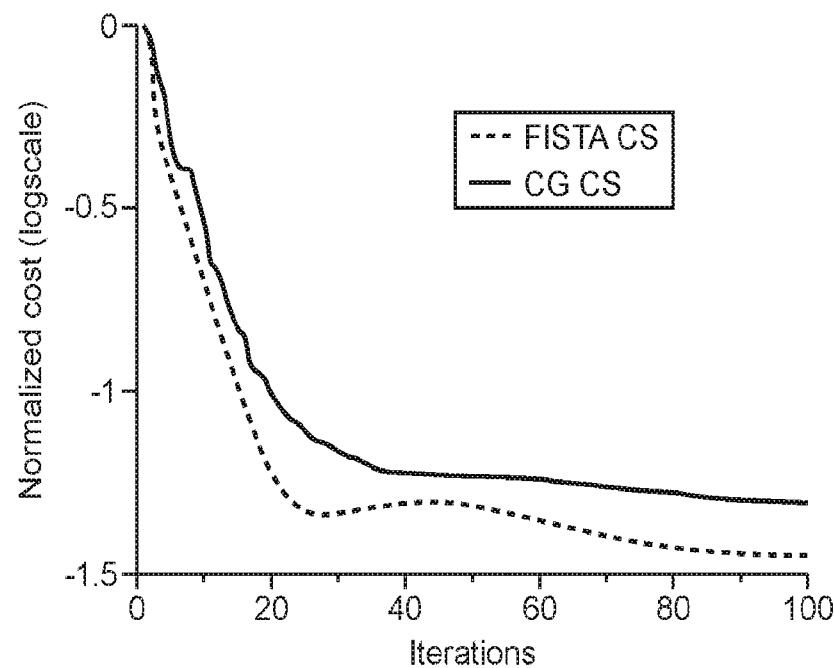
(FIG. 20A) FISTA method showed a much faster convergence speed and lower cost than the widely used conjugate gradient method. Because FISTA was not a descend method, an increase of the cost in some iterations was observed.

The convergence speed of the FISTA MRI reconstruction was first compared with the widely used conjugate gradient descend MRI reconstruction method (CG) (Lustig et al., 2007). As can be seen in FIG. 20A, the FISTA MRI reconstruction method showed a much faster convergence speed (about 30 iterations) than the CG method. FISTA MRI reconstruction also resulted in a much lower cost.

Figure 20B:
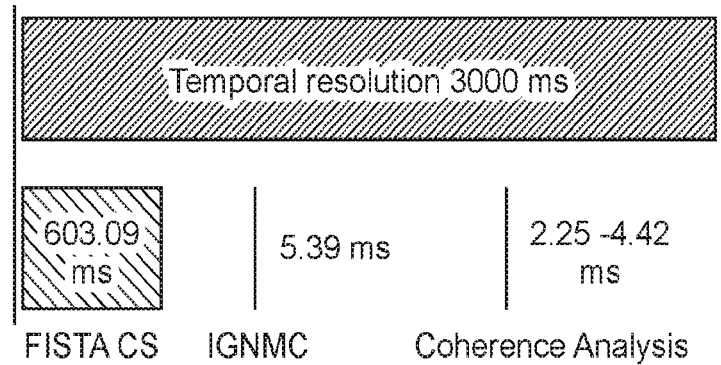
(FIG. 20B) With GPU optimization, FISTA method successfully reconstructed a 140× 140×32 matrix sized image within 605 ms. Combining with the IGN motion correction and coherence analysis, the overall real-time processing took less than 620 ms and only consists 20% of the consecutive image duration.
Figure 20C:
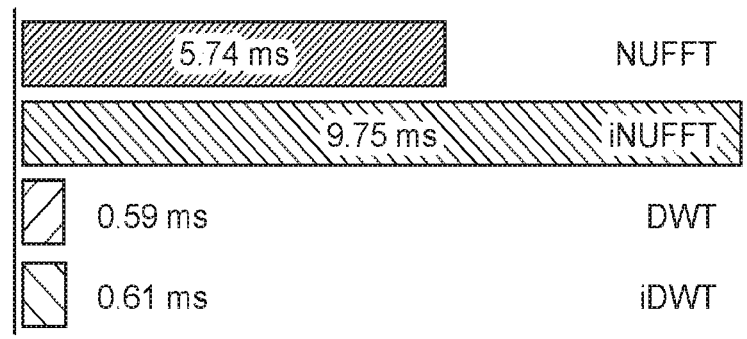
(FIG. 20C) Repeatedly used computations such as the NUFFT, iNUFFT, DWT, and iDWT were calculated efficiently by the GPU.

As shown in FIG. 20B, 20C, the computation speed of the FISTA reconstruction was measured on a GPU. With the GPU optimization, the NUFFT took 5.74 ms and the inverse NUFFT took 9.75 ms. The highly optimized DWT and inverse DWT only took 0.59 ms and 0.61 ms respectively. The overall FISTA reconstruction (30 iterations) took 603.09 ms, which was only 20% of the duration between consecutive fMRI images. The real-time inverse gauss newton motion correction (IGNMC) and coherence analysis took less than 5.39 ms and 4.42 ms. The total processing time of the real-time system was less than 620 ms. This high speed enabled future integration of advanced analysis algorithms into the real-time system such as the brain state classification. Moreover, this fast processing speed also indicated the real-time system can be used for high temporal resolution CS fMRI.

5.2 Reconstructed Image Quality

FIG. 21 shows the comparison of the zero-filling reconstructed dataset with the ground-truth image. As can be seen, the designed random stack of VDS trajectory showed significantly high incoherence in the sampling, i.e., the aliasing artifact was highly noise like. The real-time CS reconstructed images was then evaluated with the optimal regularization parameter (see next section $\lambda$=1e-3). The FISTA algorithm was successfully removed the noise like aliasing artifacts compared to the zero-filling reconstruction. Although the CS reconstructed image was smoother than the ground-truth image due to the spatial regularization, the CS reconstructed image showed that it can still detect layer specific activity that cannot be resolved by using the highest spatial resolution Nyquist sampled image.

5.3 Optimal Regularization Parameter

Figure 22:
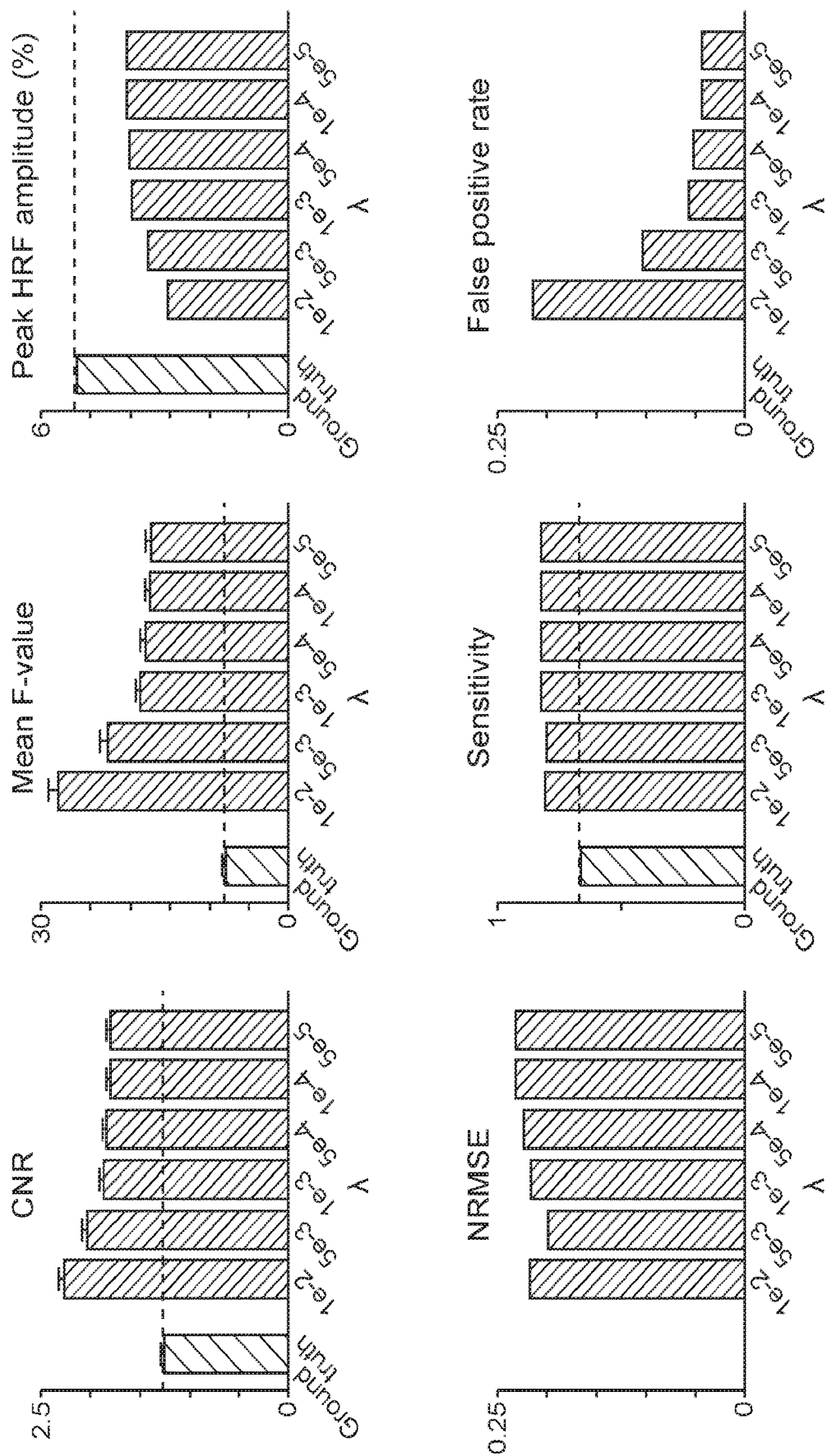
FIG. 22: Real-time high-resolution CS fMRI achieved improved CNR, mean F-value, sensitivity and low FPR. A range of parameters were tested to identify the optimal regularization parameters for the real-time high-resolution CS fMRI. After comparing different metrics shown in the Figure, it was found that $1e^{-3}$ and $5e^{-4}$ offer the best trade-off between metrics and result in improved CNR, mean F-value, sensitivity and low FPR.

The optimal regularization parameter was identified by scanning through a range of potential optimal parameters. As shown in FIG. 22, when the regularization was strict (such as when $\lambda=1e^{-2}$), the image was smooth and DWT thresholding artifact became observable. When the regularization was loose (such as when $\lambda=5e^{-5}$), the noise level increased.

The CNR, mean F-value, peak HRF amplitude, NRMSE, sensitivity and FPR was then compared across the regularization parameters. The optimal regularization parameters were identified as the intersect of the parameters that gave top 50% CNR, mean F-value, sensitivity, and bottom 50% NRMSE and false positive rate. $\lambda=1e^{-3}$ and $5e^{-4}$ was then identified as the optimal regularization parameter for the reconstruction. With $\lambda=1e^{-3}$, improvement was achieved at 1.47, 2.28, 1.23 times in the CNR, mean F-value and sensitivity respectively, peak HRF amplitude of 3.82%, NRMSE of 0.21 and low FPR of 0.058.

5.4 High Spatial Resolution

Figure 23A:
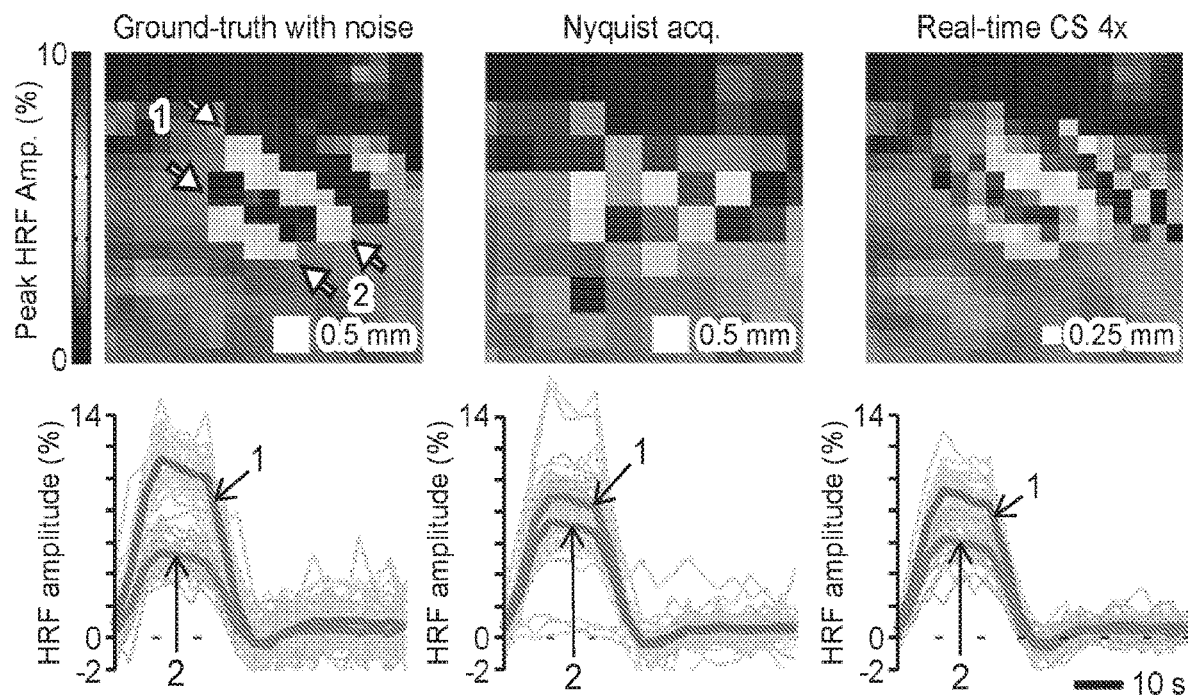
Figure 23B:
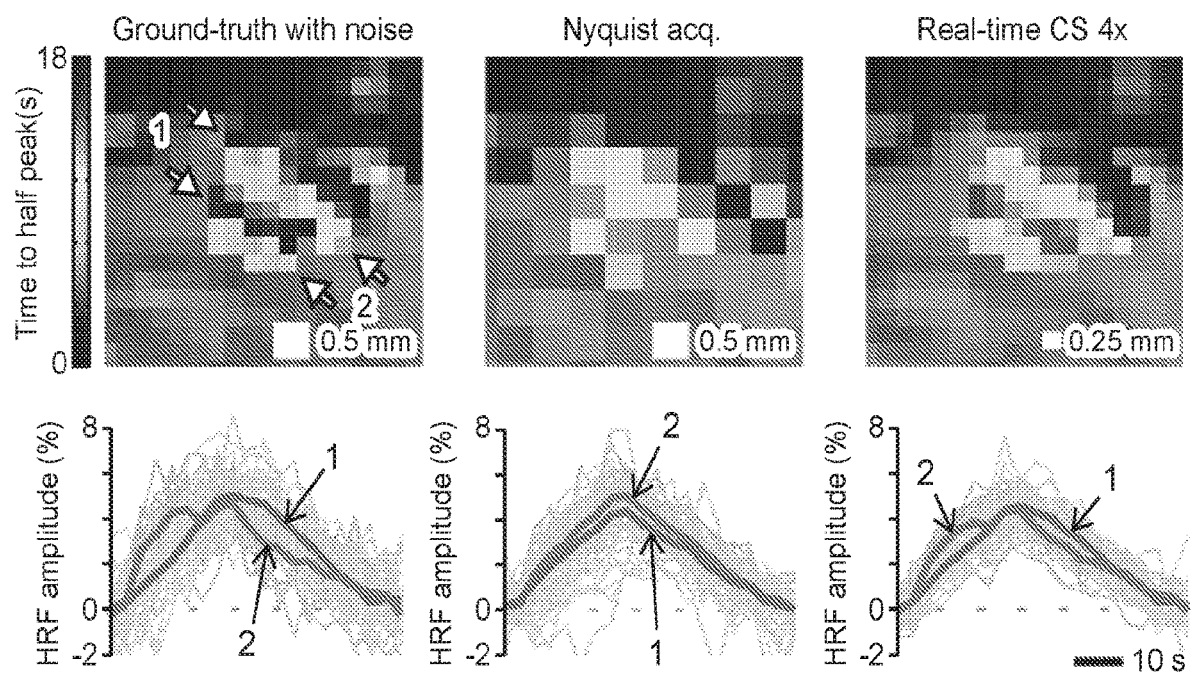

The spatial resolution of the real-time CS fMRI was also tested with phantoms containing layer specific activity. As shown in FIG. 23A, two interleaved layers consisted of signals with distinct peak HRF amplitude were designed in the first phantom. The real-time high-resolution CS fMRI clearly resolved the two layers while the highest spatial resolution Nyquist sampled image completely failed. The raw HRFs color labeled by their corresponding original layer index also confirm the real-time high-resolution CS fMRI outperformed the highest spatial resolution Nyquist sampled method. As shown in FIG. 23B, another two HRFs with distinct latencies were added into the phantom with the same interleaved pattern. It was shown that the real-time high-resolution CS fMRI also successfully resolved the latency between layers, while the highest spatial resolution Nyquist sampled image failed.

5.5 CS fMRI Method

A real-time high-resolution CS fMRI method that can reconstruct a 3D volumetric image (140×140×32 matrix size) in less than 605 ms has been demonstrated. Based on FISTA method, the reconstruction showed much faster convergence speed and accuracy than the widely used conjugate gradient method. With the designed high spatial resolution random stack of VDS, high incoherent sampling was achieved. Improvement by 1.47, 2.28, 1.23 times in the CNR, mean F-value, sensitivity and low FPR of 0.058 after the reconstruction was also achieved. This method can also accurately detect layer specific activity which cannot be resolved by the highest spatial resolution Nyquist acquisition.

5.6 Application of the Real-Time High-Resolution CS fMRI

Many applications can be benefited from the real-time CS fMRI with the 4 times spatial resolution improvement disclosed herein. For example, regions involved in seizure form a highly dynamic network that could vary across subjects and time. With this real-time high-resolution CS fMRI system, seizure propagation can be monitored and tiny but critical brain regions in the network, such as the dentate gyrus, can also be closely studied with the high-resolution provided by the method.

With the reconstruction speed as fast as 605 ms per 3D image, the real-time CS fMRI method can be applied to high temporal resolution imaging with little modification of the scanning trajectory. Similar to the demonstrated high spatial resolution trajectory, a high temporal resolution trajectory can be designed with Eq. 5.3 by reducing the number of interleaves compared to the standard resolution Nyquist image. With the high temporal resolution image, finer fMRI temporal dynamics can be captured and the brain network connectivity can be investigated in real-time.

Furthermore, the real-time high-resolution CS fMRI method can also be combined with the parallel imaging techniques to further improve the image CNR, sensitivity, and to achieve a higher acceleration factor. In summary, the real-time high-resolution CS fMRI of the present disclosure offers an important tool to the advancement of fMRI technology.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for functional magnetic resonance imaging (fMRI) of a subject, the method comprising:
    applying with an MRI system, a balanced steady state free precession (b-SSFP) sequence to a target area in a subject;
    acquiring with the MRI system, image data of the target area in the subject using a randomly undersampled variable density spiral (VDS) trajectory, wherein the VDS trajectory includes a random stack of VDS trajectories, wherein a change in a radial direction versus a change in a rate in an angular direction of the VDS trajectories is determined by a number of interleaves and an effective field of view, wherein the field of view follows an exponential function and an angle between each interleaf of the number of interleaves is randomly distributed; and
    producing an image of the target area in the subject based on the acquired image data.

2. The method of claim 1, wherein the producing comprises analyzing the image data using a spatial sparsifying transform.

3. The method of claim 2, wherein the spatial sparsifying transform comprises a discrete cosine transform (DCT).

4. The method of claim 1, wherein the method is a real-time fMRI method.

5. The method of claim 4, wherein the producing comprises analyzing the image data using a fast iterative shrinkage thresholding algorithm (FISTA).

6. The method of claim 1, wherein the method has a sampling acceleration factor of 2 or more.

7. The method of claim 1, wherein the method has a sampling acceleration factor of 5 or more.

8. The method of claim 1, wherein the method produces an image having a spatial resolution of about 0.2×0.2×0.5 mm$^3$ or greater.

9. The method of claim 1, wherein the method produces an image having a contrast-to-noise ratio of 1.5 or more.

10. The method of claim 1, wherein the method produces an image having a contrast-to-noise ratio of 2.5 or more.

11. A functional magnetic resonance imaging (fMRI) system, the system comprising:
    a coil configured to apply a balanced steady state free precession (b-SSFP) sequence to a target area in a subject;
    a receiver configured to acquire image data of the target area in the subject using a randomly undersampled variable density spiral (VDS) trajectory, wherein the VDS trajectory includes a random stack of VDS trajectories, wherein a change in a radial direction versus a change in a rate in an angular direction of the VDS trajectories is determined by a number of interleaves and an effective field of view, wherein the field of view follows an exponential function and an angle between each interleaf of the number of interleaves is randomly distributed; and
    a processor configured to produce an image of the target area in the subject based on the acquired image data.

12. The system of claim 11, wherein the processor is configured to analyze the image data using a spatial sparsifying transform.

13. The system of claim 12, wherein the spatial sparsifying transform comprises a discrete cosine transform (DCT).

14. The system of claim 11, wherein the system is configured for real-time fMRI.

15. The system of claim 14, wherein the processor is configured to analyze the image data using a fast iterative shrinkage thresholding algorithm (FISTA).

16. The system of claim 11, wherein the system has a sampling acceleration factor of 2 or more.

17. The system of claim 11, wherein the system has a sampling acceleration factor of 5 or more.

18. The system of claim 11, wherein the processor produces an image having a spatial resolution of about 0.2×0.2×0.5 mm$^3$ or greater.

19. The system of claim 11, wherein the processor produces an image having a contrast-to-noise ratio of 1.5 or more.

20. The system of claim 11, wherein the processor produces an image having a contrast-to-noise ratio of 2.5 or more.

* * * * *